(12) United States Patent
Hatakeyama et al.

(10) Patent No.: US 10,078,264 B2
(45) Date of Patent: Sep. 18, 2018

(54) RESIST COMPOSITION, PATTERNING PROCESS, AND BARIUM, CESIUM AND CERIUM SALTS

(71) Applicant: SHIN-ETSU CHEMICAL CO., LTD., Tokyo (JP)

(72) Inventors: Jun Hatakeyama, Joetsu (JP); Takeshi Sasami, Joetsu (JP); Masaki Ohashi, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 15 days.

(21) Appl. No.: 15/331,056

(22) Filed: Oct. 21, 2016

(65) Prior Publication Data

US 2017/0115566 A1    Apr. 27, 2017

(30) Foreign Application Priority Data

Oct. 23, 2015 (JP) ................. 2015-208583
Jul. 7, 2016 (JP) ................. 2016-134659
Sep. 16, 2016 (JP) ................. 2016-181229

(51) Int. Cl.
| | | |
|---|---|---|
| *G03F 7/004* | (2006.01) | |
| *G03F 7/40* | (2006.01) | |
| *C07C 69/74* | (2006.01) | |
| *C07C 69/753* | (2006.01) | |
| *C07C 69/757* | (2006.01) | |
| *C07C 69/78* | (2006.01) | |
| *C07C 69/95* | (2006.01) | |
| *C07C 205/06* | (2006.01) | |
| *C07C 205/11* | (2006.01) | |
| *C07C 303/32* | (2006.01) | |
| *C08F 228/02* | (2006.01) | |
| *G03F 7/039* | (2006.01) | |
| *C07C 309/12* | (2006.01) | |
| *C07J 31/00* | (2006.01) | |
| *C07D 307/00* | (2006.01) | |

(Continued)

(52) U.S. Cl.
CPC ............ *G03F 7/0397* (2013.01); *C07C 69/74* (2013.01); *C07C 69/753* (2013.01); *C07C 69/757* (2013.01); *C07C 69/78* (2013.01); *C07C 69/95* (2013.01); *C07C 205/06* (2013.01); *C07C 205/11* (2013.01); *C07C 303/32* (2013.01); *C07C 309/04* (2013.01); *C07C 309/06* (2013.01); *C07C 309/12* (2013.01); *C07C 309/20* (2013.01); *C07C 309/24* (2013.01); *C07C 309/73* (2013.01); *C07D 307/00* (2013.01); *C07J 31/006* (2013.01); *C08F 228/02* (2013.01); *G03F 7/0045* (2013.01); *G03F 7/0046* (2013.01); *G03F 7/2037* (2013.01); *G03F 7/2059* (2013.01); *C07C 2601/02* (2017.05); *C07C 2601/04* (2017.05); *C07C 2601/08* (2017.05); *C07C 2601/14* (2017.05); *C07C 2601/18* (2017.05); *C07C 2601/20* (2017.05); *C07C 2602/08* (2017.05); *C07C 2602/10* (2017.05); *C07C 2602/24* (2017.05); *C07C 2602/28* (2017.05); *C07C 2602/42* (2017.05); *C07C 2603/16* (2017.05); *C07C 2603/18* (2017.05); *C07C 2603/24* (2017.05); *C07C 2603/50* (2017.05); *C07C 2603/68* (2017.05); *C07C 2603/74* (2017.05); *C07C 2603/86* (2017.05); *C07J 43/003* (2013.01)

(58) Field of Classification Search
CPC ........ G03F 7/0045; G03F 7/0392; G03F 7/38; G03F 7/0046; G03F 7/0397; G03F 7/2037; C07C 69/74; C07C 69/78; C07C 69/753; C07C 69/757; C07C 69/95; C07C 205/06; C07C 205/11; C07C 303/32; C07C 309/04; C07C 309/06; C07C 309/12; C07C 309/20; C07C 309/24; C08F 228/02
USPC .............. 430/270.1, 326, 921; 526/286, 287, 526/292.95; 560/20, 21, 23, 51, 100, 560/103, 111, 117, 119, 120, 125, 126, 560/129, 195, 197, 205, 222, 223; 562/100, 108, 109, 113
See application file for complete search history.

(56) References Cited

U.S. PATENT DOCUMENTS 8,105,748 B2 *  1/2012  Ohashi ................. C07C 309/12
                                              430/270.1
9,360,753 B2   6/2016  Hatakeyama
(Continued)

FOREIGN PATENT DOCUMENTS

JP    2006-178317 A    7/2006
JP    2010-152136 A    7/2010
(Continued)

OTHER PUBLICATIONS

Office Action dated Apr. 25, 2017, issued in counterpart Taiwanese Application No. 105133801. (3 pages).

(Continued)

*Primary Examiner* — John S Chu
(74) *Attorney, Agent, or Firm* — Westerman, Hattori, Daniels & Adrian, LLP

(57) ABSTRACT

A resist composition comprising a base resin comprising acid labile group-containing recurring units and preferably acid generator-containing recurring units, and a sodium, magnesium, potassium, calcium, rubidium, strontium, yttrium, cesium, barium or cerium salt of α-fluorinated sulfonic acid bonded to an alkyl, alkenyl, alkynyl or aryl group exhibits a high resolution and sensitivity and forms a pattern of satisfactory profile with minimal LWR after exposure and development.

12 Claims, 2 Drawing Sheets

(51) Int. Cl.

| | | |
|---|---|---|
| *G03F 7/20* | (2006.01) | |
| *C07C 309/04* | (2006.01) | |
| *C07C 309/24* | (2006.01) | |
| *C07C 309/06* | (2006.01) | |
| *C07C 309/20* | (2006.01) | |
| *C07C 309/73* | (2006.01) | |
| *C07J 43/00* | (2006.01) | |

(56) References Cited

U.S. PATENT DOCUMENTS

| | | |
|---|---|---|
| 2006/0228648 A1 | 10/2006 | Ohsawa et al. |
| 2008/0318160 A1 | 12/2008 | Ohsawa et al. |
| 2015/0079508 A1* | 3/2015 | Ito .......................... G03F 7/004 430/18 |

FOREIGN PATENT DOCUMENTS

| | | |
|---|---|---|
| JP | 2013-25211 A | 2/2013 |
| TW | 200707101 A | 2/2007 |

OTHER PUBLICATIONS

Guerrero et al., A New Generation of Bottom Anti-Reflective Coatings (BARCs): Photodefinable BARCs, SPIE vol. 5039 (2003) (7 pages).
Kishikawa et al., Assessment of Trade-off between Resist Resolution and Sensitivity for Optimization of Hyper-NA Immersion Lithography, SPIE vol. 6520 (2007) (9 pages).

* cited by examiner

RESIST COMPOSITION, PATTERNING PROCESS, AND BARIUM, CESIUM AND CERIUM SALTS

CROSS-REFERENCE TO RELATED APPLICATION

This non-provisional application claims priority under 35 U.S.C. § 119(a) on Patent Application Nos. 2015-208583, 2016-134659 and 2016-181229 filed in Japan on Oct. 23, 2015, Jul. 7, 2016 and Sep. 16, 2016, respectively, the entire contents of which are hereby incorporated by reference.

TECHNICAL FIELD

This invention relates to a resist composition, a patterning process using the same, and barium, cesium and cerium salts.

BACKGROUND ART

To meet the demand for higher integration density and operating speed of LSIs, the effort to reduce the pattern rule is in rapid progress. The wide-spreading flash memory market and the demand for increased storage capacities drive forward the miniaturization technology. As the advanced miniaturization technology, manufacturing of microelectronic devices at the 65-nm node by the ArF lithography has been implemented in a mass scale. Manufacturing of 45-nm node devices by the next generation ArF immersion lithography is approaching to the verge of high-volume application. The candidates for the next generation 32-nm node include ultra-high NA lens immersion lithography using a liquid having a higher refractive index than water in combination with a high refractive index lens and a high refractive index resist film, EUV lithography of 13.5 nm wavelength, and double patterning version of the ArF lithography, on which active research efforts have been made.

The current technology is approaching to the processing size which is reduced below 50 nm as minimum line width. When the processing size is so reduced, the thickness of resist film must be reduced below 100 nm, depending on the surface material of the substrate to be processed, because of such factors as the structural strength to maintain the pattern against the surface tension of developer and the adhesion strength to the substrate. On use of prior art chemically amplified resist materials intended to form high-resolution resist film, for example, based on a base resin having an acetal protective group, no significant degradation of line edge roughness (LER) does occur with a resist film having a thickness of 150 nm, but LER is substantially exacerbated when the film thickness is reduced below 100 nm.

With respect to high-energy radiation of very short wavelength such as EB or x-ray, hydrocarbons used in resist materials have little absorption. Then hydrocarbon (typically polyhydroxystyrene) base resist materials are under consideration. Resist materials for EB lithography are practically used in the mask image writing application. Recently, the mask manufacturing technology becomes of greater interest. Reduction projection exposure systems or steppers have been used since the time when the exposure light was g-line. While their demagnification factor was ⅕, a factor of ¼ is now used as a result of chip size enlargement and projection lens diameter increase. It becomes of concern that a dimensional error of a mask has an impact on the dimensional variation of a pattern on wafer. It is pointed out that as the pattern feature is reduced, the value of a dimensional variation on the wafer becomes greater than the value of a dimensional error of the mask. This is evaluated by a mask error enhancement factor (MEEF) which is a dimensional variation on wafer divided by a dimensional error of mask. Patterns on the order of 45 nm often show an MEEF in excess of 4. In a situation including a demagnification factor of ¼ and a MEEF of 4, the mask manufacture needs an accuracy substantially equivalent to that for equi-magnification masks.

The exposure system for mask manufacturing made a transition from the laser beam exposure system to the EB exposure system to increase the accuracy of line width. Since a further size reduction becomes possible by increasing the accelerating voltage of the electron gun in the EB exposure system, the accelerating voltage increased from 10 kV to 30 kV and reached 50 kV in the current mainstream system, with a voltage of 100 kV being under investigation.

As the accelerating voltage increases, a lowering of sensitivity of resist film becomes of concern. As the accelerating voltage increases, the influence of forward scattering in a resist film becomes so reduced that the contrast of electron image writing energy is improved to ameliorate resolution and dimensional control whereas electrons can pass straightforward through the resist film so that the resist film lowers its sensitivity. Since the mask exposure tool is designed for exposure by direct continuous writing, a lowering of sensitivity of resist film leads to an undesirably reduced throughput. Due to a need for higher sensitivity, chemically amplified resist compositions are contemplated.

As the feature size is reduced, image blurs due to acid diffusion become a problem (see Non-Patent Document 1). To insure resolution for fine patterns with a size of 45 nm et seq., not only an improvement in dissolution contrast is requisite, but control of acid diffusion is also important (see Non-Patent Document 2). Since chemically amplified resist compositions are designed such that sensitivity and contrast are enhanced by acid diffusion, an attempt to minimize acid diffusion by reducing the temperature and/or time of post-exposure bake (PEB) fails, resulting in drastic reductions of sensitivity and contrast.

Addition of an acid generator capable of generating a bulky acid is effective for suppressing acid diffusion. It is then proposed to incorporate in a polymer recurring units derived from an onium salt having a polymerizable unsaturated bond serving as acid generator. Sulfonium and iodonium salts having a polymerizable unsaturated bond capable of generating a sulfonic acid are proposed in Patent Document 1 and other documents. Patent Document 1 also discloses a sulfonium or iodonium salt having sulfonic acid directly attached to the backbone.

It was avoided to use metal-containing materials as the lithography resist material for the semiconductor device fabrication because of a possible malfunction of semiconductor devices. However, it is known in the application other than the semiconductor, for example, as the resist material for forming color filters for LCD, to use a metal-containing (meth)acrylate as a copolymerizable monomer.

Patent Document 2 discloses EB resist and antistatic film having alkali metal and alkaline earth metal salts added thereto. These salts improve the sensitivity on EB exposure at no sacrifice of resolution. Patent Document 3 discloses a chemically amplified resist composition having a metal salt of carboxylic acid or β-diketone added thereto. The metal salt of carboxylic acid or β-diketone functions as a quencher as it undergoes ion exchange with a sulfonic acid generated from the acid generator.

CITATION LIST

Patent Document 1: JP-A 2006-178317
Patent Document 2: JP-A 2010-152136
Patent Document 3: JP-A 2013-025211 (U.S. Pat. No. 9,360, 753)
Non-Patent Document 1: SPIE Vol. 5039 p1 (2003)
Non-Patent Document 2: SPIE Vol. 6520 p65203L-1 (2007)

DISCLOSURE OF INVENTION

While the miniaturization of the pattern rule is in progress to meet the demand for higher integration density and operating speed of LSIs as alluded to previously, there is a need for a resist composition which has a high sensitivity despite a high resolution and forms a pattern of satisfactory profile and minimal roughness (LWR) after exposure and development.

An object of the invention is to provide a resist composition which has both high resolution and sensitivity and forms a pattern with a satisfactory profile and minimal LWR after exposure and development, a patterning process using the resist composition, and novel barium, cesium and cerium salts useful in the resist composition.

The inventors have found that a resist composition, typically chemically amplified positive resist composition, comprising a base resin comprising recurring units having an acid labile group and a sodium, magnesium, potassium, calcium, rubidium, strontium, yttrium, cesium, barium or cerium salt of α-fluorinated sulfonic acid bonded to a $C_5$-$C_{30}$ straight, branched or cyclic alkyl, alkenyl or alkynyl group or $C_6$-$C_{20}$ aryl group exhibits a high sensitivity, forms a pattern of satisfactory profile with minimal LER after exposure and development, and is effective for preventing electrostatic charges during EB image writing. The resist composition is thus suited as the micropatterning material for the fabrication of VLSIs and photomasks.

In one aspect, the invention provides a resist composition comprising a base resin comprising recurring units containing an acid labile group and a salt having the formula (1).

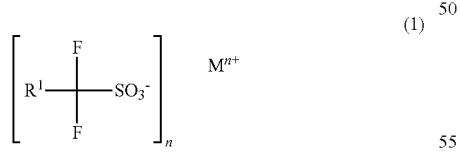
(1)

Herein $R^1$ is a $C_5$-$C_{30}$ straight, branched or cyclic alkyl, alkenyl or alkynyl group or $C_6$-$C_{20}$ aryl group, which may contain halogen, ether, thiol, ester, carbonate, carbonyl, amide, amino, azide, carbamate, nitro, cyano, hydroxyl, carboxyl, sulfo, sulfonic acid ester, sultone moiety, lactone ring or lactam ring, $M^{n+}$ is a sodium, magnesium, potassium, calcium, rubidium, strontium, yttrium, cesium, barium or cerium ion, and n is an integer of 1 to 3.

In a preferred embodiment, the recurring units containing an acid labile group have the formula (a1) or (a2).

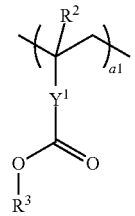
(a1)

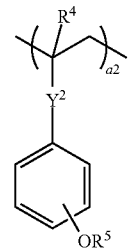
(a2)

Herein $R^2$ and $R^4$ are each independently hydrogen or methyl, $R^3$ and $R^5$ each are an acid labile group, $Y^1$ is a single bond, a $C_1$-$C_{12}$ linking group having at least one of ester moiety, lactone ring, phenylene moiety and naphthylene moiety, a phenylene group, or a naphthylene group, $Y^2$ is a single bond, ester group or amide group, a1 and a2 are numbers in the range: $0 \le a1 \le 0.9$, $0 \le a2 \le 0.9$, and $0 < a1+a2 < 1$.

In a preferred embodiment, the base resin further comprises recurring units of at least one type selected from the formulae (b1), (b2) and (b3).

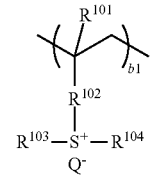
(b1)

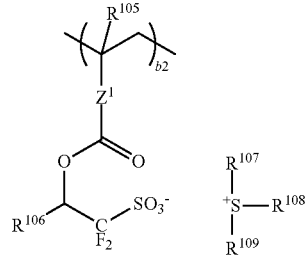
(b2)

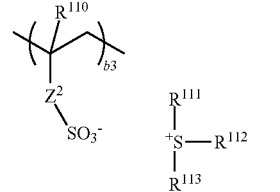
(b3)

Herein $R^{101}$, $R^{105}$, and $R^{110}$ each are hydrogen or methyl, $R^{102}$ is a single bond, phenylene, —O—$R^{114}$—, or —C(=O)—Y—$R^{114}$—, Y is —O— or —NH—, $R^{114}$ is a straight, branched or cyclic $C_1$-$C_6$ alkylene group, phenylene group or straight, branched or cyclic $C_3$-$C_{10}$ alkenylene group, which may contain a carbonyl, ester, ether or hydroxyl moiety, $R^{103}$, $R^{104}$, $R^{107}$, $R^{108}$, $R^{109}$, $R^{111}$, $R^{112}$, and $R^{113}$ are each independently a straight, branched or cyclic $C_1$-$C_{12}$ alkyl group which may contain a carbonyl, ester or ether moiety, or a $C_6$-$C_{12}$ aryl, $C_7$-$C_{20}$ aralkyl, or mercaptophenyl group which may contain a straight, branched or cyclic $C_1$-$C_{10}$ alkyl, halogen, trifluoromethyl, cyano, nitro, hydroxyl, alkoxy, alkoxycarbonyl or acyloxy moiety, $R^{106}$ is hydrogen or trifluoromethyl, $Z^1$ is a single bond or —C(=O)—$Z^3$—$R^{115}$—, $Z^2$ is a single bond, methylene, ethylene, phenylene, fluorinated phenylene, —O—$R^{115}$— or —C(=O)—$Z^3$—$R^{115}$—, $Z^3$ is —O— or —NH—, $R^{115}$ is a straight, branched or cyclic $C_1$-$C_6$ alkylene group, phenylene group or straight, branched or cyclic $C_1$-$C_6$ alkenylene group, which may contain a carbonyl, ester, ether or hydroxyl moiety, a pair of $R^{103}$ and $R^{104}$, $R^{107}$ and $R^{108}$, $R^{107}$ and $R^{109}$, $R^{108}$ and $R^{109}$, $R^{111}$ and $R^{112}$, $R^{111}$ and $R^{113}$, or $R^{112}$ and $R^{113}$ may bond directly or via a methylene moiety or ether bond to form a ring with the sulfur atom to which they are attached, $Q^-$ is a non-nucleophilic counter ion, b1, b2 and b3 are numbers in the range: 0≤b1≤0.5, 0≤b2≤0.5, 0≤b3≤0.5, and 0<b1+b2+b3≤0.5.

More preferably, the base resin comprises recurring units of the formula (b2).

The resist composition may further comprise an acid generator, the composition being a chemically amplified positive resist composition. The resist composition may further comprise an organic solvent, a dissolution inhibitor, a basic compound, and/or a surfactant.

In another aspect, the invention provides a pattern forming process comprising the steps of coating the resist composition defined above onto a substrate, baking, exposing the resulting resist film to high-energy radiation, and developing with a developer.

Preferably, the high-energy radiation is EUV of wavelength 3 to 15 nm or EB at an accelerating voltage of 1 to 150 kV.

In the step of exposing the resist film to high-energy radiation, preferably the surface of the substrate underneath the resist film is electrically charged positive.

Also contemplated herein are a barium salt having the formula (2), a cesium salt having the formula (3) and a cerium salt having the formula (4).

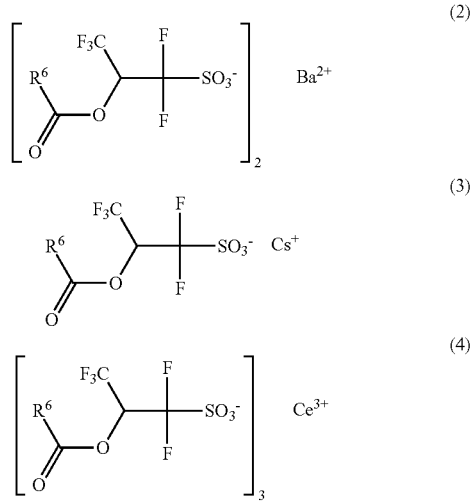

Herein $R^6$ is a $C_4$-$C_{20}$ straight, branched or cyclic alkyl, alkenyl or alkynyl group or $C_6$-$C_{20}$ aryl group, which may contain halogen, ether, thiol, ester, carbonate, carbonyl, amide, amino, azide, carbamate, nitro, cyano, hydroxyl, carboxyl, sulfo, sulfonic acid ester, sultone moiety, lactone ring or lactam ring.

Advantageous Effects of Invention

The resist composition has many advantages including a significantly high contrast of alkaline dissolution rate before and after exposure, a high sensitivity, a high resolution, exposure latitude, process adaptability, a satisfactory pattern profile after exposure, a controlled rate of acid diffusion, and a minimal LWR. The resist composition, typically chemically amplified positive resist composition is suited as the micropatterning material for VLSIs and photomasks, and the patterning material in the EB and EUV lithography. The resist composition is used not only in the lithography for semiconductor circuit formation, but also in the formation of mask circuit patterns, micro-machines, and thin-film magnetic head circuits.

DESCRIPTION OF EMBODIMENTS

Figure 1:
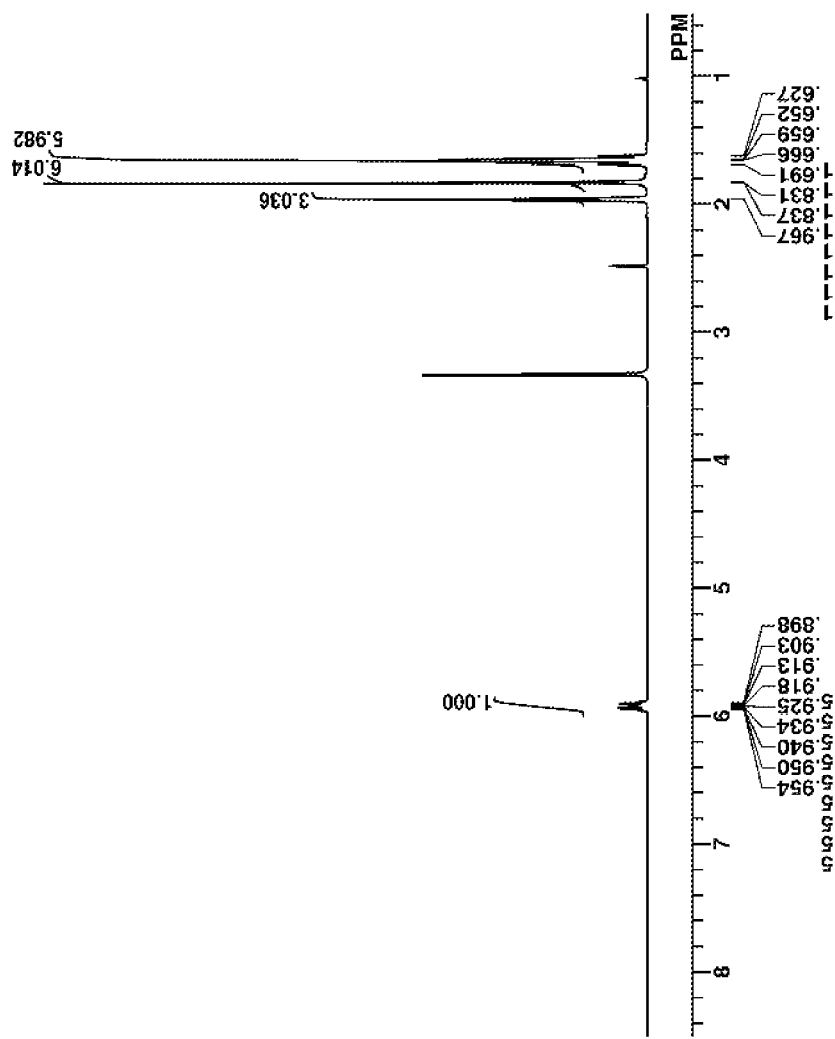
FIG. 1 is a diagram showing $^1$H-NMR spectrum of Barium Salt 1 in Synthesis Example 1.

The singular forms "a," "an" and "the" include plural referents unless the context clearly dictates otherwise. "Optional" or "optionally" means that the subsequently described event or circumstance may or may not occur, and that the description includes instances where the event occurs and instances where it does not. As used herein, the notation ($C_n$-$C_m$) means a group containing from n to m carbon atoms per group. Me stands for methyl and Ac for acetyl.

The abbreviations and acronyms have the following meaning.
UV: ultraviolet radiation
DUV: deep ultraviolet
EUV: extreme ultraviolet
EB: electron beam
Mw: weight average molecular weight
Mn: number average molecular weight
Mw/Mn: molecular weight distribution or dispersity
GPC: gel permeation chromatography
PEB: post-exposure bake
LER: line edge roughness
LWR: line width roughness Resist Composition One embodiment of the invention is a resist composition comprising a base resin comprising recurring units containing an acid labile group and a salt having the formula (1).

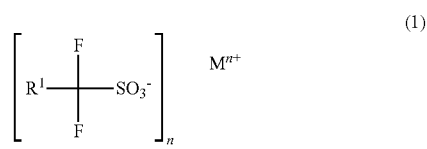

Herein $R^1$ is a $C_5$-$C_{30}$ straight, branched or cyclic alkyl, alkenyl or alkynyl group or $C_6$-$C_{20}$ aryl group, which may contain a halogen atom, ether, thiol, ester, carbonate, carbonyl, amide, amino, azide, carbamate, nitro, cyano, hydroxyl, carboxyl, sulfo, sulfonic acid ester, sultone moiety, lactone ring or lactam ring. $M^{n+}$ is a sodium, magnesium, potassium, calcium, rubidium, strontium, yttrium, cesium, barium or cerium ion, and n is an integer of 1 to 3.

The salt having formula (1) does not undergo ion exchange with the acid generated by the acid generator. If ion exchange occurs, the metal in the salt having formula (1) functions as a quencher, suggesting that the addition of the salt having formula (1) leads to a lowering of sensitivity. Any lowering of sensitivity is avoided because ion exchange does not occur. The sensitivity is rather improved since the metal emits secondary electrons.

Specifically the salt having formula (1) is a sodium, magnesium, potassium, calcium, rubidium, strontium, yttrium, cesium, barium or cerium salt as shown below.

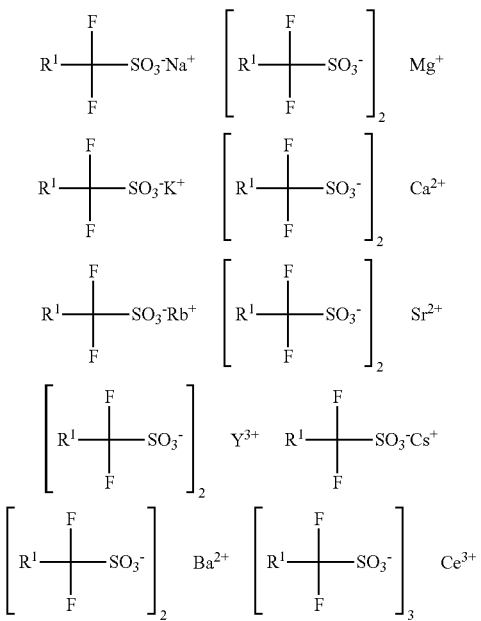

Herein $R^1$ is as defined above.

Examples of the sulfonic acid ion represented by $R^1CF_2SO_3^-$ are shown below, but not limited thereto.

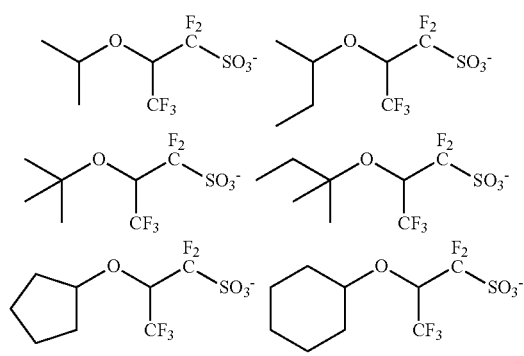

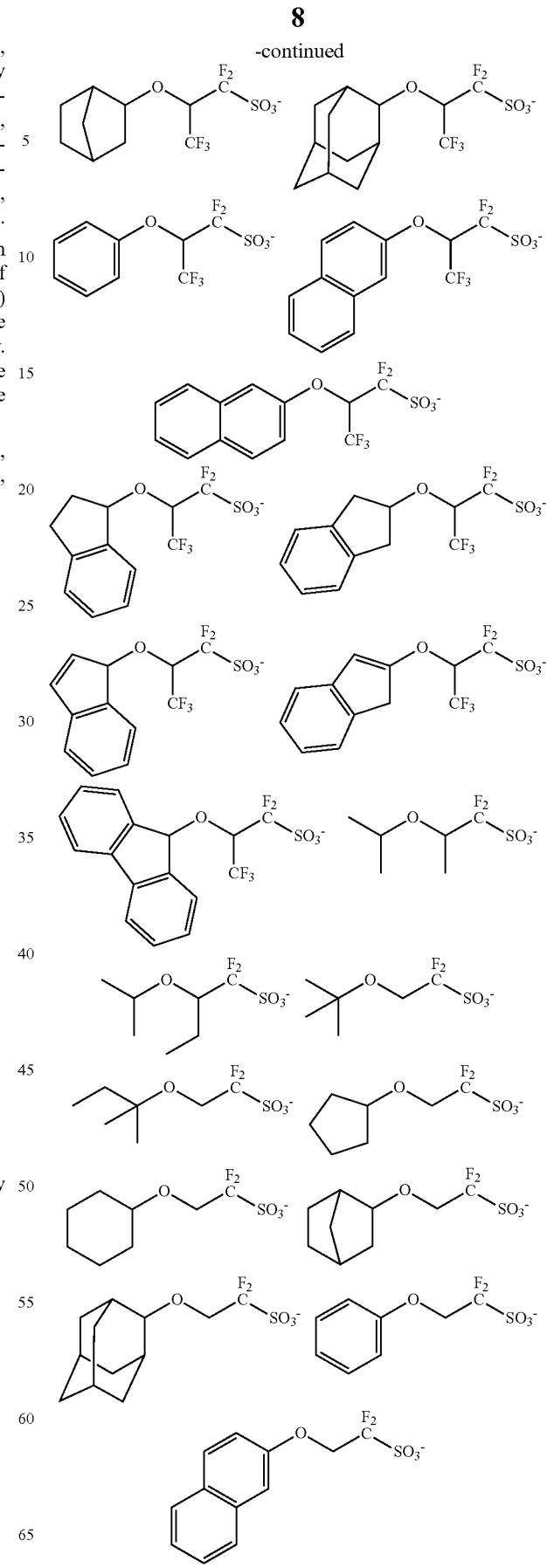

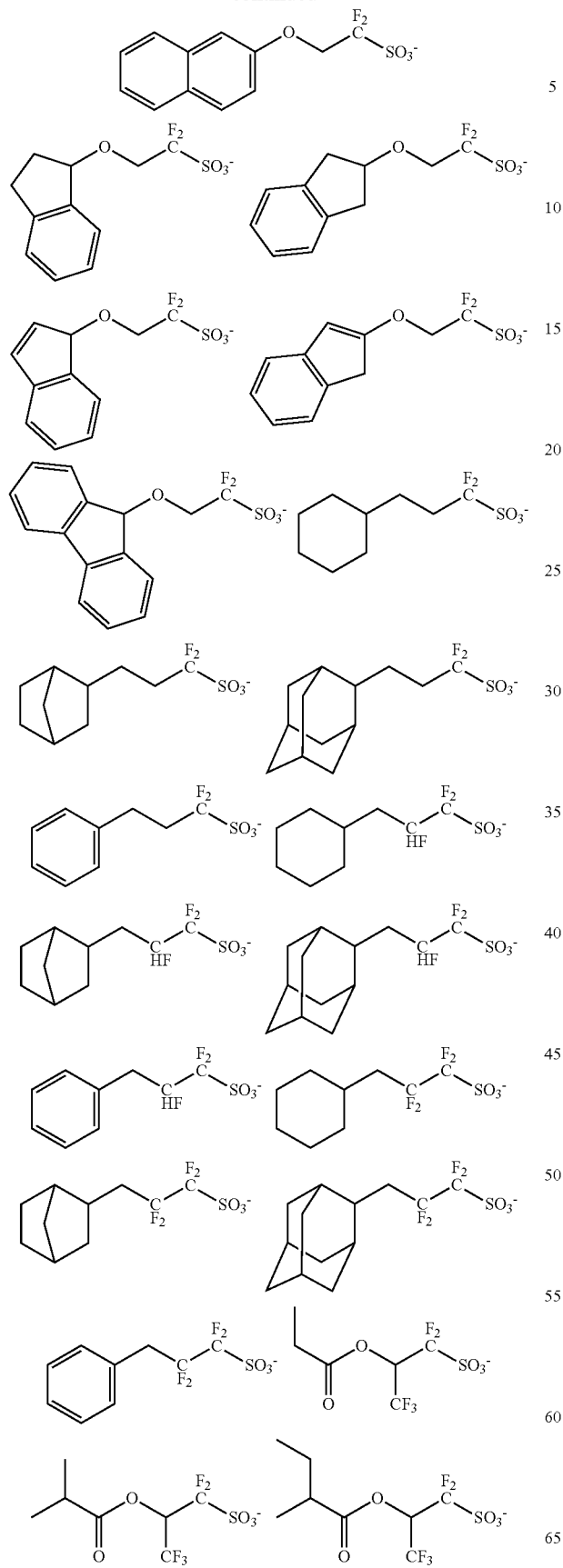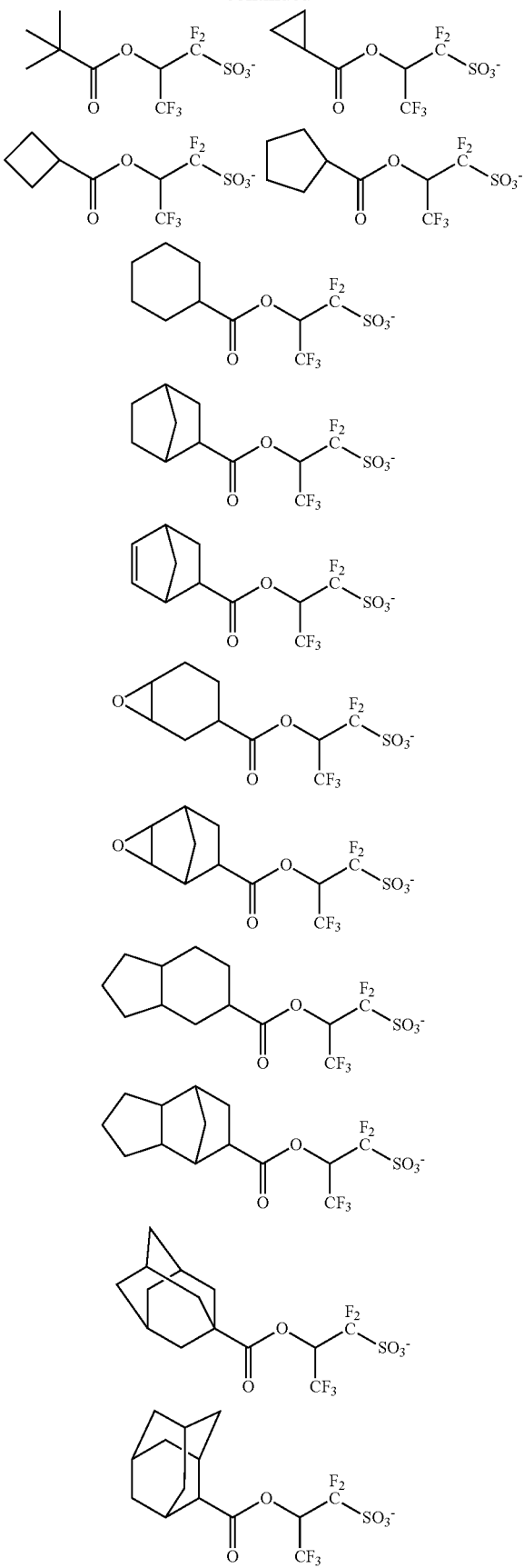

-continued
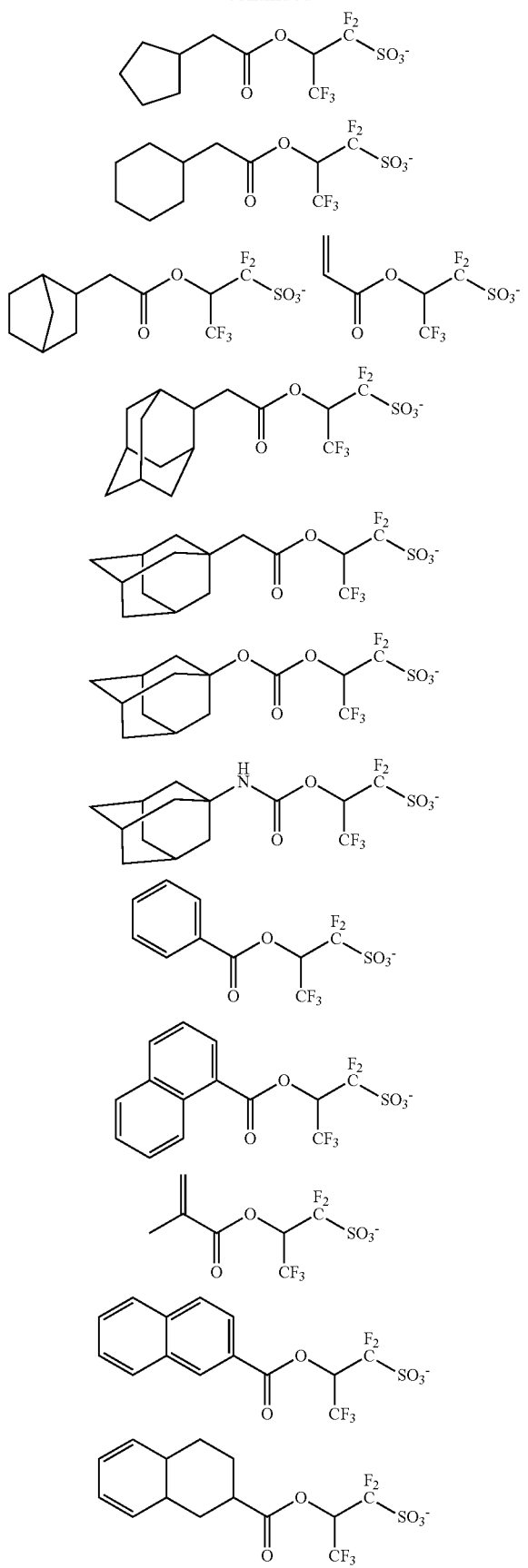
-continued
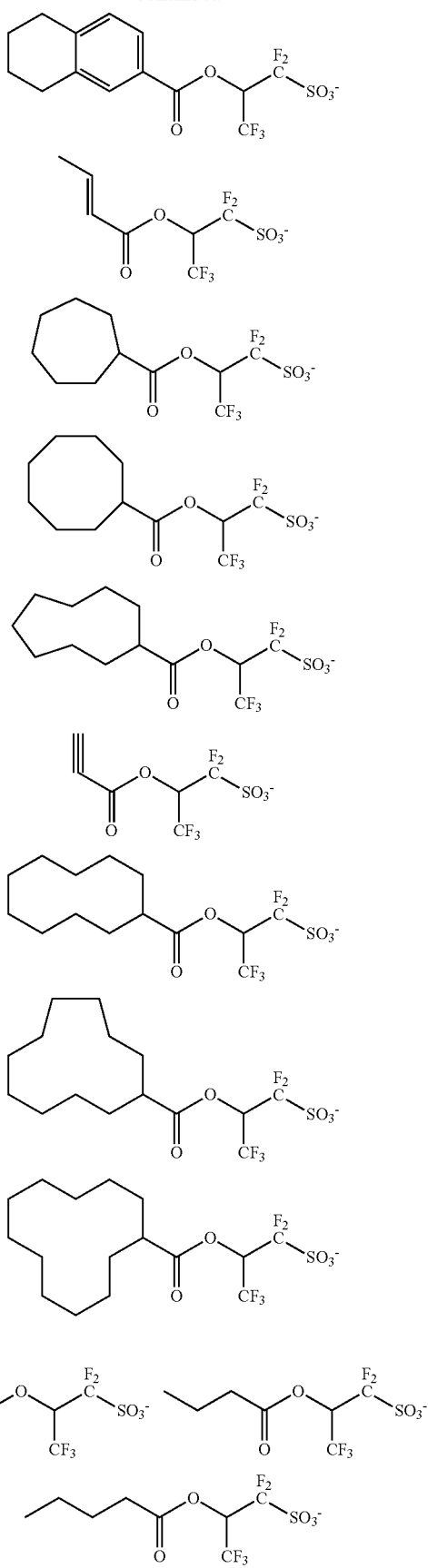

-continued
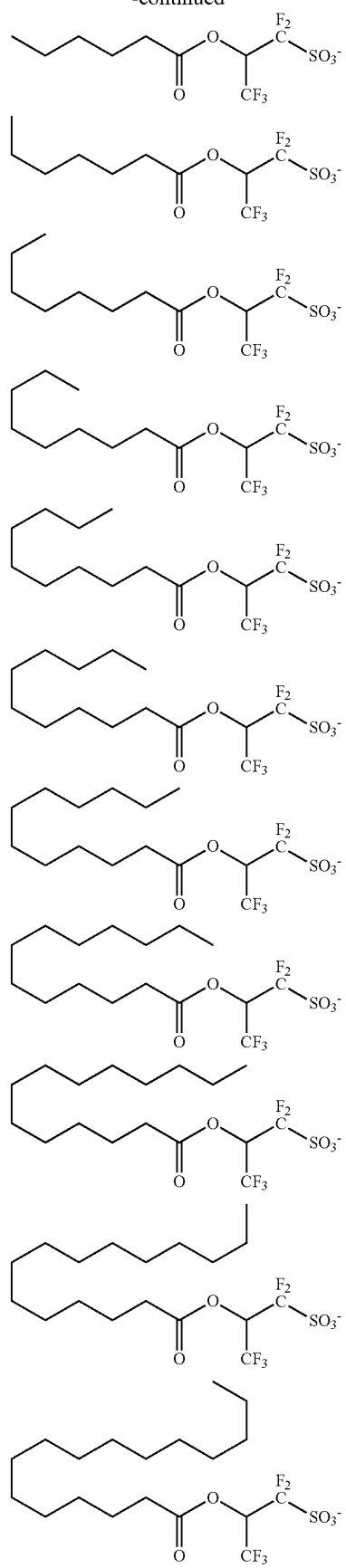
-continued
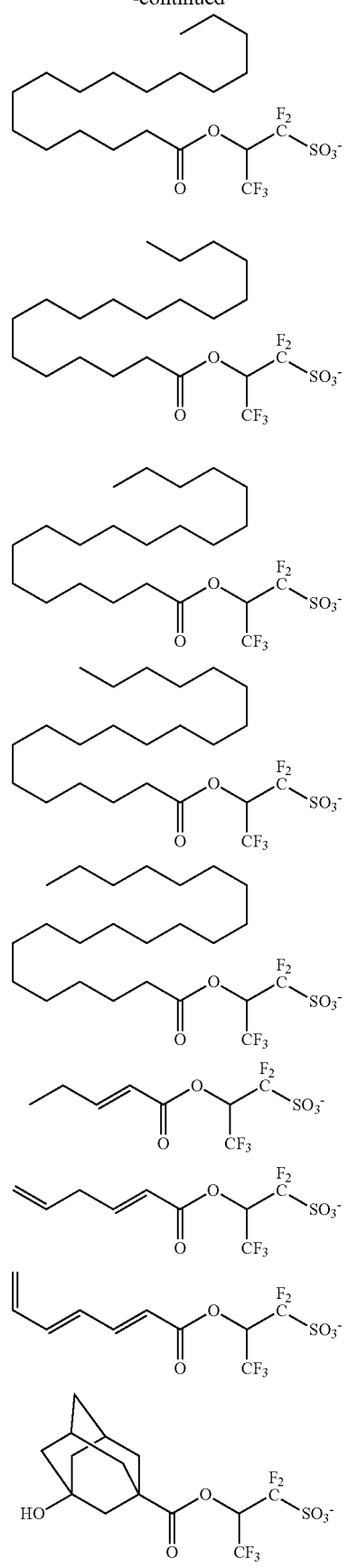

-continued
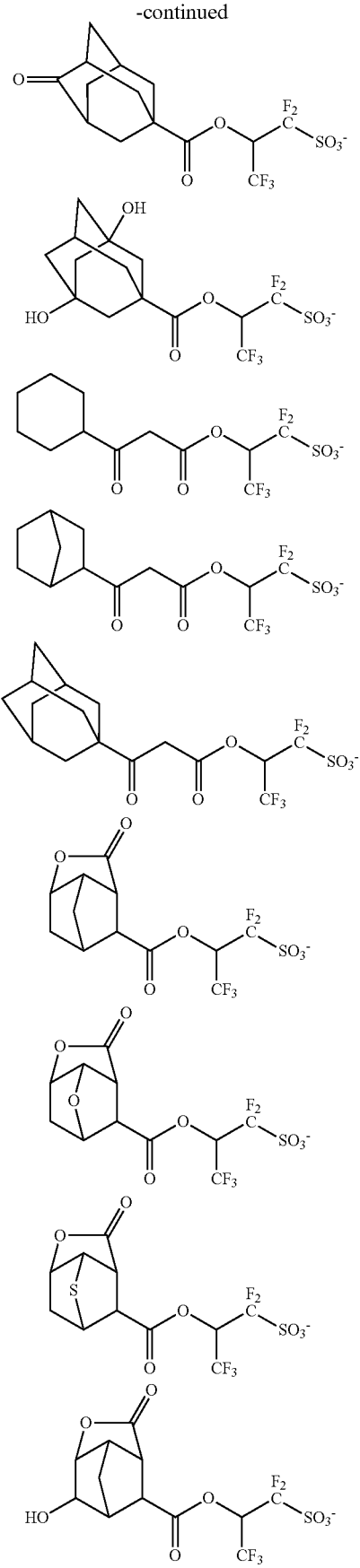
-continued
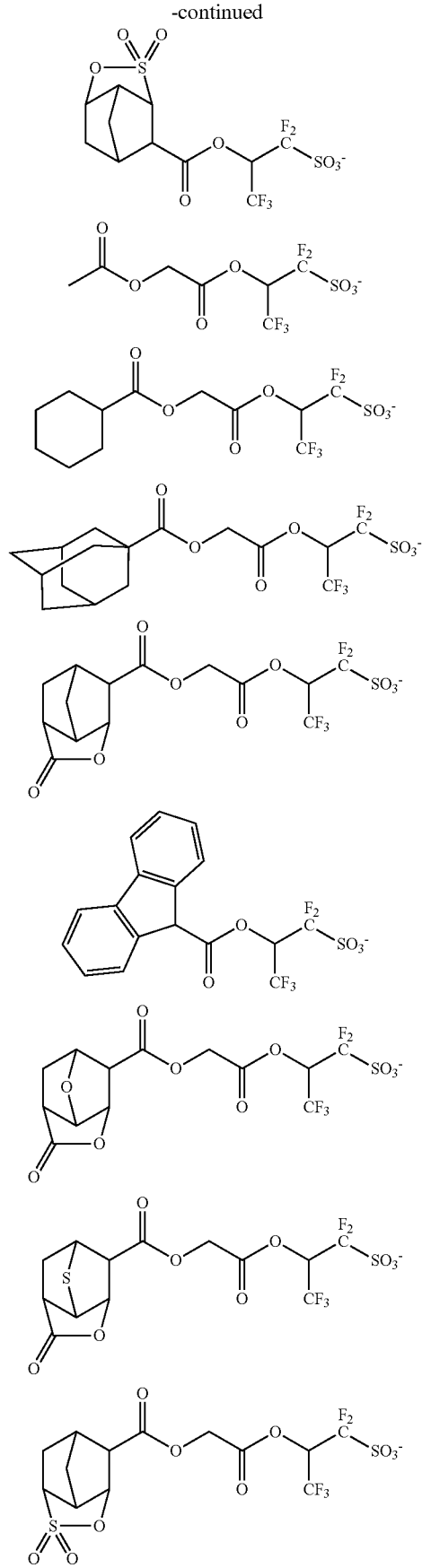

-continued
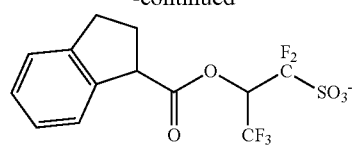
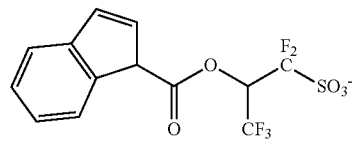
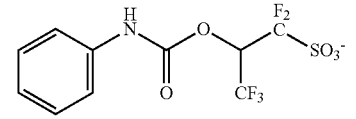
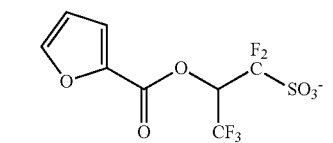
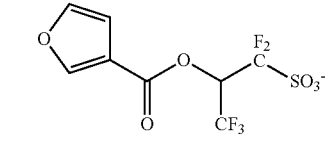
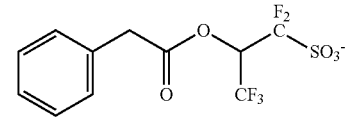
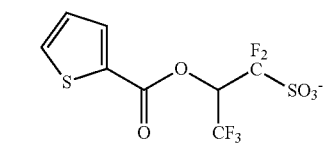
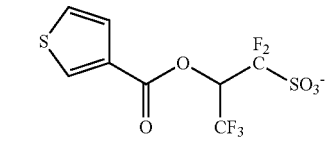
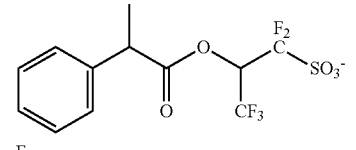
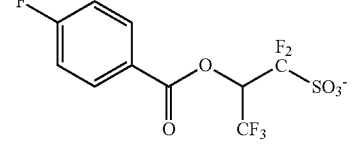
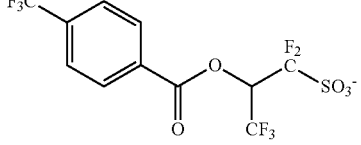
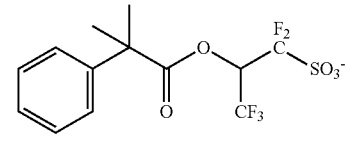
-continued
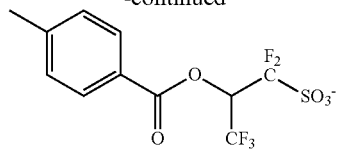
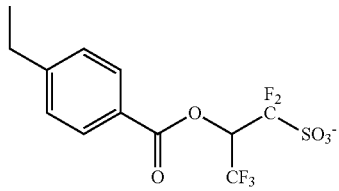
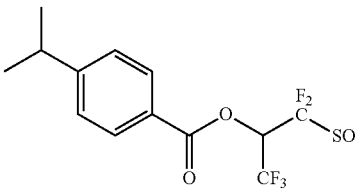
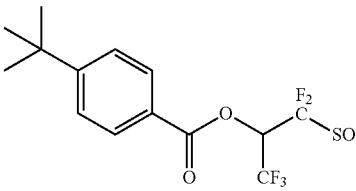
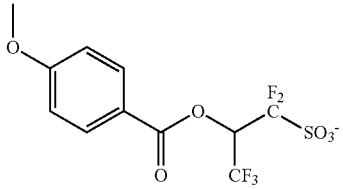
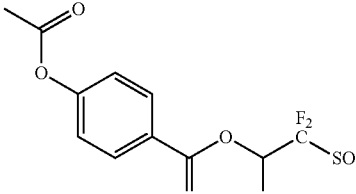
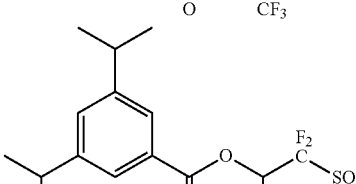
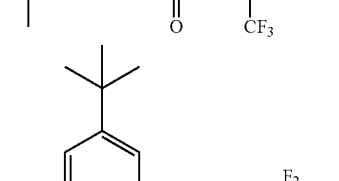
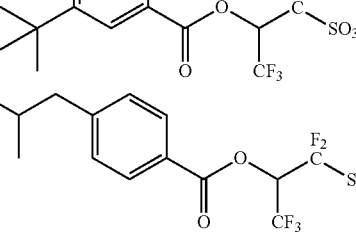

19
-continued
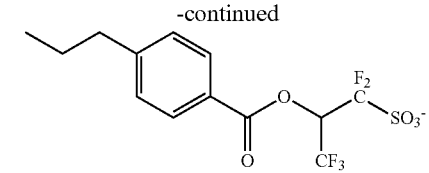
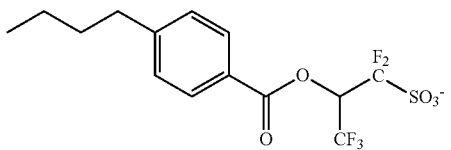
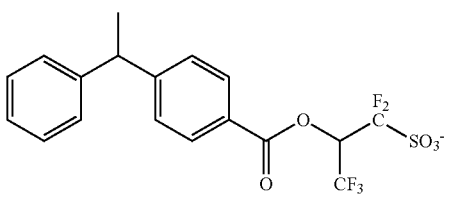
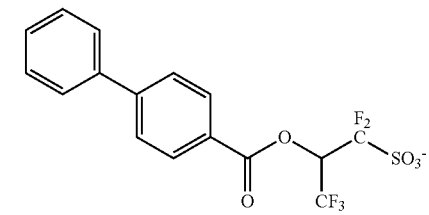
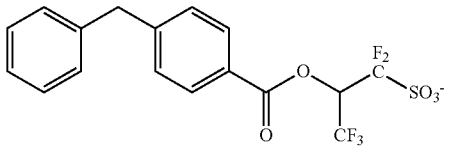
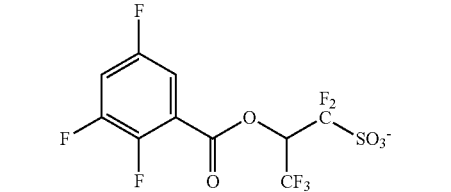
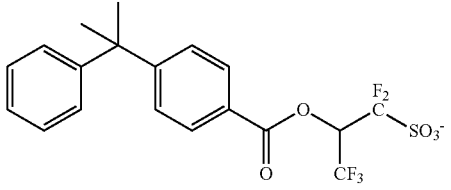
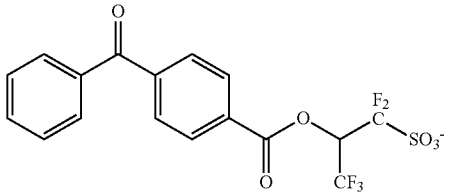
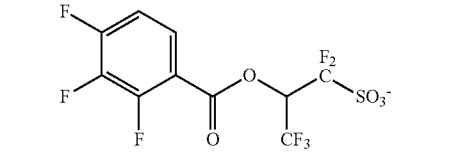
20
-continued
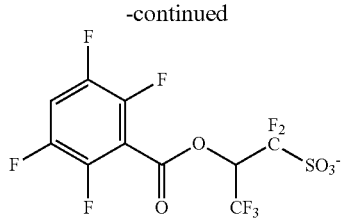
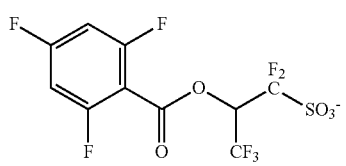
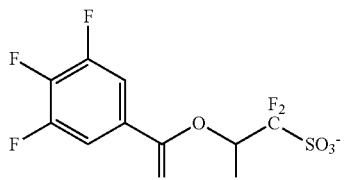
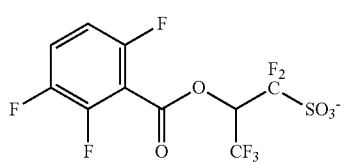
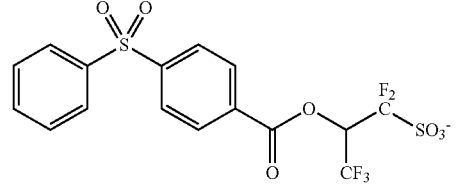
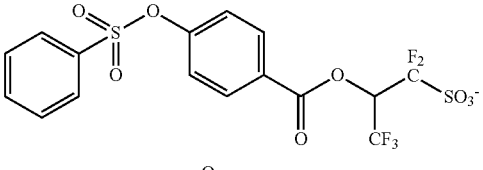
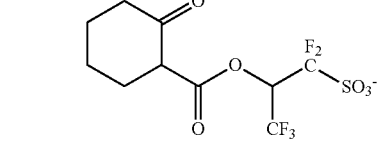
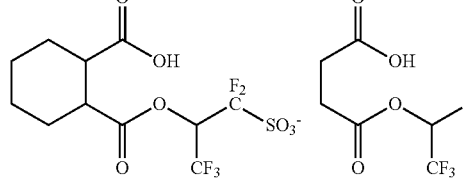
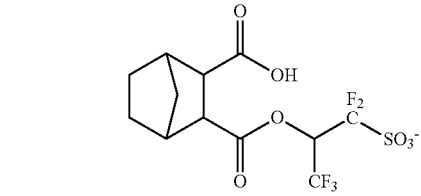

-continued
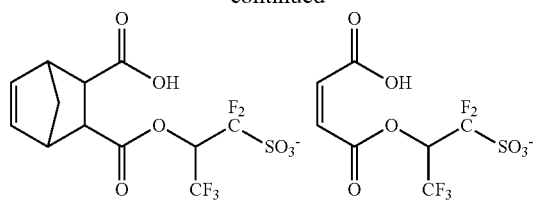
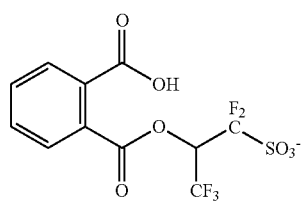
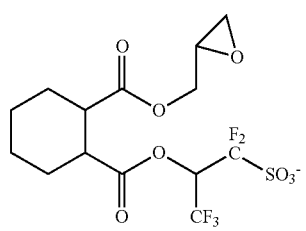
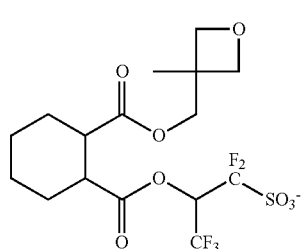
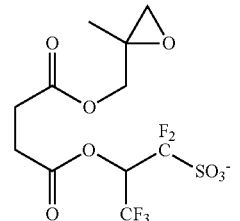
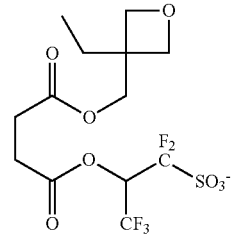
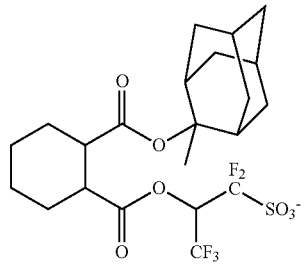
-continued
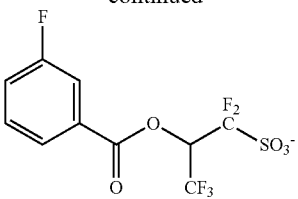
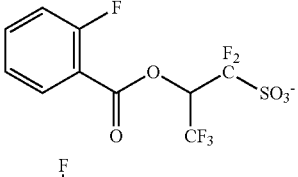
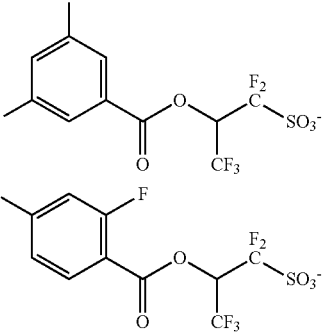
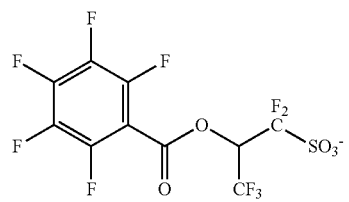
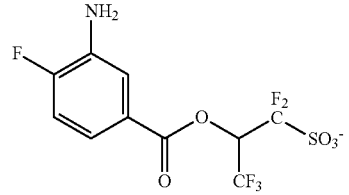
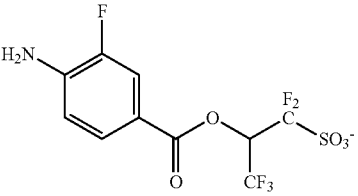
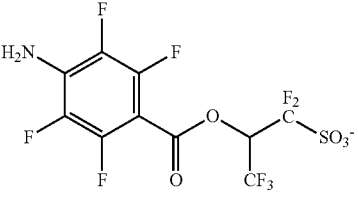
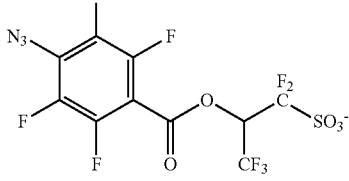

-continued
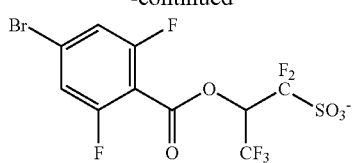
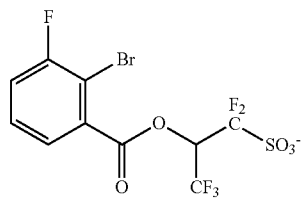
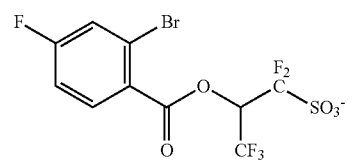
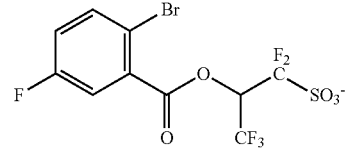
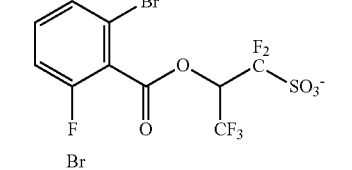
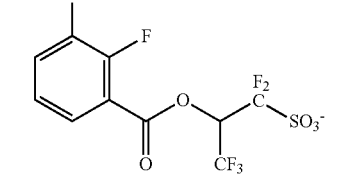
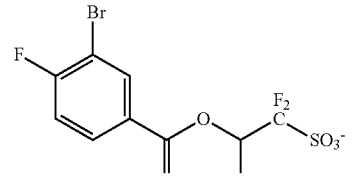
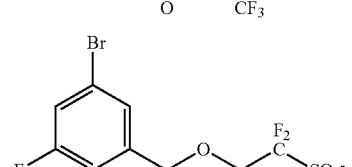
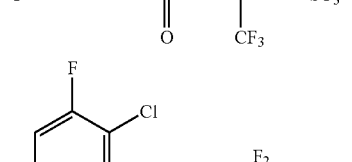
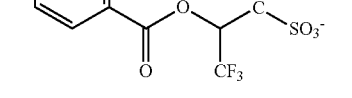
-continued
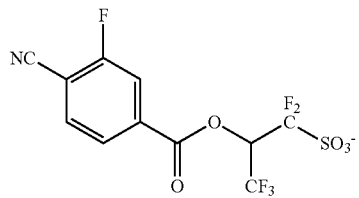
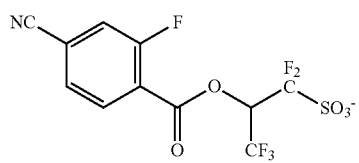
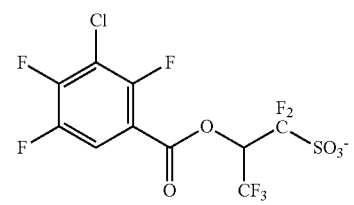
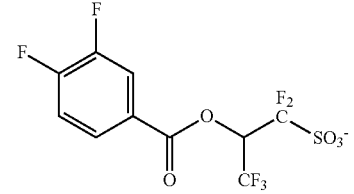
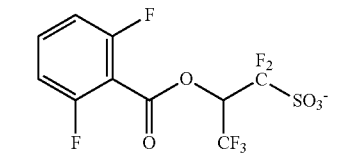
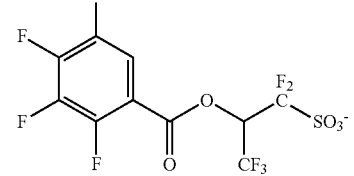
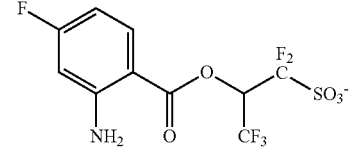
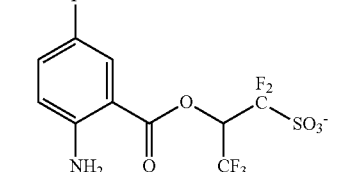
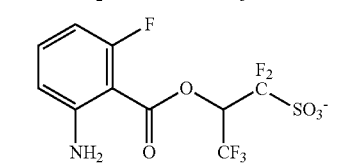

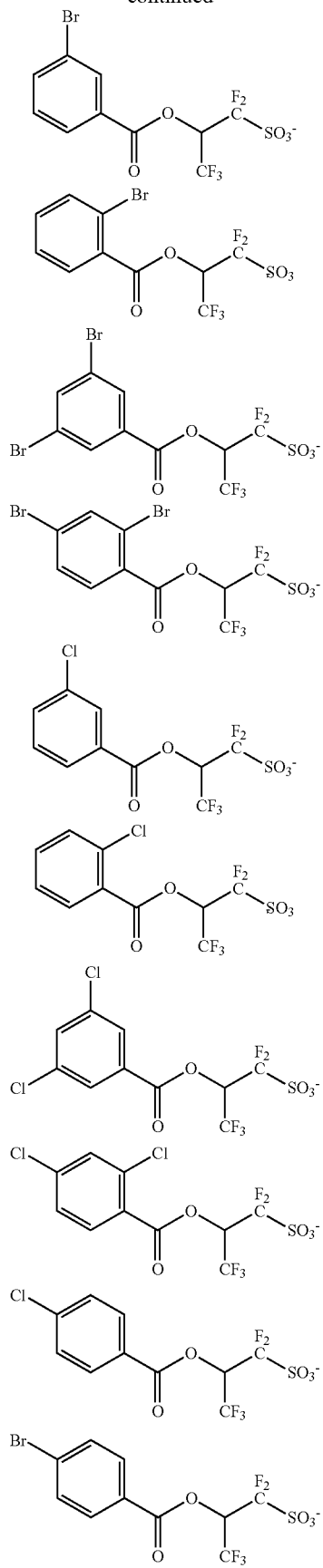
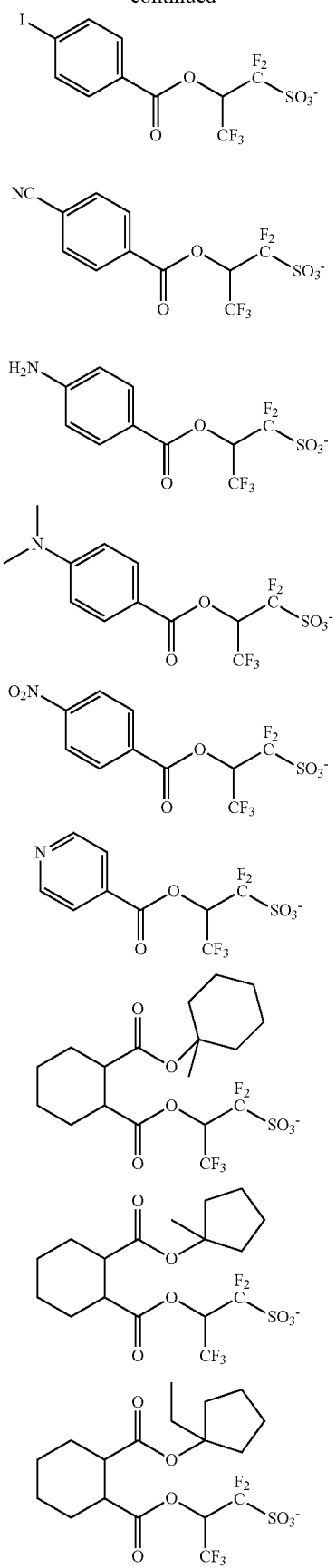

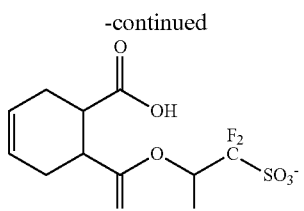
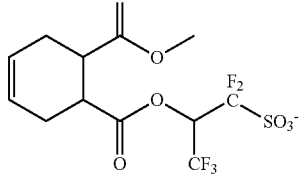
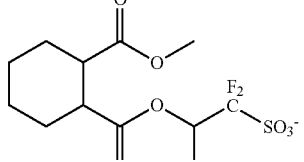
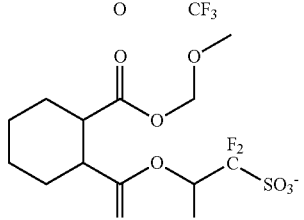
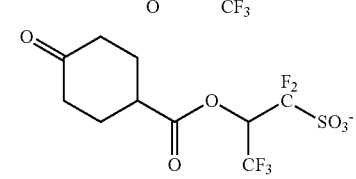
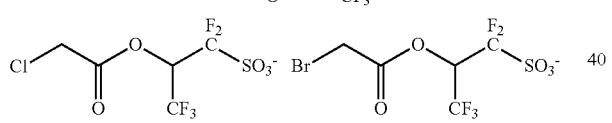
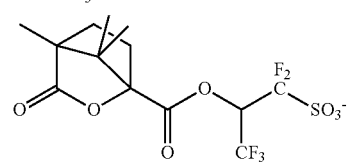
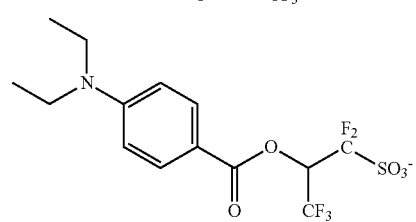
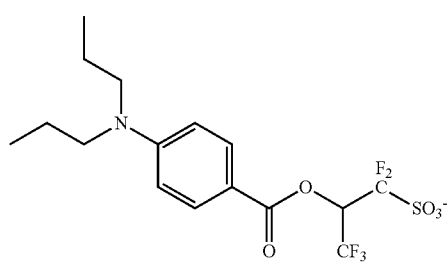
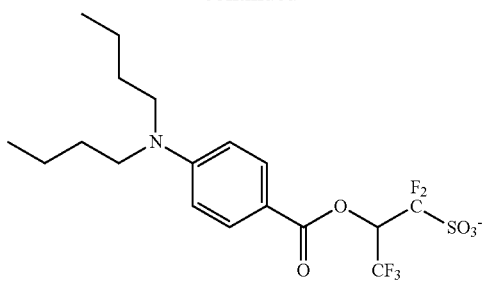
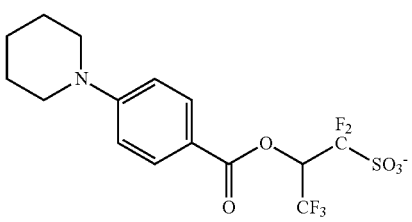
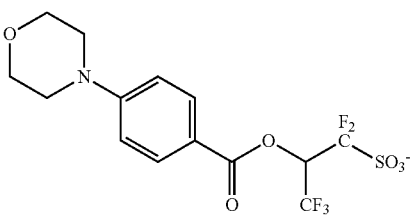
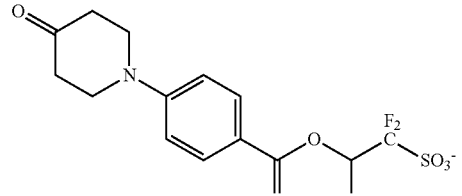
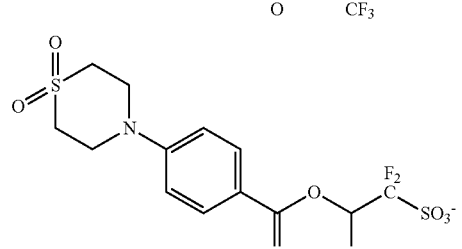
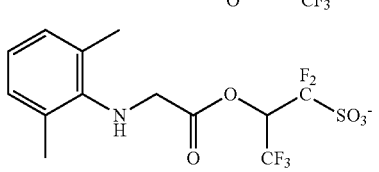
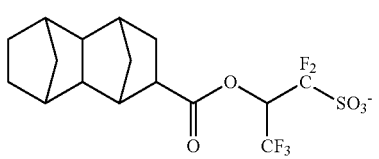
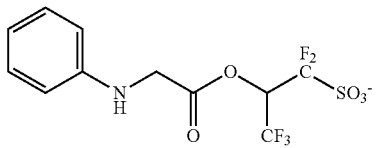

-continued
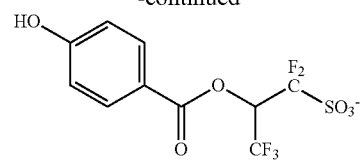
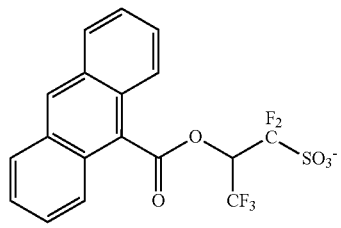
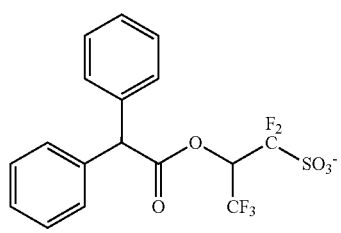
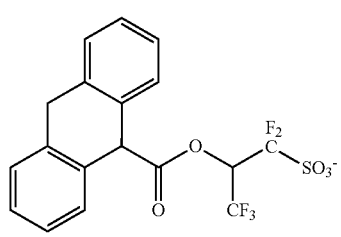
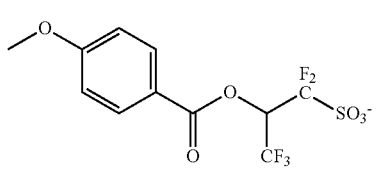
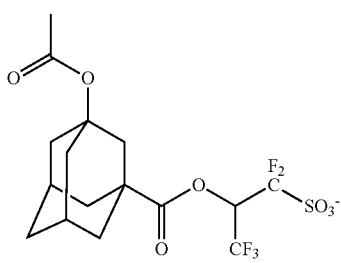
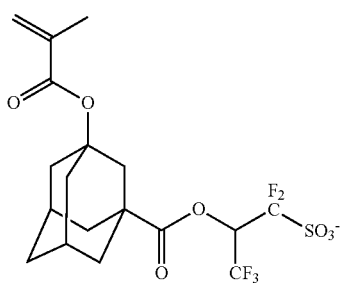
-continued
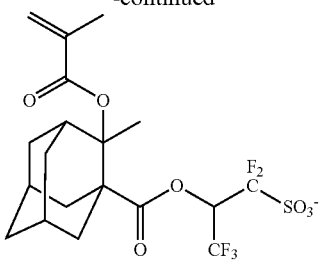
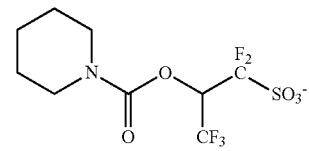
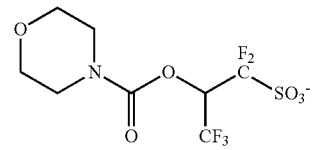
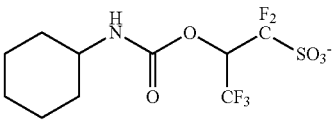
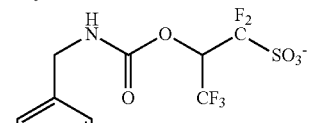
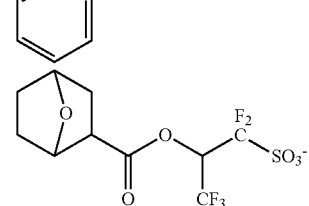
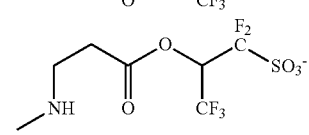
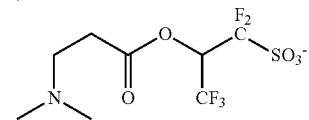
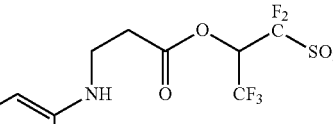
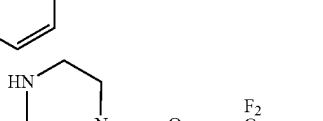
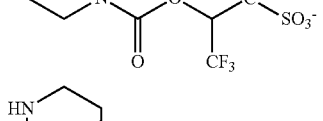

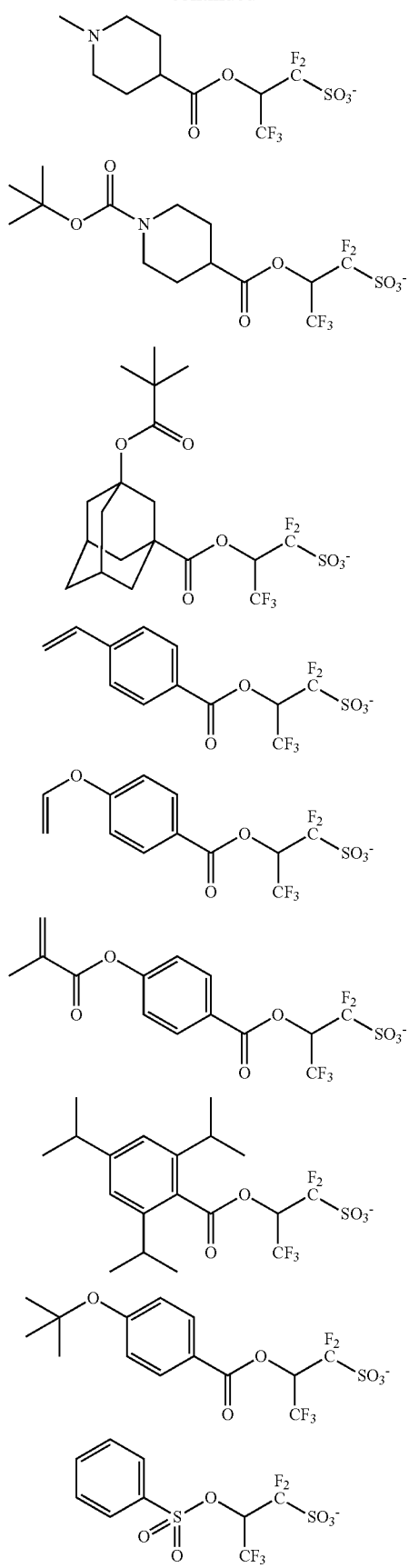
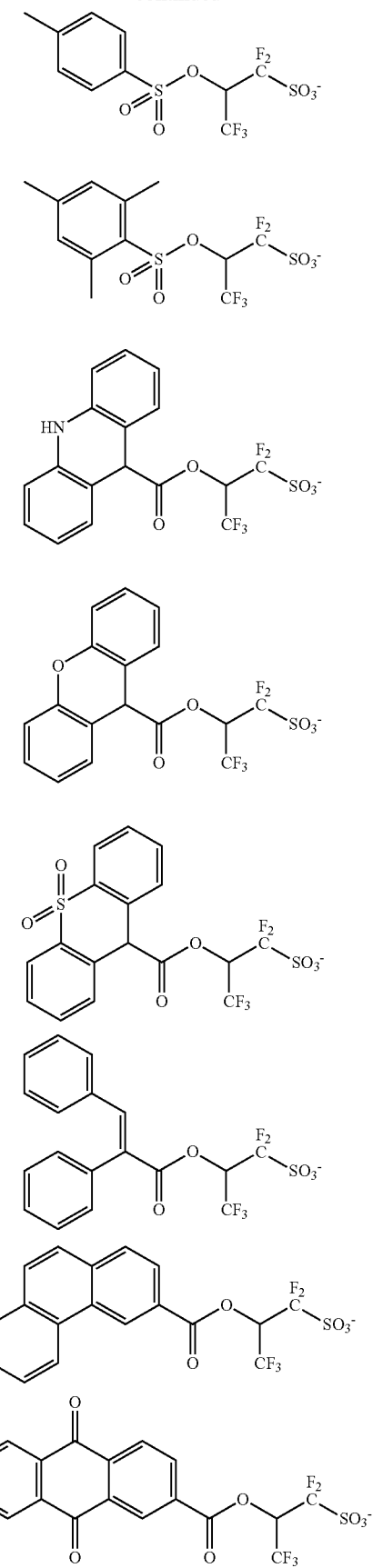

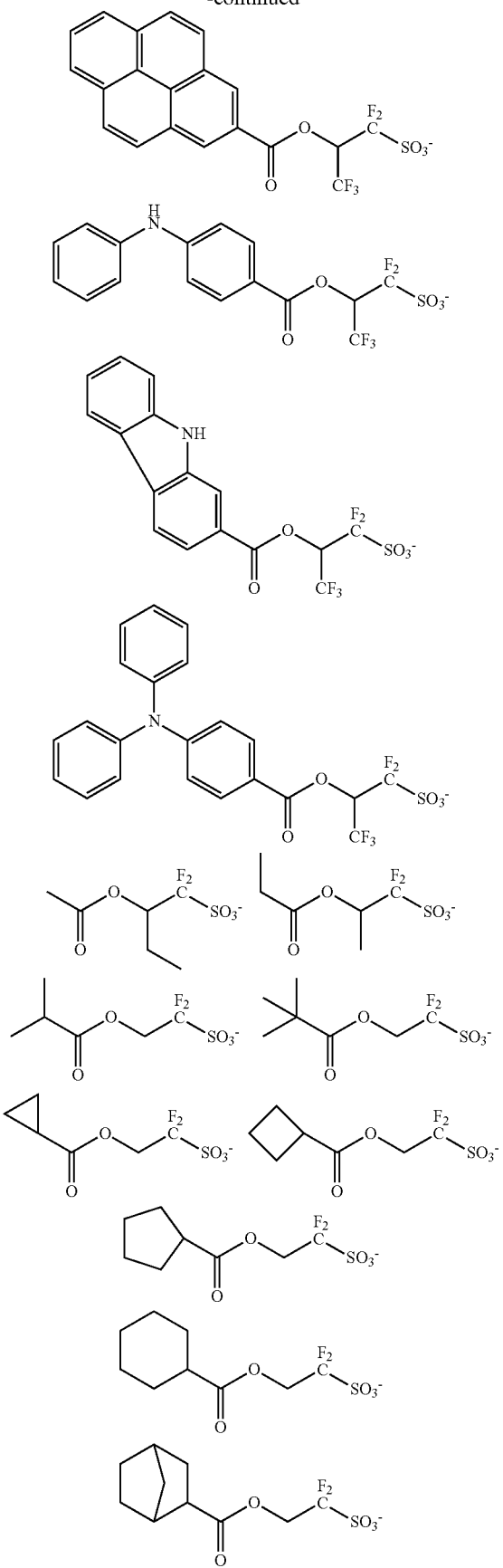
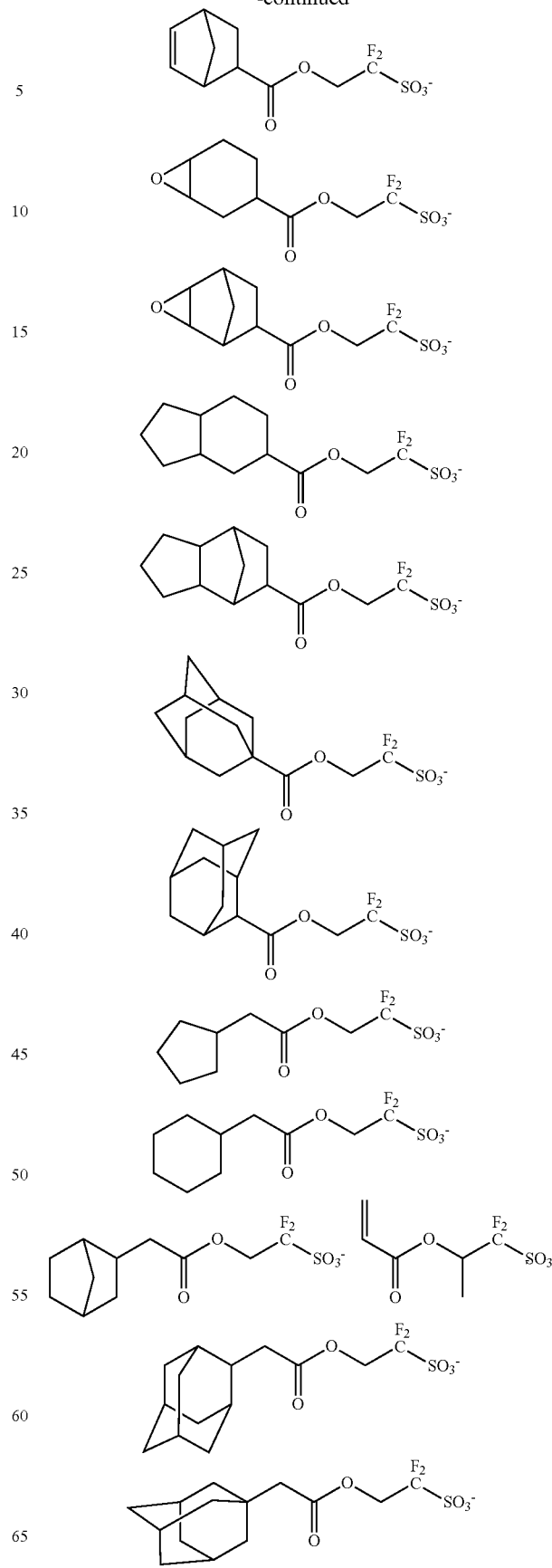

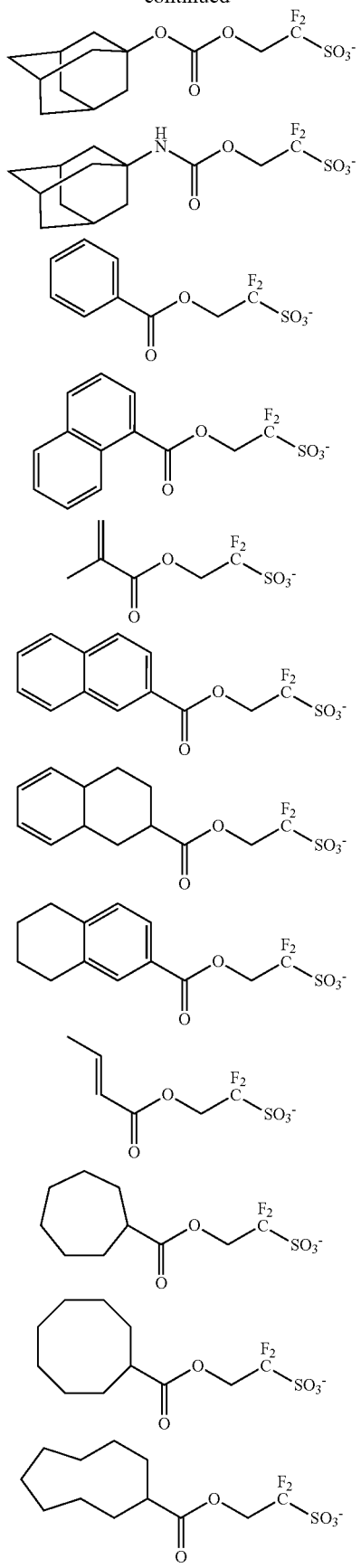
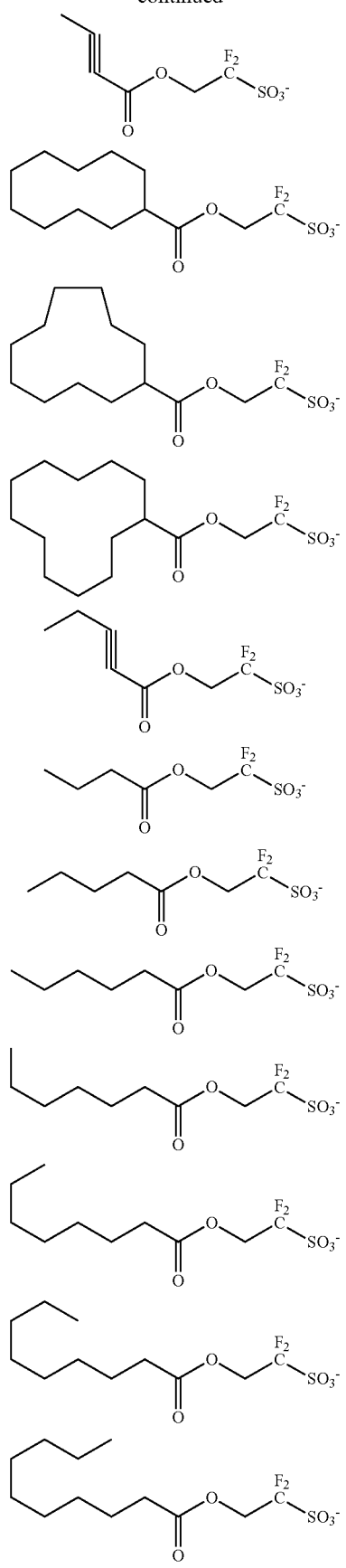

37
-continued
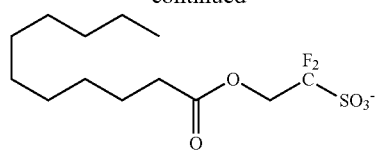
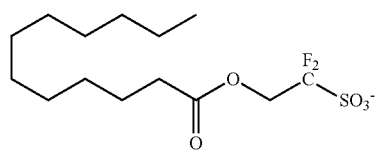
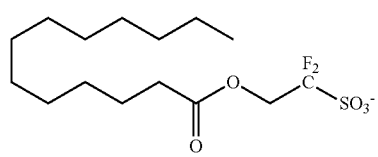
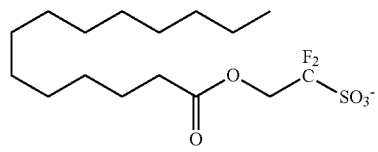
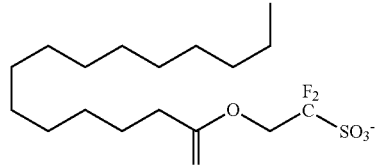
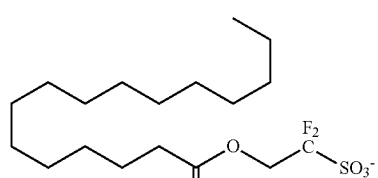
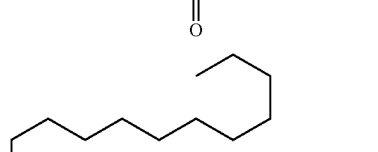
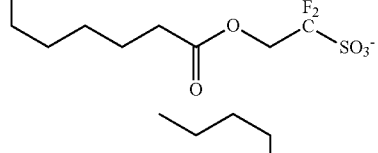
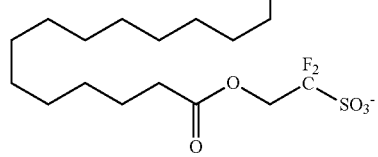
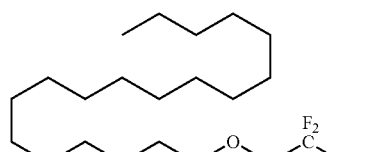
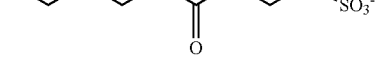
38
-continued
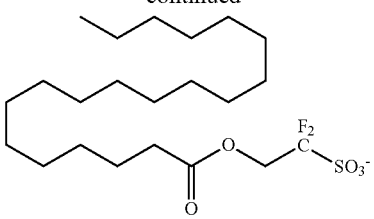
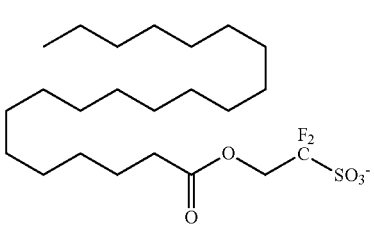
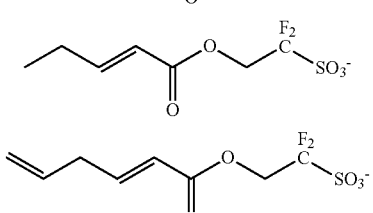
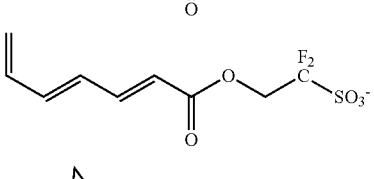
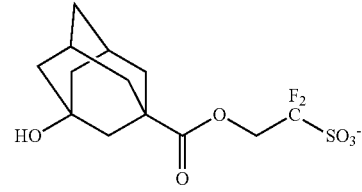
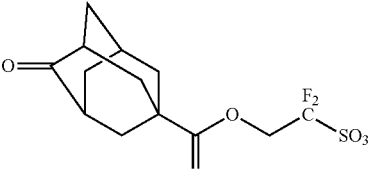
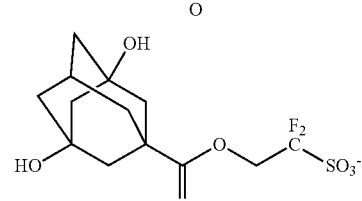
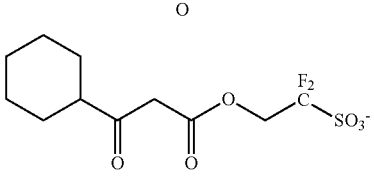
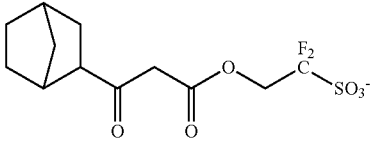

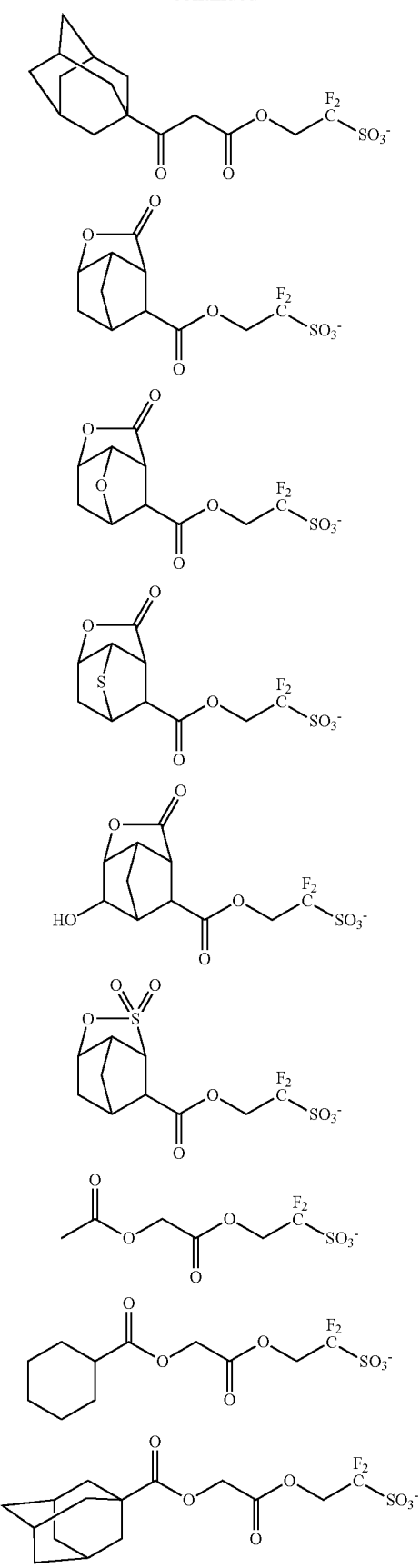
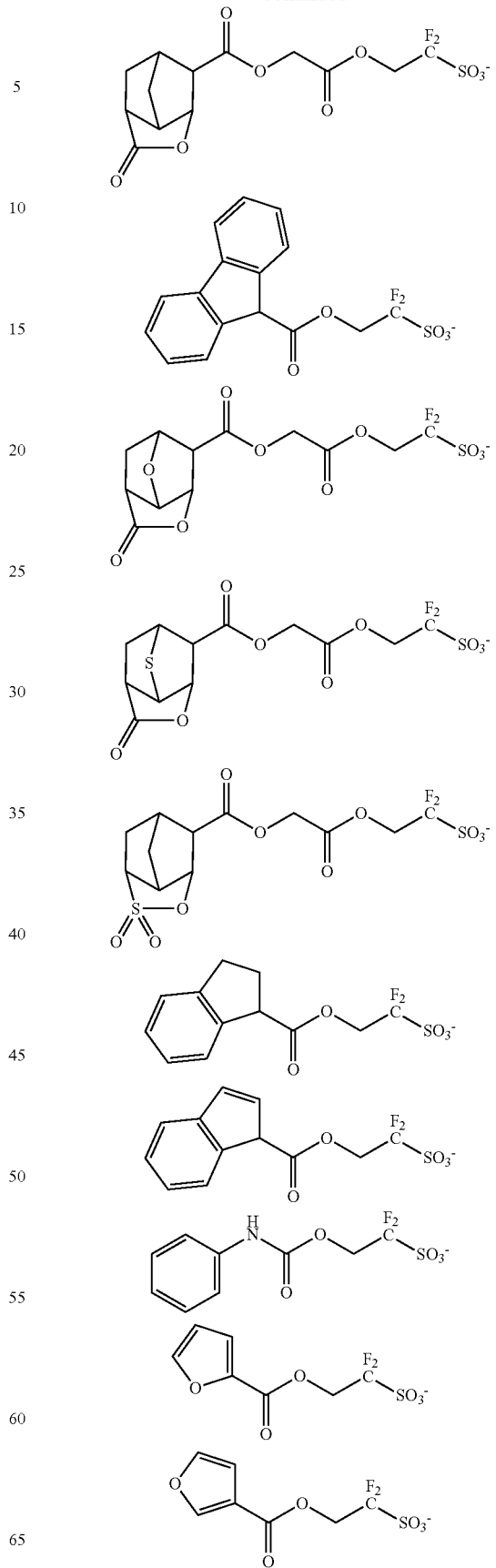

-continued
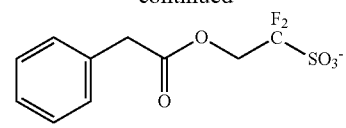
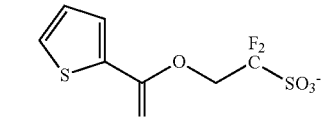
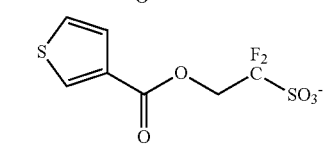
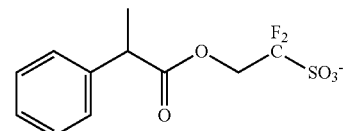
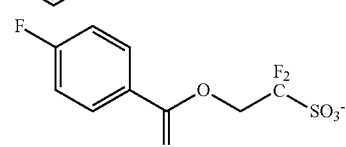
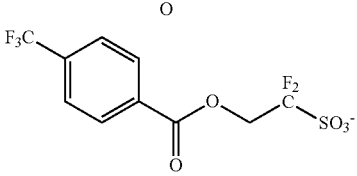
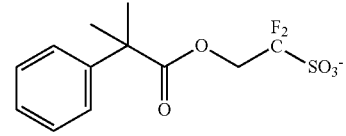
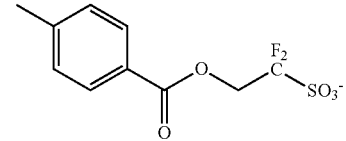
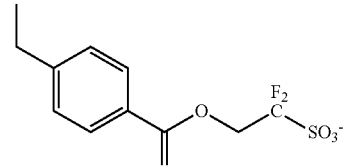
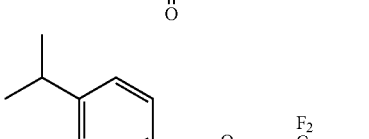
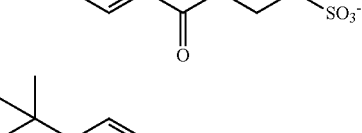
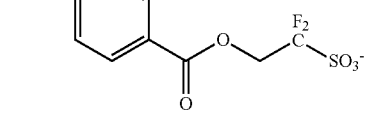
-continued
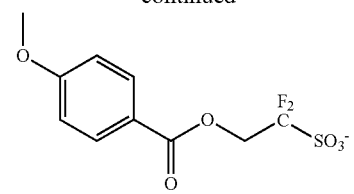
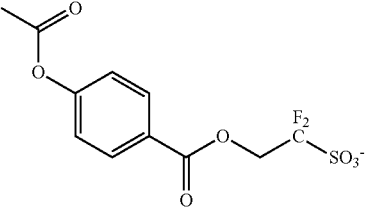
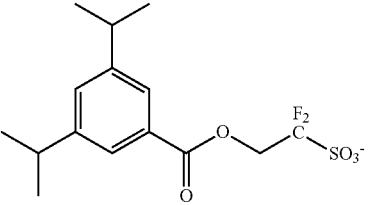
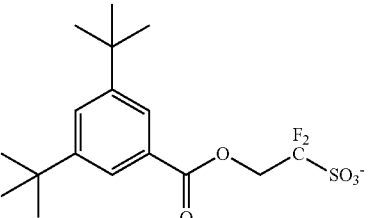
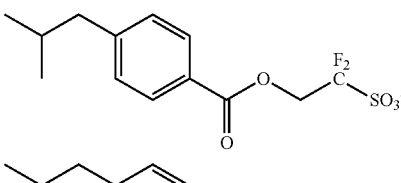
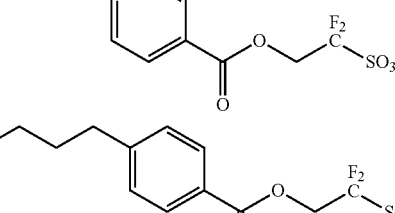
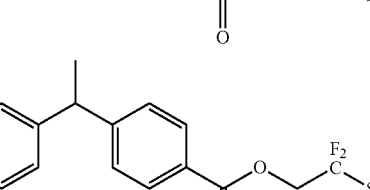
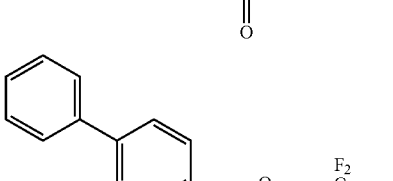
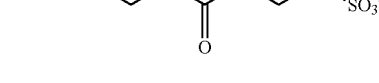

43
-continued
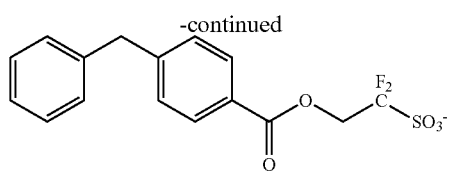
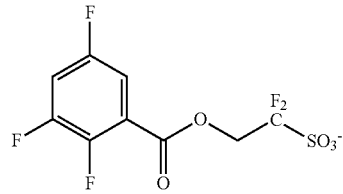
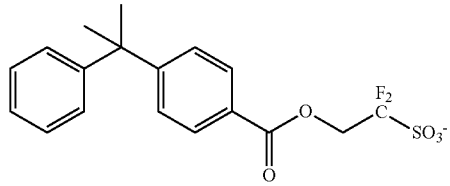
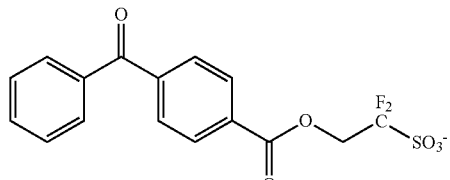
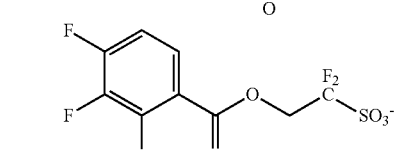
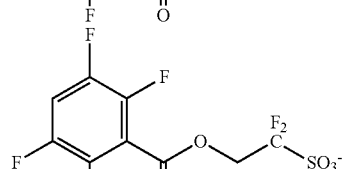
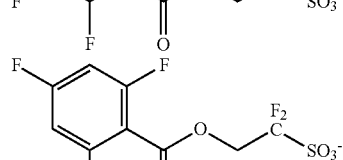
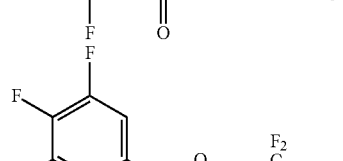
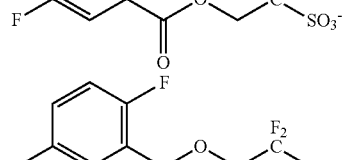
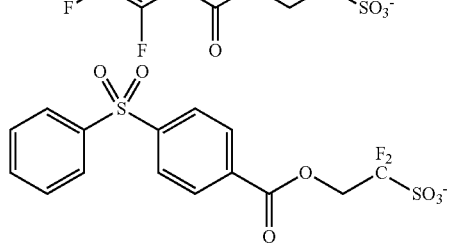
44
-continued
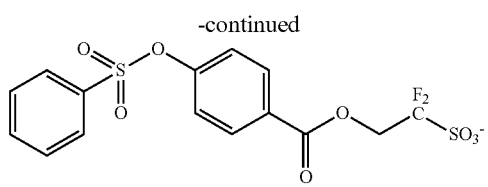
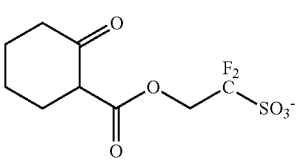
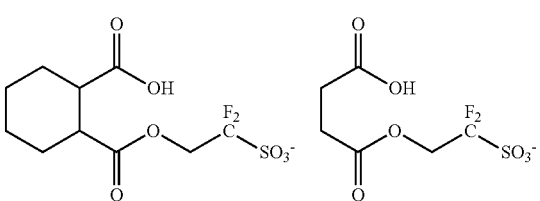
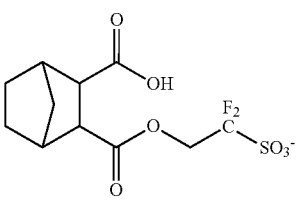
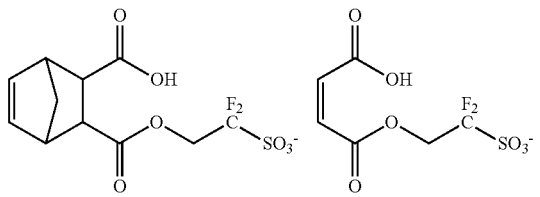
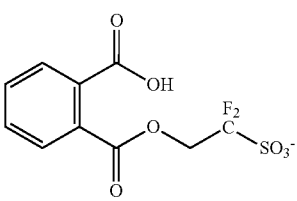
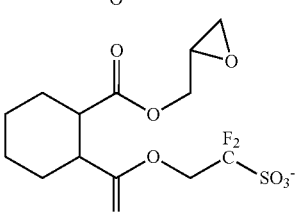
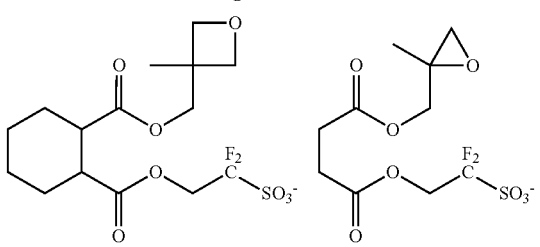

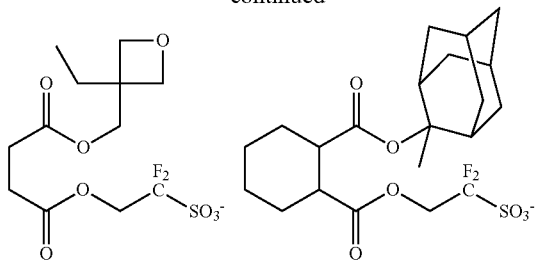
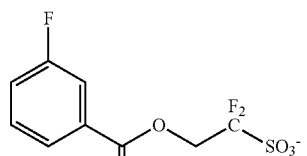
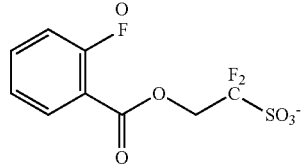
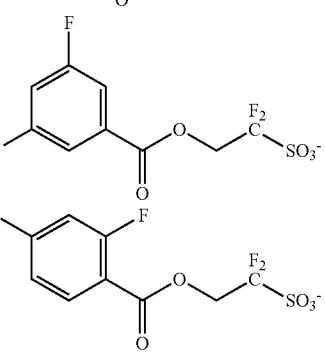
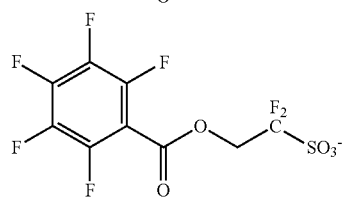
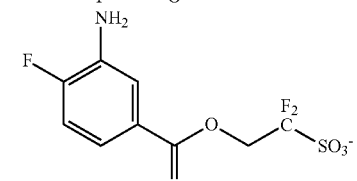
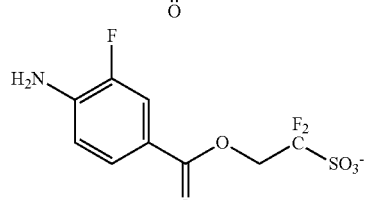
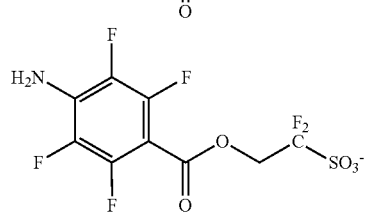
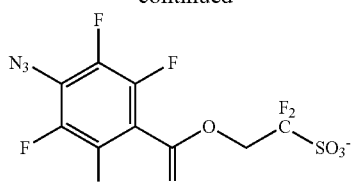
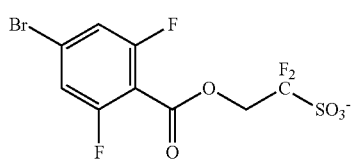
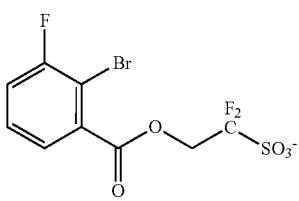
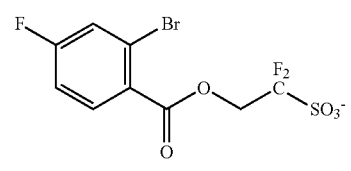
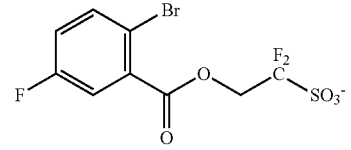
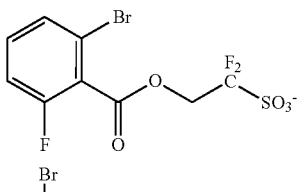
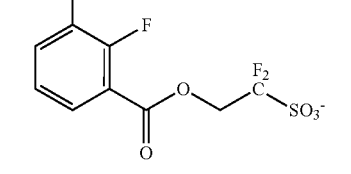
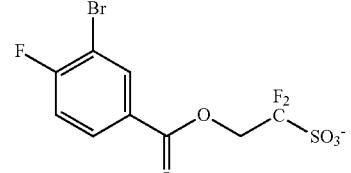
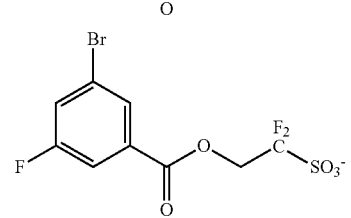

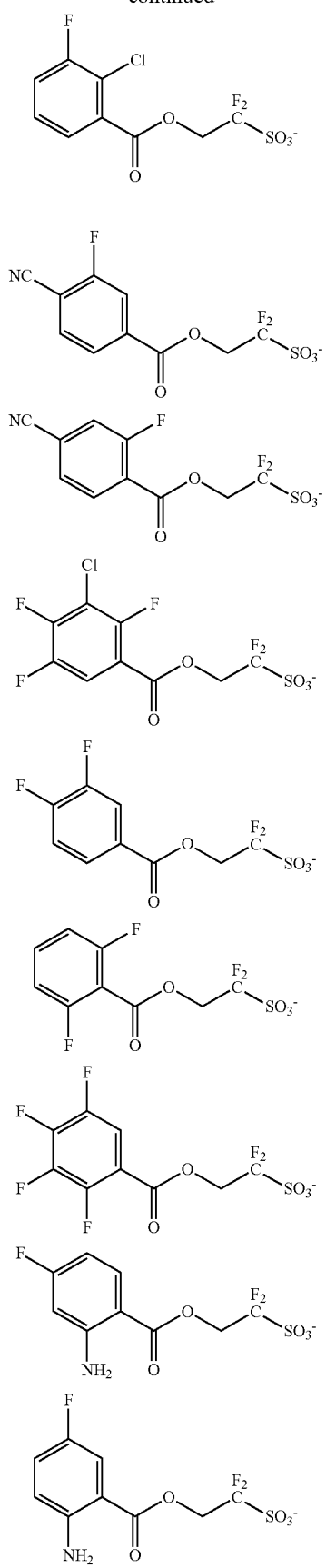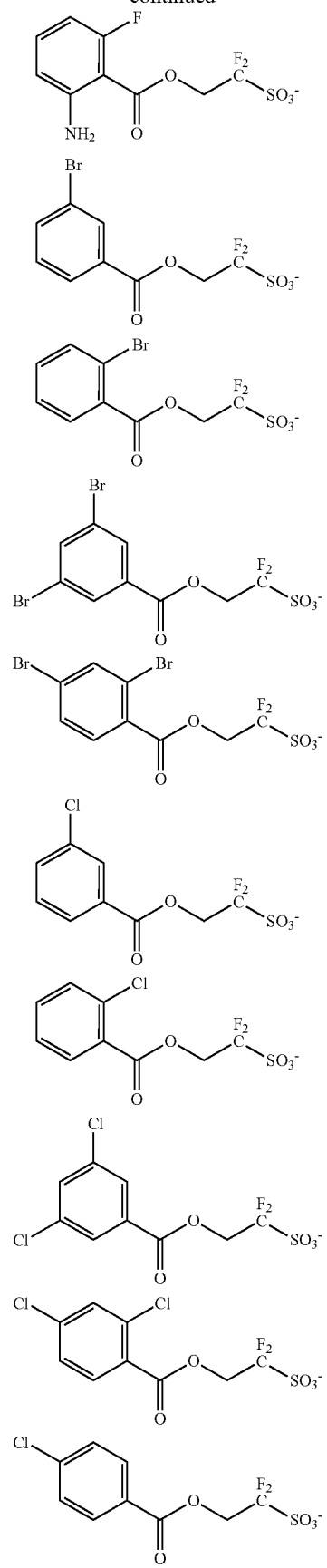

-continued
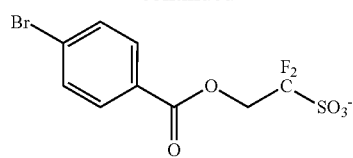
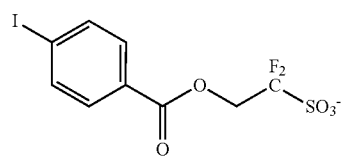
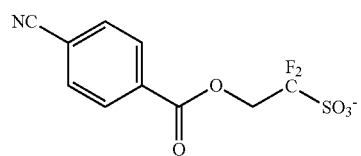
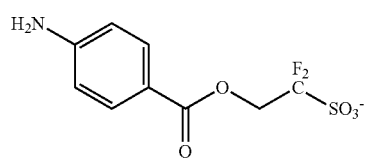
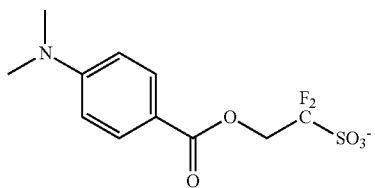
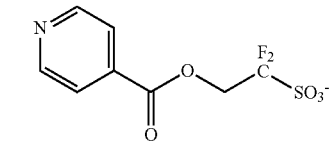
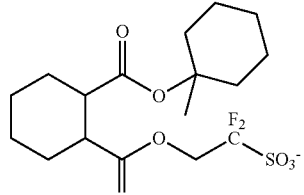
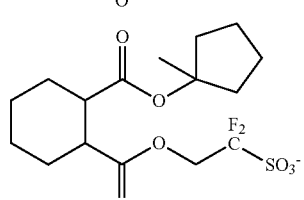
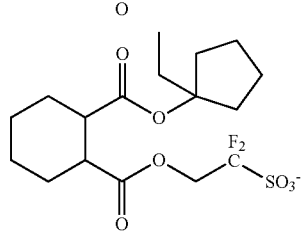
-continued
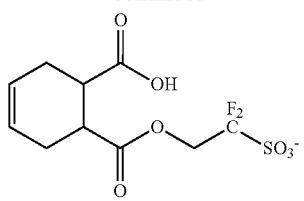
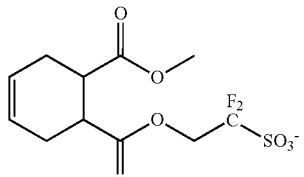
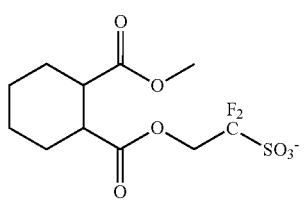
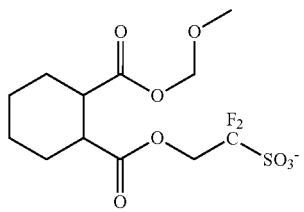
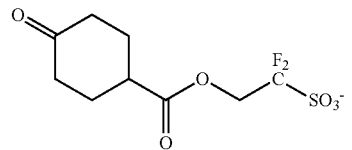
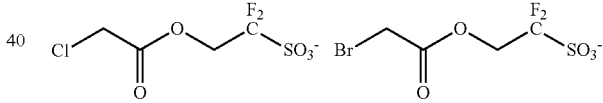
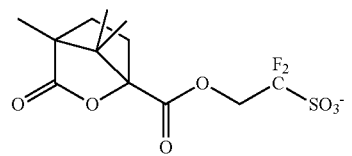
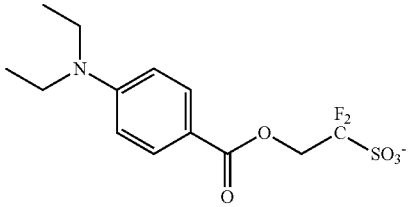
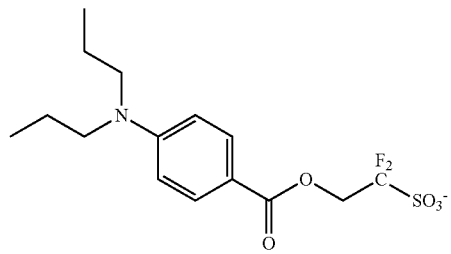

51
-continued
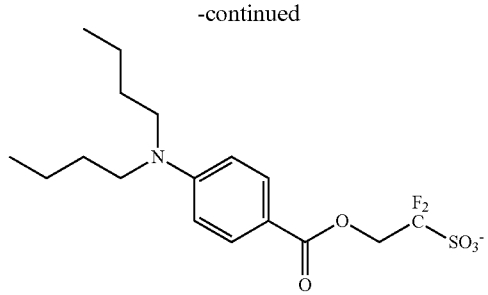
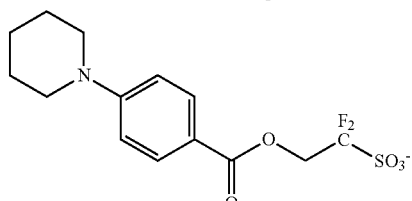
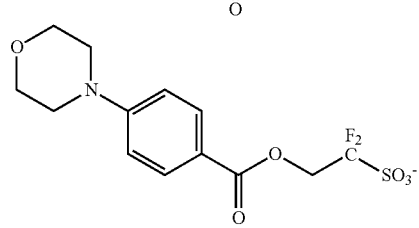
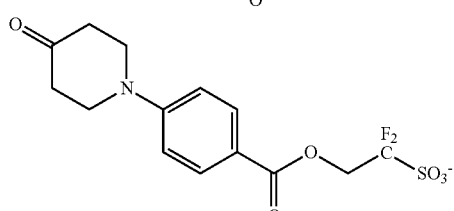
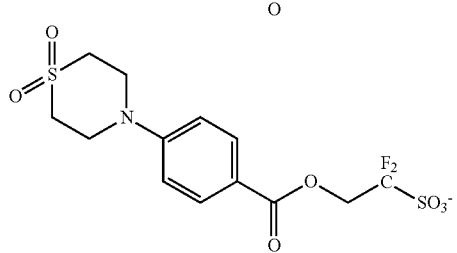
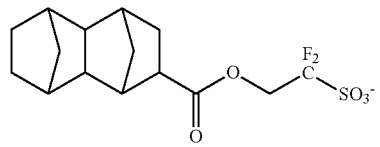
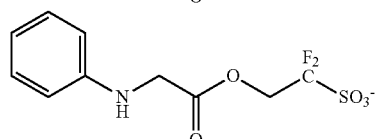
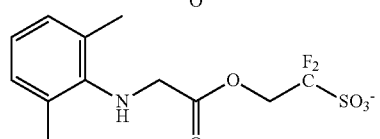
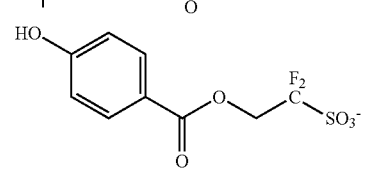
52
-continued
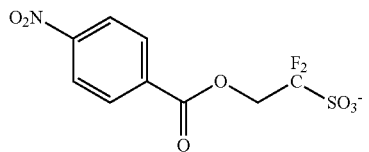
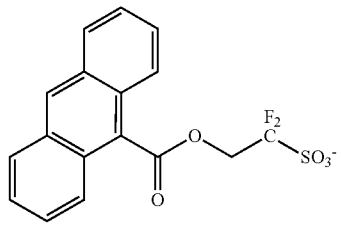
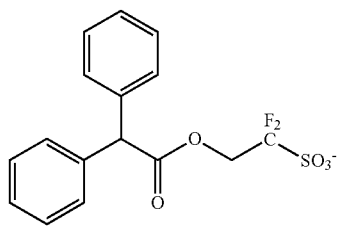
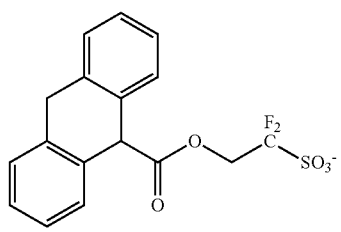
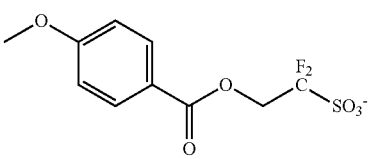
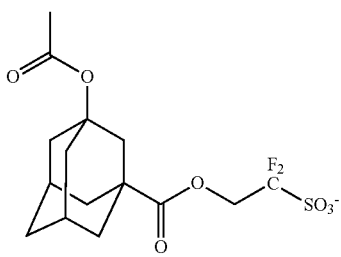
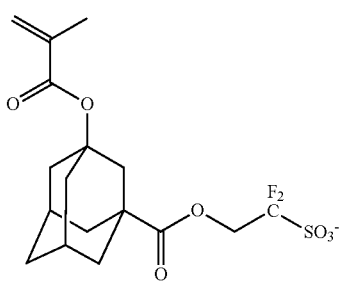

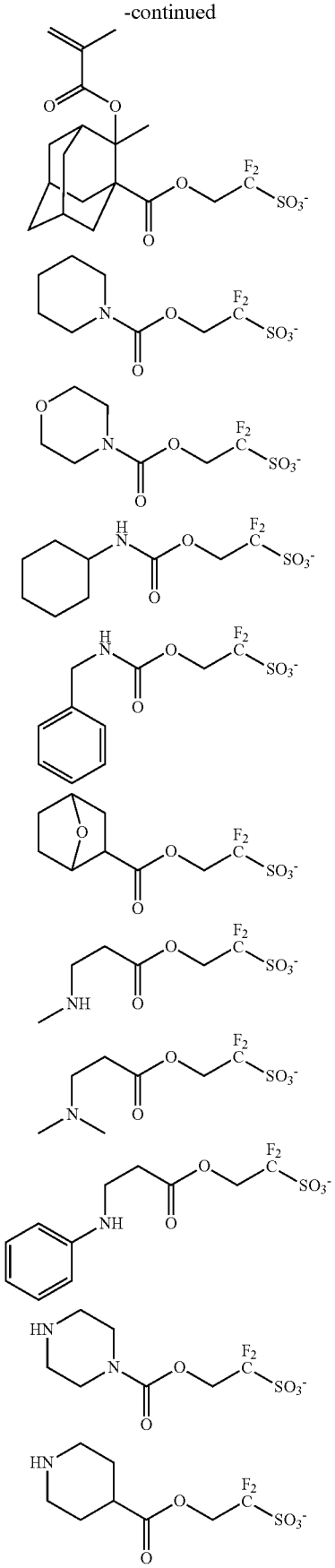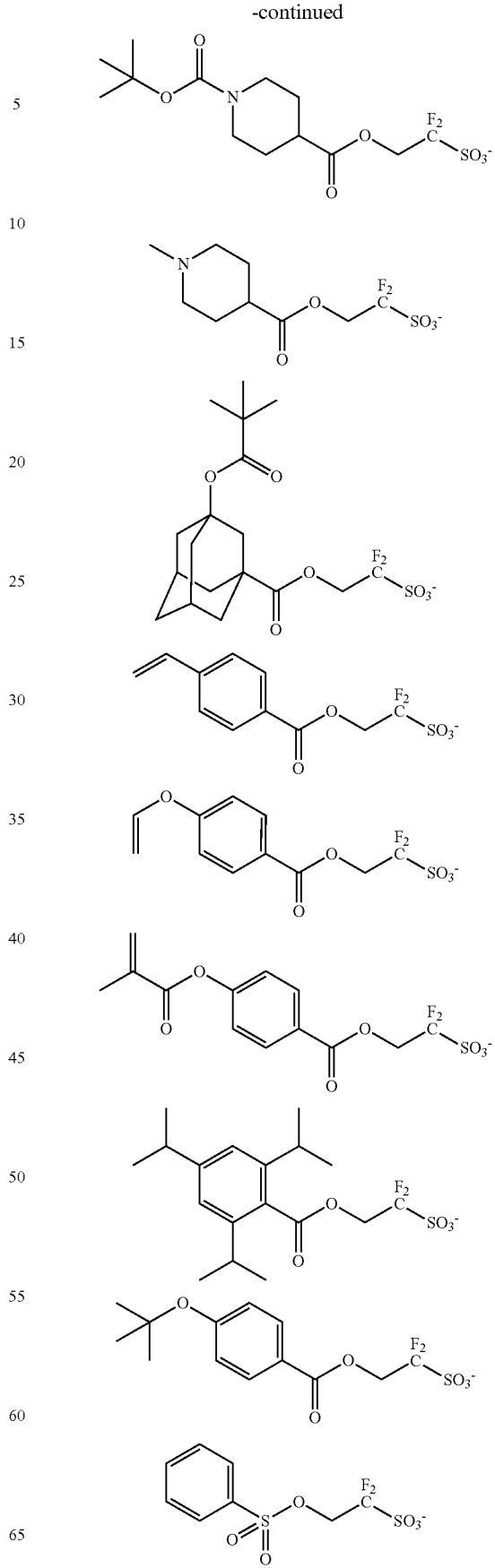

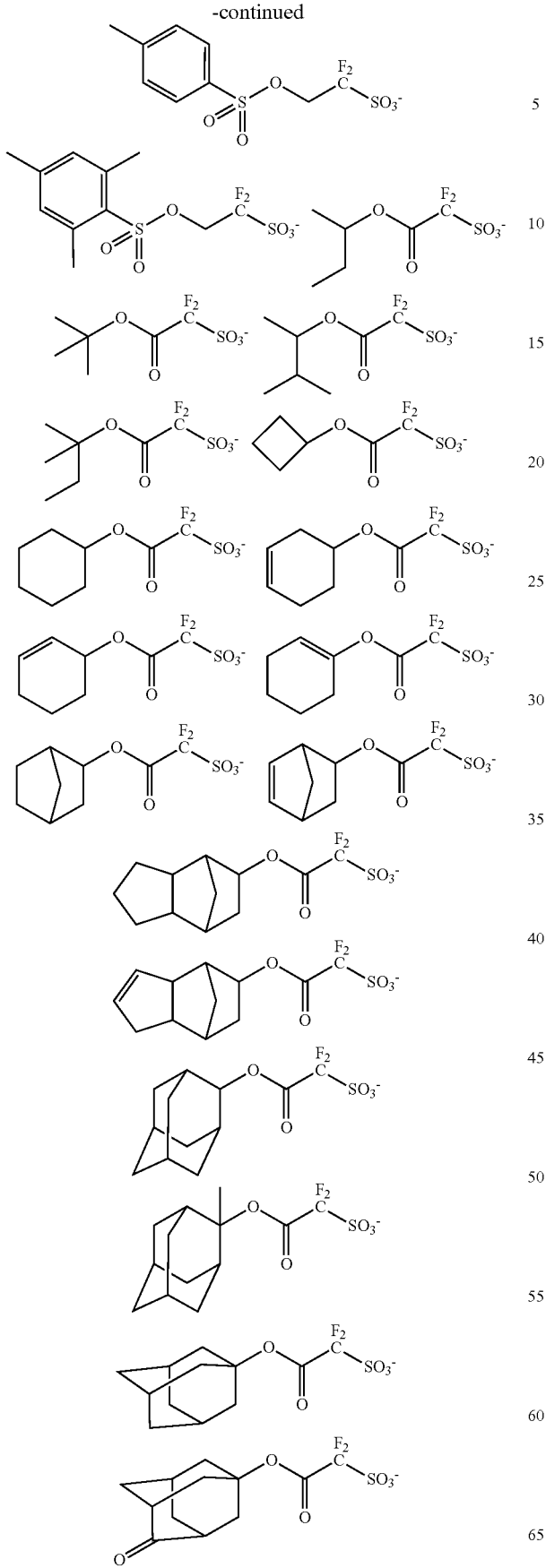
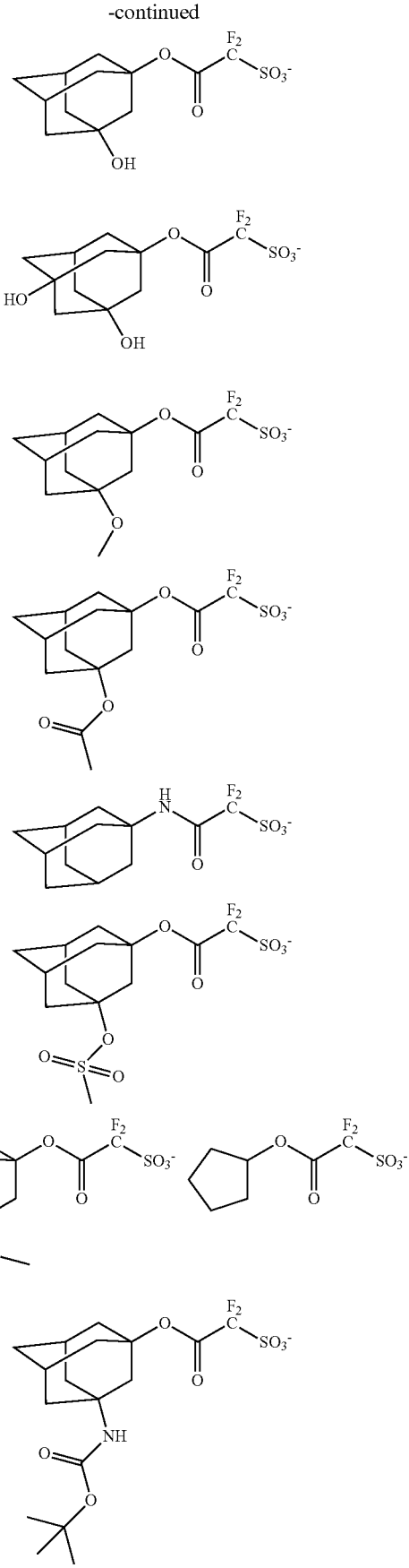

57
-continued
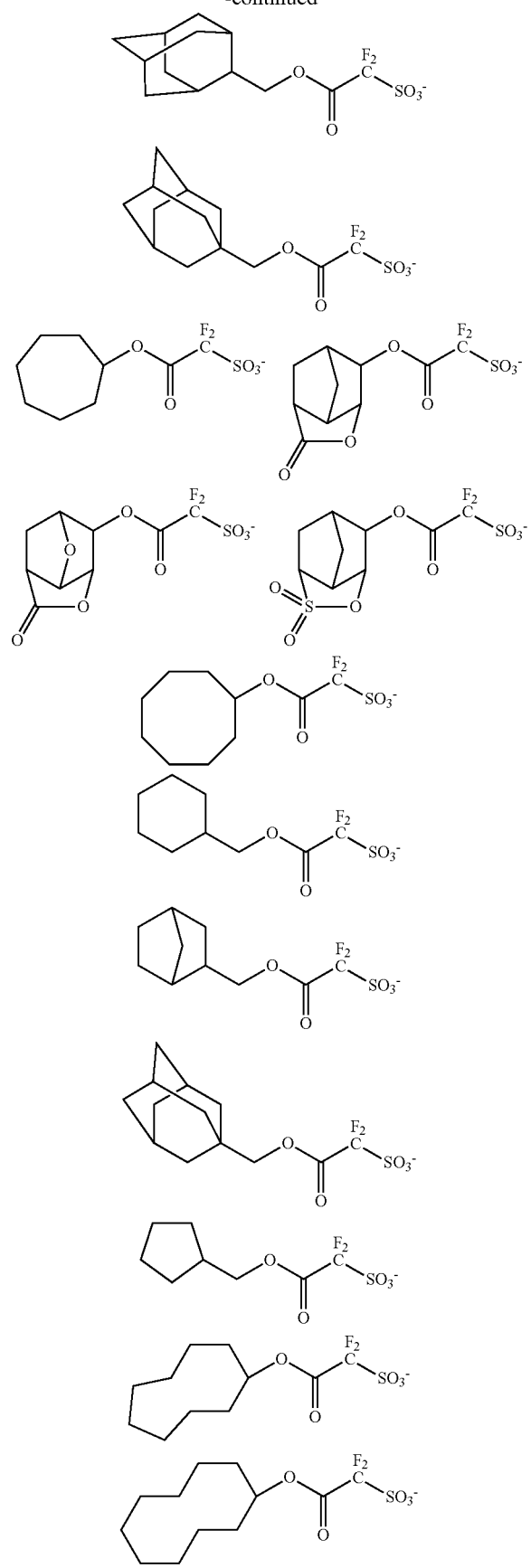
58
-continued
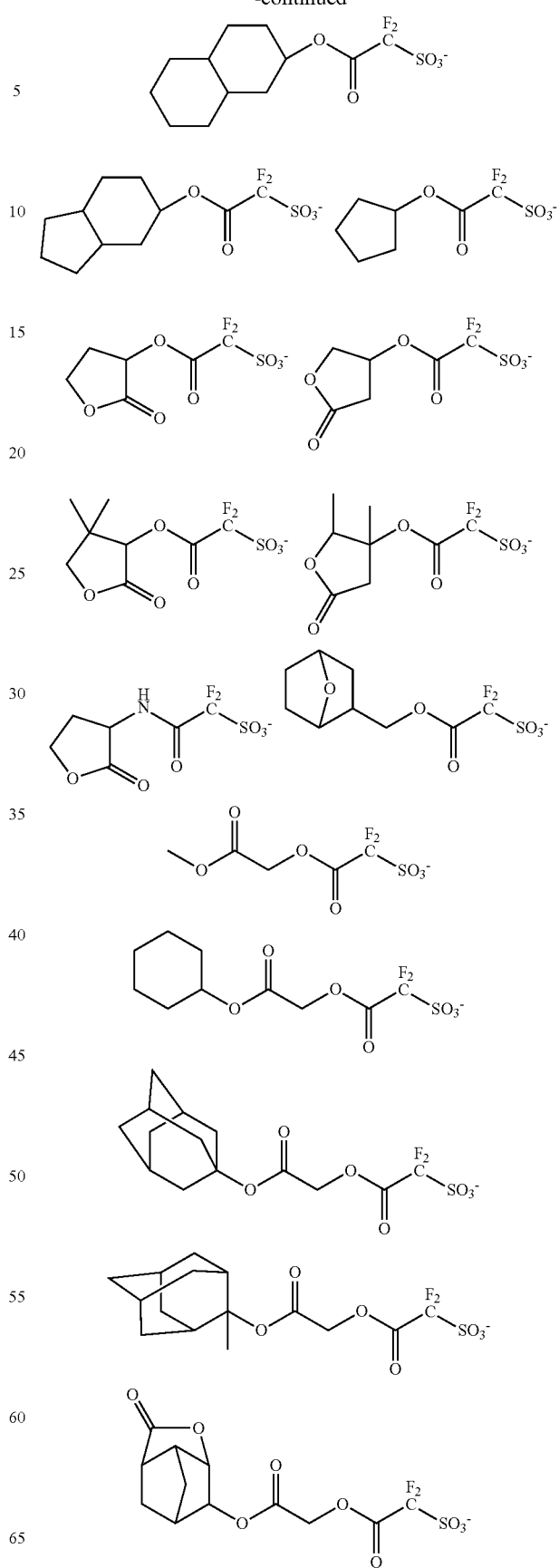

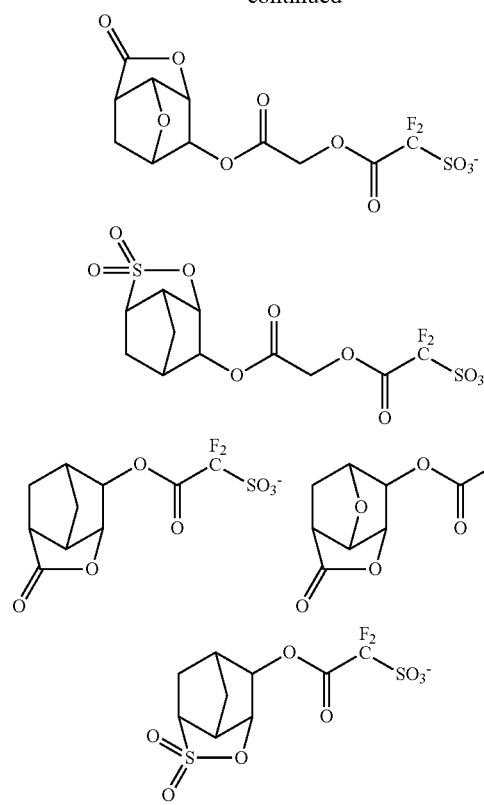
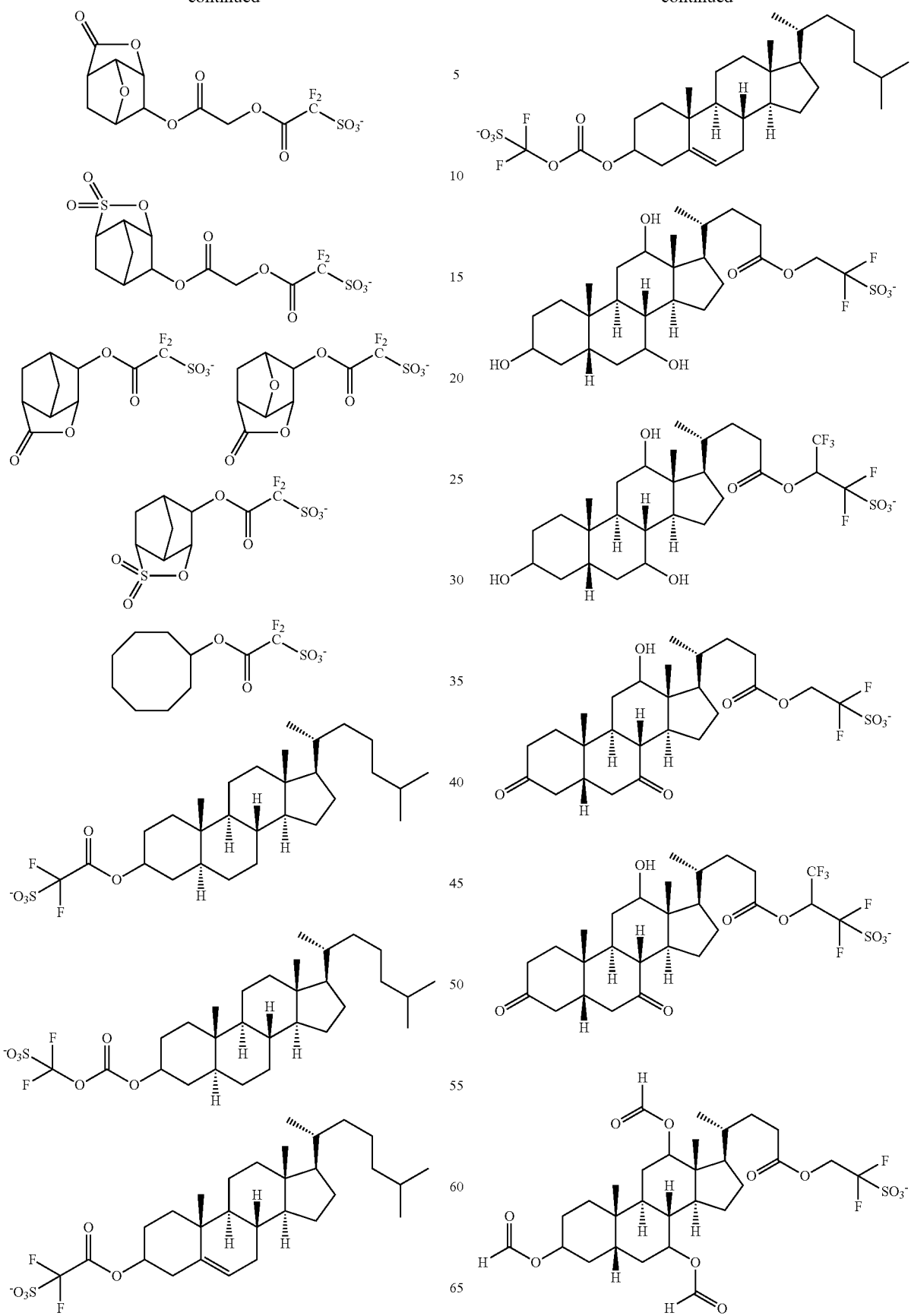

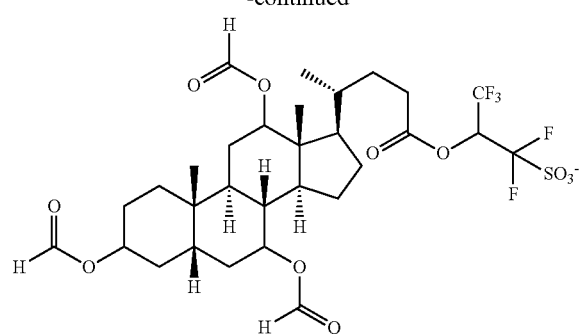
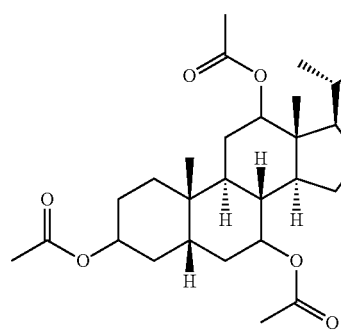
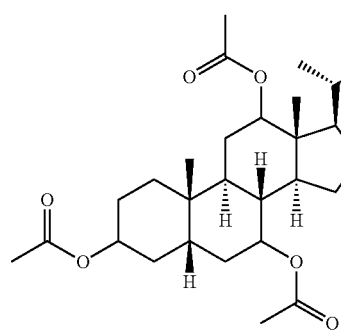
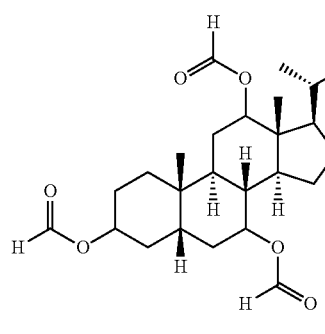
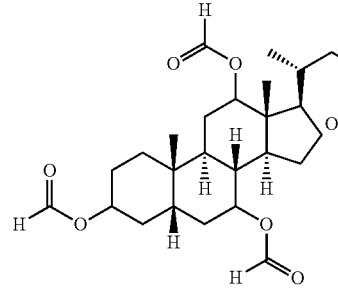
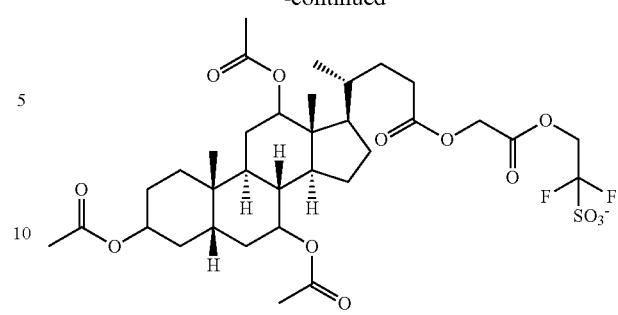
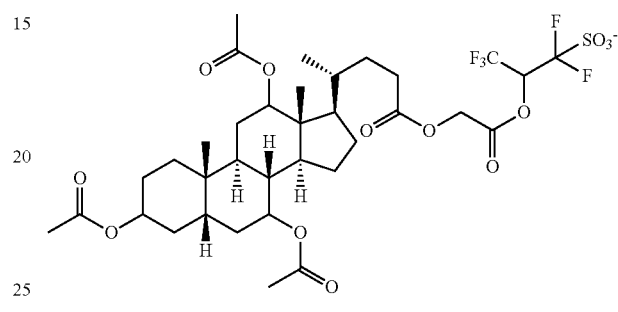
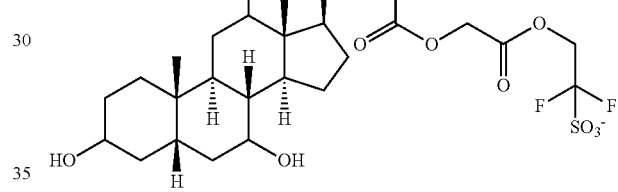
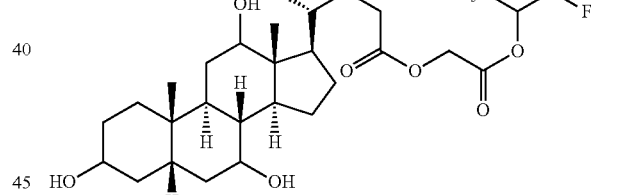
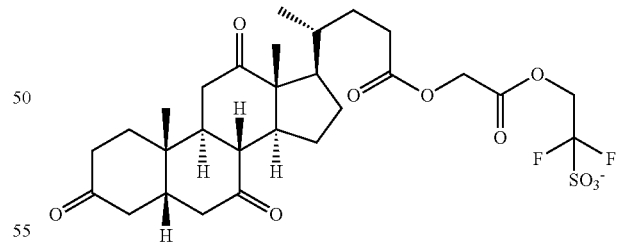
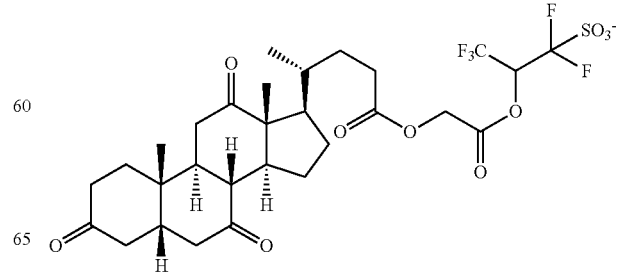

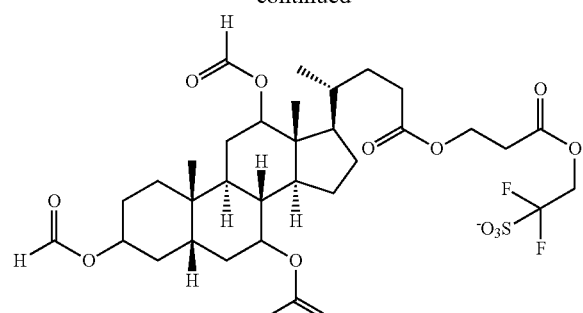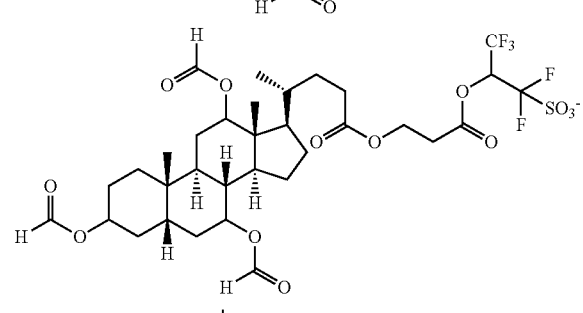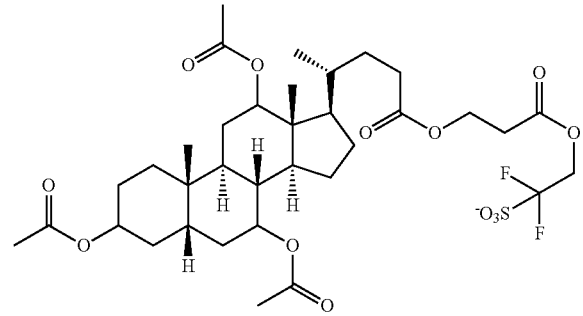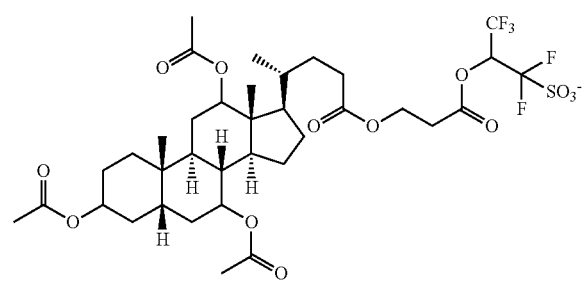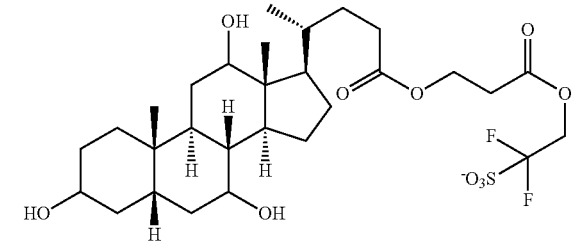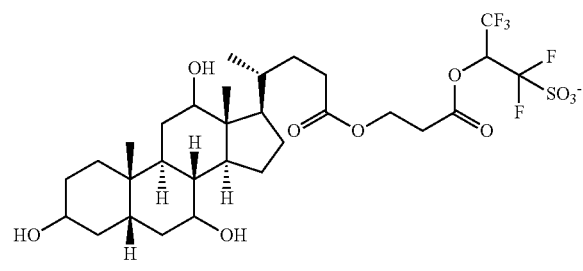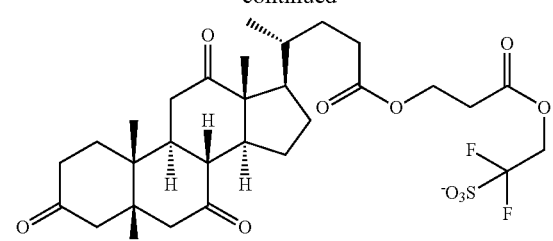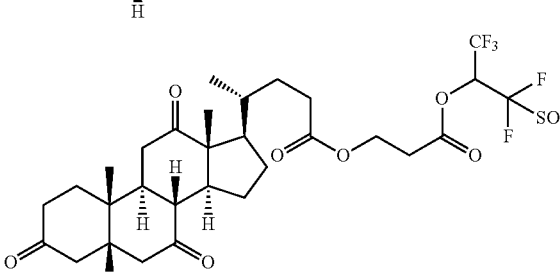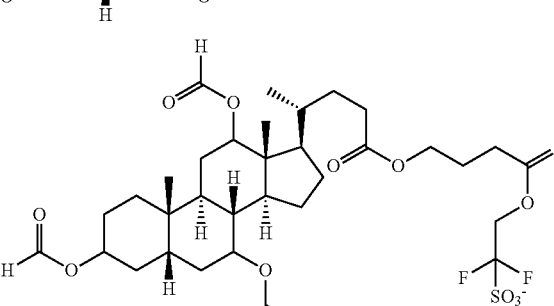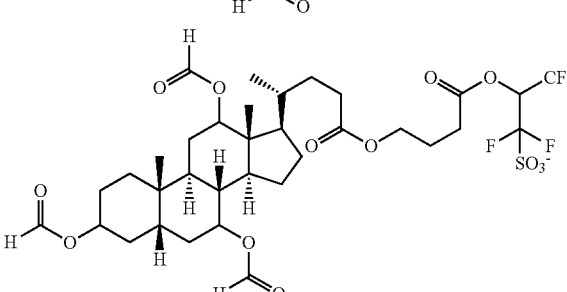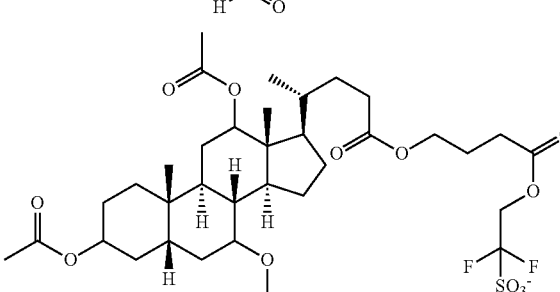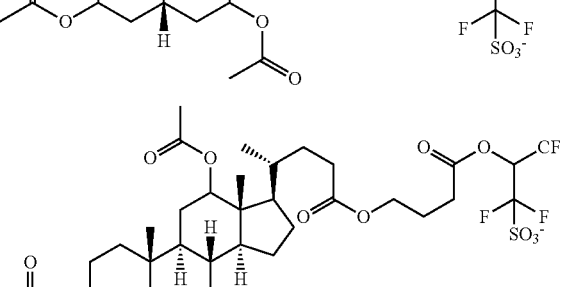

-continued
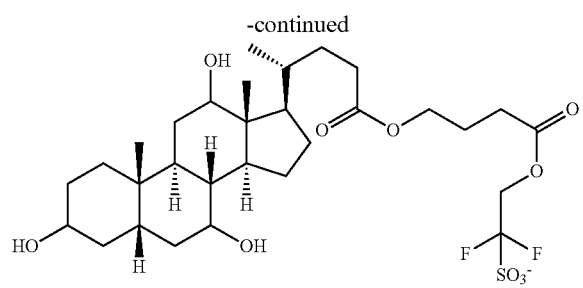
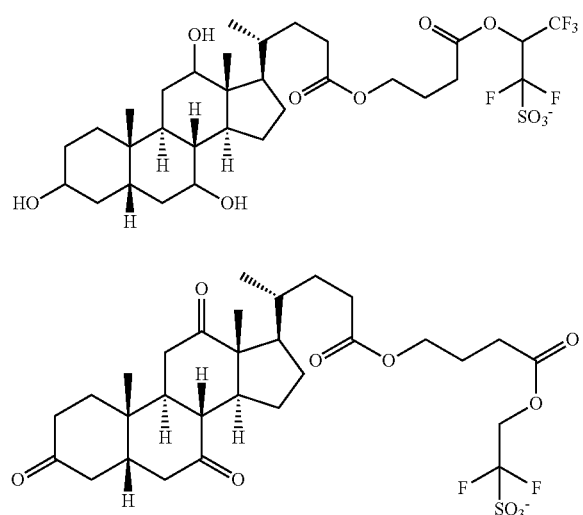
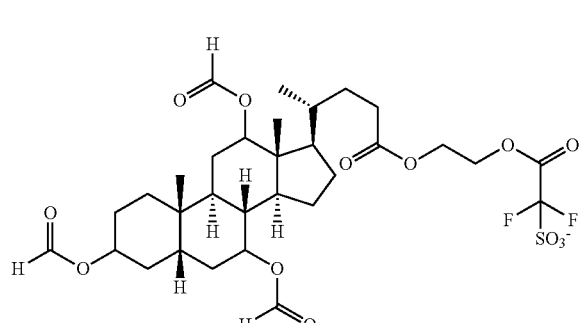
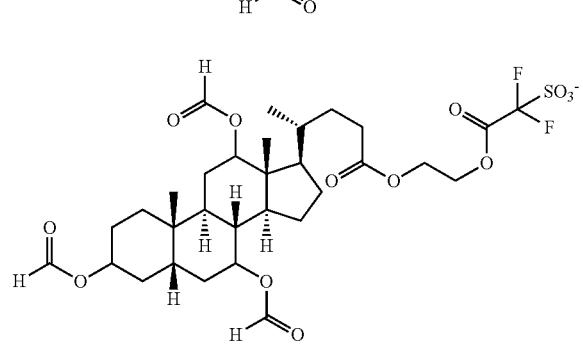
-continued
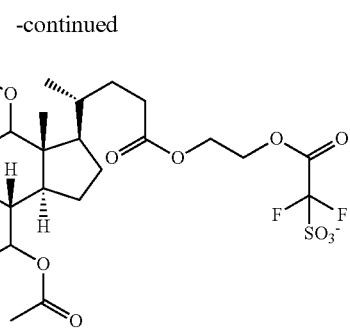
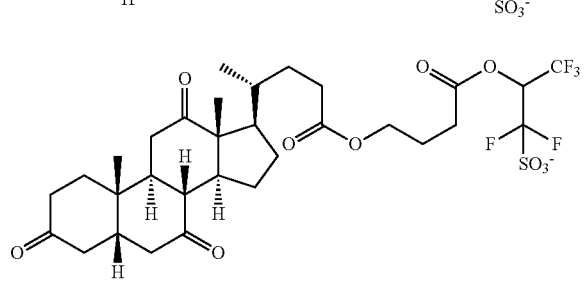
Of the salts having formula (1), barium salts having the following formula (2), cesium salts having the following formula (3), and cerium salts having the following formula (4) are preferred in that because of their large atomic number and possession of more electrons, these elements emit more secondary electrons upon exposure to EB or EUV and are thus more effective for providing the resist film with a higher sensitivity.

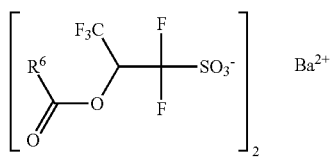
(2)

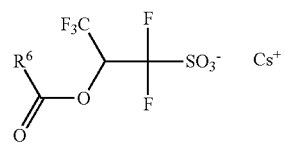
(3)

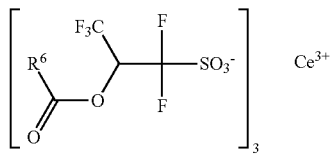
(4)

Herein $R^6$ is a $C_4$-$C_{20}$ straight, branched or cyclic alkyl, alkenyl or alkynyl group or a $C_6$-$C_{20}$ aryl group, which may contain a halogen atom, ether, thiol, ester, carbonate, carbonyl, amide, amino, azide, carbamate, nitro, cyano, hydroxyl, carboxyl, sulfo, sulfonic acid ester, sultone moiety, lactone ring or lactam ring.

The salt having formula (1) is preferably added in an amount of 0.01 to 100 parts, more preferably 0.1 to 50 parts by weight per 100 parts by weight of the base resin.

The salt having formula (1) may be synthesized, for example, by neutralization reaction or salt exchange reaction of a hydroxide, halide, carbonate, sulfate, carboxylate or β-keto-ester salt of sodium, magnesium, potassium, calcium, rubidium, strontium, yttrium, cesium, barium or cerium with an α-fluorinated sulfonic acid having a straight, branched or cyclic $C_5$-$C_{30}$ alkyl, alkenyl or alkynyl group or $C_6$-$C_{20}$ aryl group or an ammonium salt of the α-fluorinated sulfonic acid.

The recurring units containing an acid labile group in the base resin are preferably units having the formula (a1) or units having the formula (a2), which are simply referred to as units (a1) or (a2).

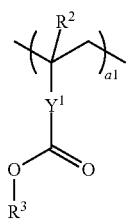
(a1)

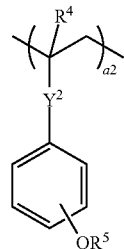
(a2)

Herein $R^2$ and $R^4$ are each independently hydrogen or methyl. $R^3$ and $R^5$ each are an acid labile group. $Y^1$ is a single bond, a $C_1$-$C_{12}$ linking group having at least one of ester moiety, lactone ring, phenylene moiety and naphthylene moiety, a phenylene group, or a naphthylene group. $Y^2$ is a single bond, ester group or amide group, a1 and a2 are numbers in the range: $0 \leq a1 \leq 0.9$, $0 \leq a2 \leq 0.9$, and $0 < a1+a2 < 1$.

Examples of the monomer from which the recurring unit (a1) is derived are shown below, but not limited thereto. $R^2$ and $R^3$ are as defined above.

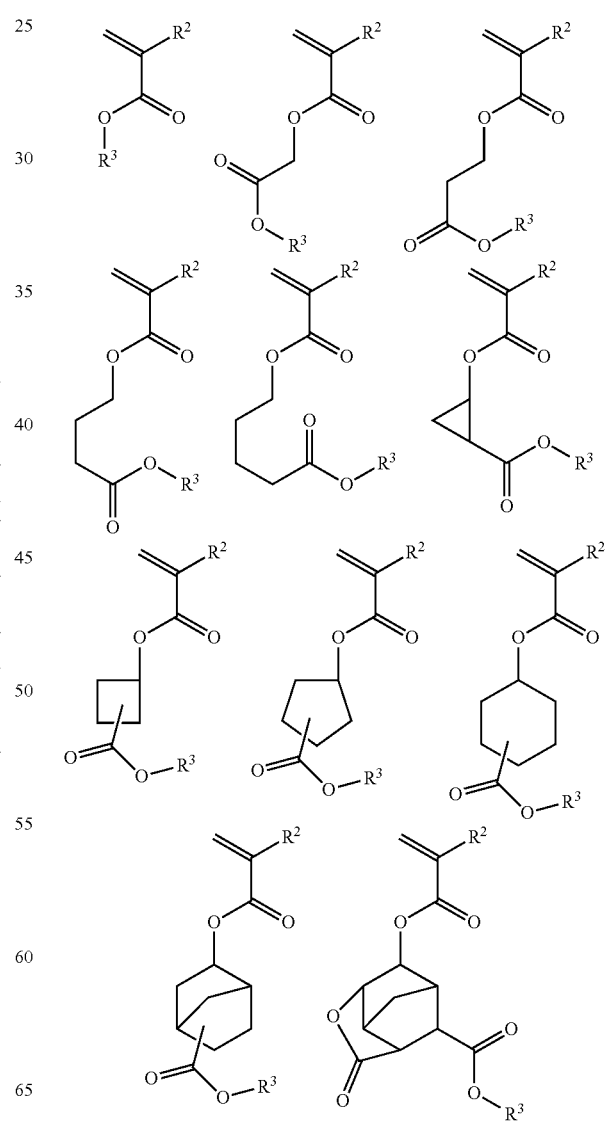

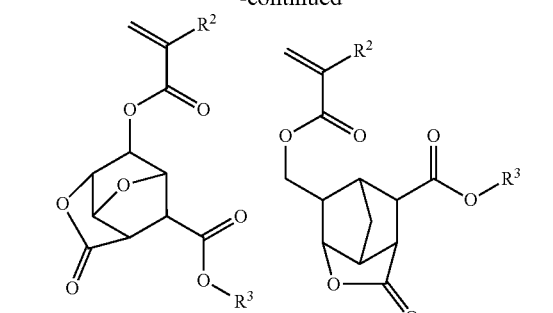
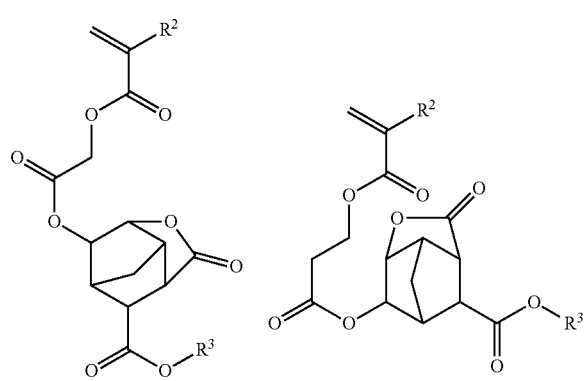
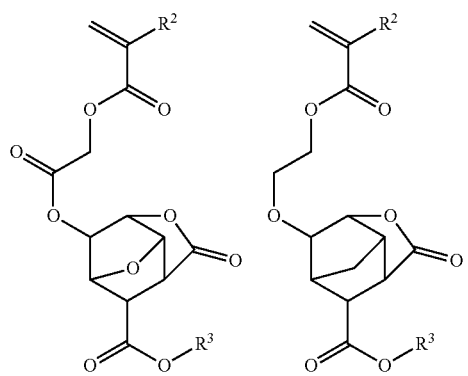
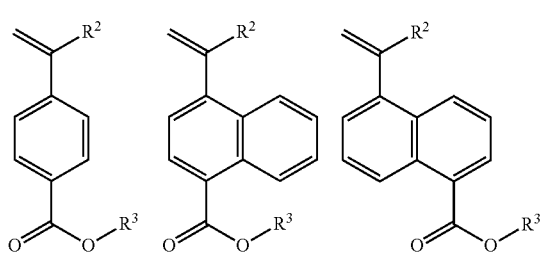
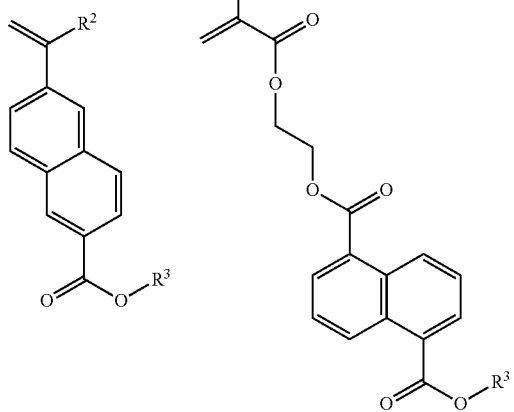
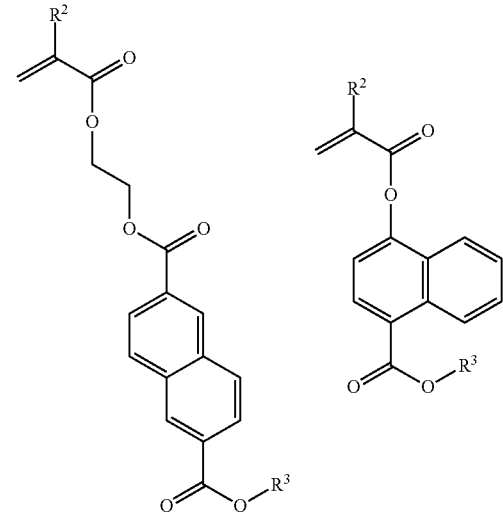
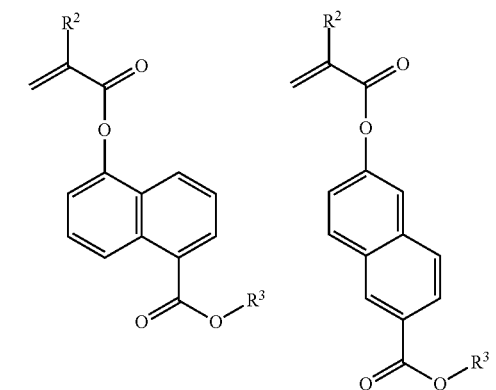
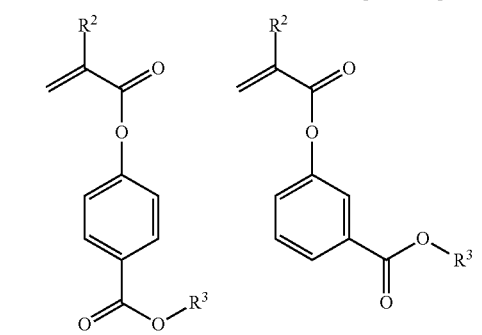

Examples of the monomer from which the recurring unit (a2) is derived are shown below, but not limited thereto. $R^4$ and $R^5$ are as defined above.

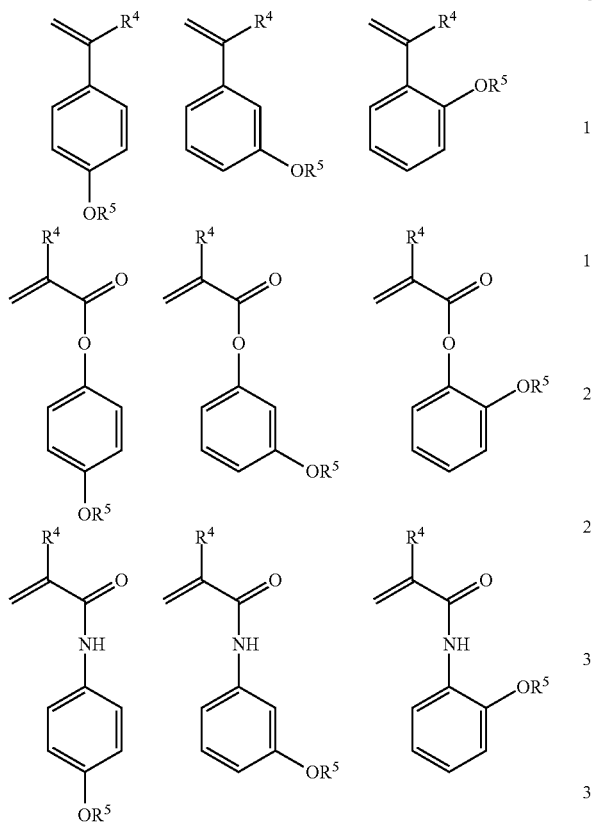

The acid labile groups represented by $R^3$ and $R^5$ may be selected from a variety of such groups. The acid labile groups may be the same or different and preferably include groups of the following formulae (A-1) to (A-3).

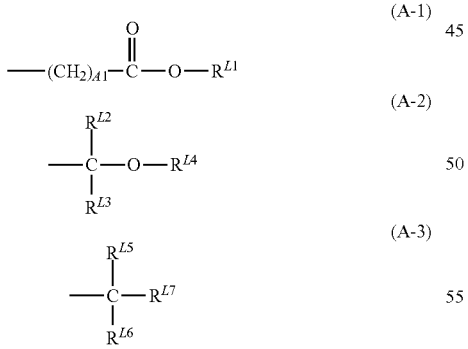

In formula (A-1), $R^{L1}$ is a tertiary alkyl group of 4 to 20 carbon atoms, preferably 4 to 15 carbon atoms, a trialkylsilyl group in which each alkyl moiety has 1 to 6 carbon atoms, an oxoalkyl group of 4 to 20 carbon atoms, or a group of formula (A-3). A1 is an integer of 0 to 6.

Exemplary tertiary alkyl groups are t-butyl, t-pentyl, 1,1-diethylpropyl, 1-ethylcyclopentyl, 1-butylcyclopentyl, 1-ethylcyclohexyl, 1-butylcyclohexyl, 1-ethyl-2-cyclopentenyl, 1-ethyl-2-cyclohexenyl, and 2-methyl-2-adamantyl.

Exemplary trialkylsilyl groups are trimethylsilyl, triethylsilyl, and dimethyl-t-butylsilyl. Exemplary oxoalkyl groups are 3-oxocyclohexyl, 4-methyl-2-oxooxan-4-yl, and 5-methyl-2-oxooxolan-5-yl.

Examples of the acid labile groups of formula (A-1) include t-butoxycarbonyl, t-butoxycarbonylmethyl, t-pentyloxycarbonyl, t-pentyloxycarbonylmethyl, 1,1-diethylpropyloxycarbonyl, 1,1-diethylpropyloxycarbonylmethyl, 1-ethylcyclopentyloxycarbonyl, 1-ethylcyclopentyloxycarbonylmethyl, 1-ethyl-2-cyclopentenyloxycarbonyl, 1-ethyl-2-cyclopentenyloxycarbonylmethyl, 1-ethoxyethoxycarbonylmethyl, 2-tetrahydropyranyloxycarbonylmethyl, and 2-tetrahydrofuranyloxycarbonylmethyl groups.

Also included are groups having the formulae (A-1)-1 to (A-1)-10.

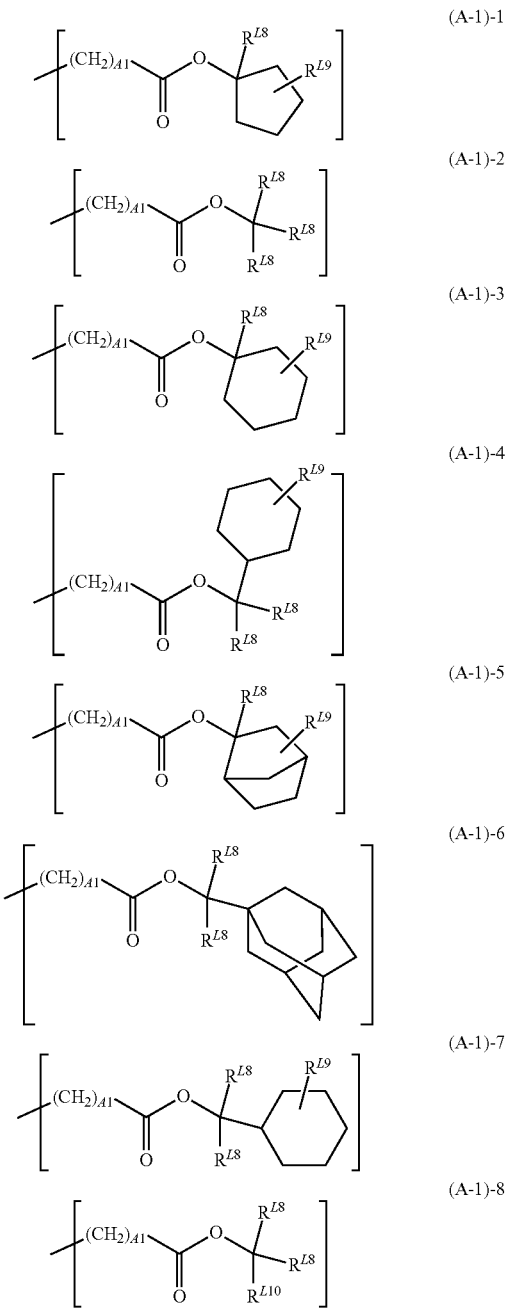

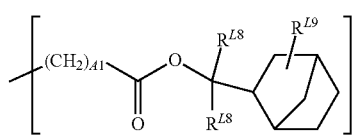
(A-1)-9

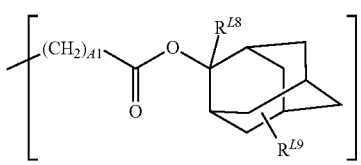
(A-1)-10

Herein $R^{L8}$ is each independently a straight, branched or cyclic $C_1$-$C_{10}$ alkyl group or $C_6$-$C_{20}$ aryl group, $R^{L9}$ is hydrogen or a straight, branched or cyclic $C_1$-$C_{10}$ alkyl group, $R^{L10}$ is each independently a straight, branched or cyclic $C_2$-$C_{10}$ alkyl group or $C_6$-$C_{20}$ aryl group, and A1 is as defined above.

In formula (A-2), $R^{L2}$ and $R^{L3}$ each are hydrogen or a straight, branched or cyclic alkyl group of 1 to 18 carbon atoms, preferably 1 to 10 carbon atoms. Exemplary alkyl groups include methyl, ethyl, propyl, isopropyl, n-butyl, s-butyl, t-butyl, cyclopentyl, cyclohexyl, 2-ethylhexyl, and n-octyl. $R^{L4}$ is a monovalent hydrocarbon group of 1 to 18 carbon atoms, preferably 1 to 10 carbon atoms, which may contain a heteroatom such as oxygen, examples of which include straight, branched or cyclic alkyl groups and substituted forms of such alkyl groups in which some hydrogen atoms are replaced by hydroxyl, alkoxy, oxo, amino, alkylamino or the like. Illustrative examples of the substituted alkyl groups are shown below.

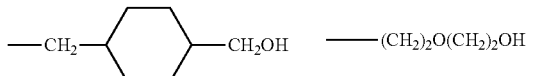
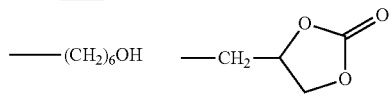

A pair of $R^{L2}$ and $R^{L3}$, $R^{L2}$ and $R^{L4}$, or $R^{L3}$ and $R^{L4}$ may bond together to form a ring with the carbon atom or the carbon and oxygen atoms to which they are attached. Each of $R^{L2}$ and $R^{L3}$, $R^{L2}$ and $R^{L4}$, or $R^{L3}$ and $R^{L4}$ is a straight or branched alkylene group of 1 to 18 carbon atoms, preferably 1 to 10 carbon atoms when they form a ring, while the ring preferably has 3 to 10 carbon atoms, more preferably 4 to 10 carbon atoms.

Of the acid labile groups of formula (A-2), the straight and branched ones are exemplified by the following groups having formulae (A-2)-1 to (A-2)-69.

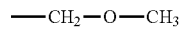
(A-2)-1

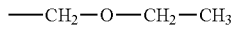
(A-2)-2

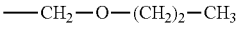
(A-2)-3

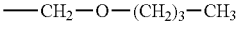
(A-2)-4

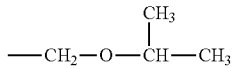
(A-2)-5

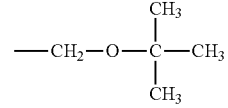
(A-2)-6

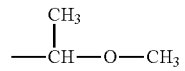
(A-2)-7

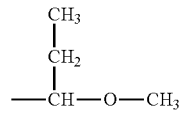
(A-2)-8

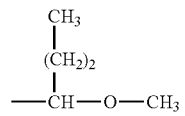
(A-2)-9

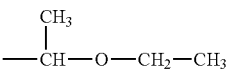
(A-2)-10

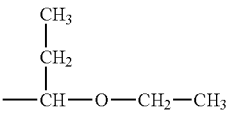
(A-2)-11

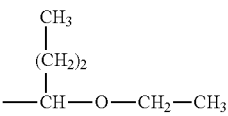
(A-2)-12

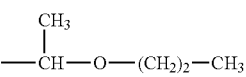
(A-2)-13

(A-2)-14

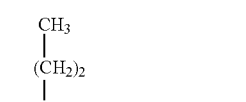
(A-2)-15

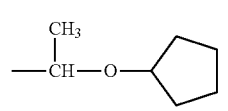
(A-2)-16

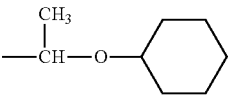
(A-2)-17

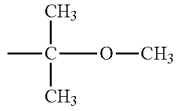
(A-2)-18

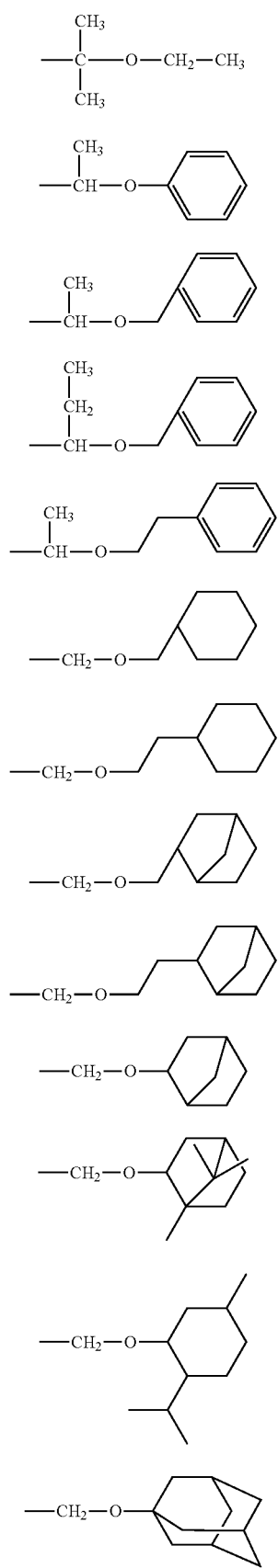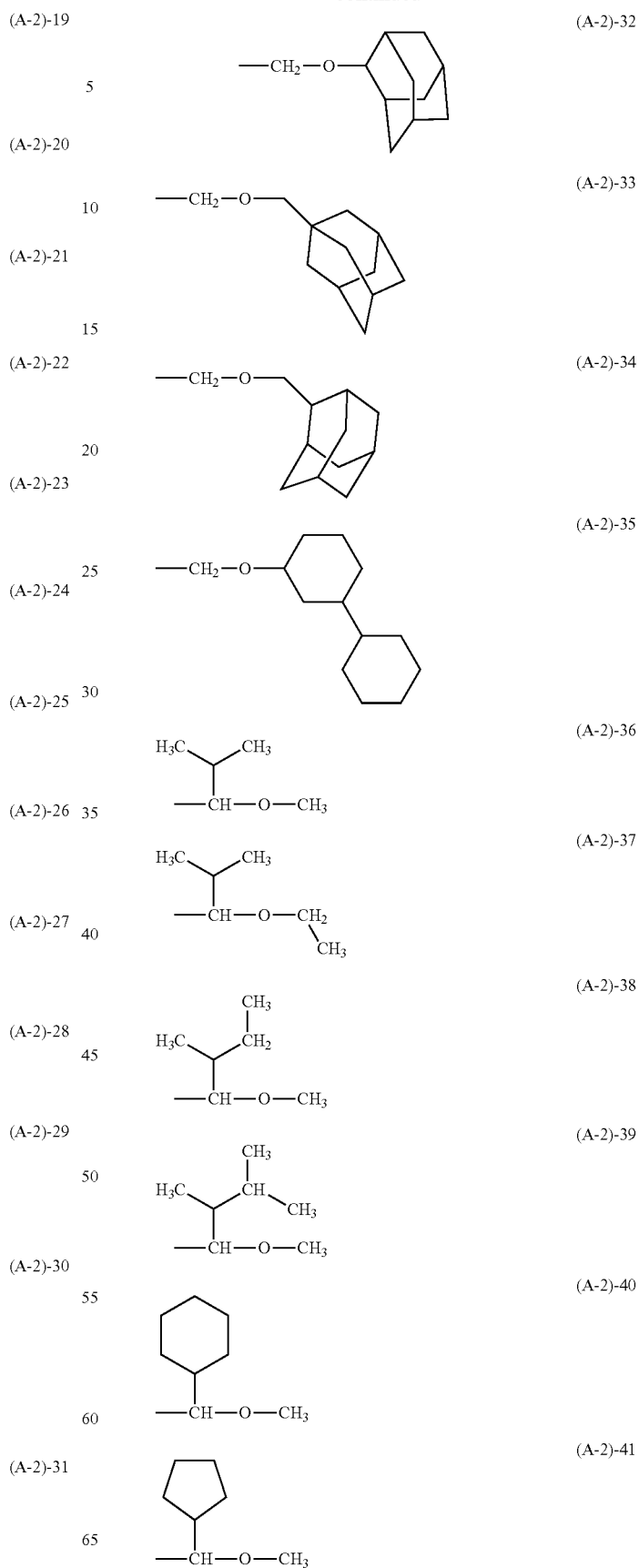

(A-2)-42
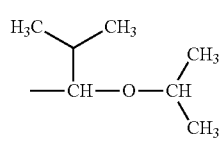
(A-2)-43
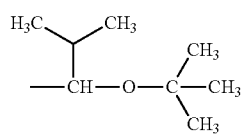
(A-2)-44
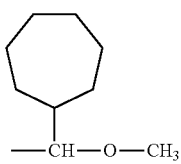
(A-2)-45
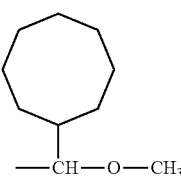
(A-2)-46
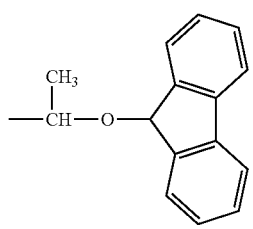
(A-2)-47
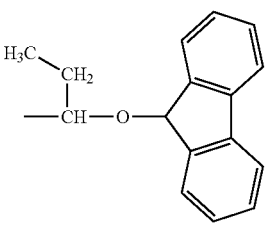
(A-2)-48
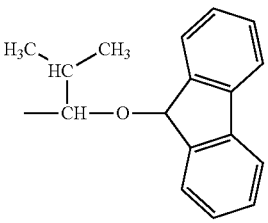
(A-2)-49
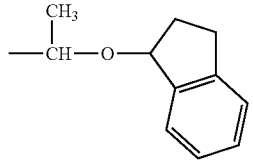
(A-2)-50
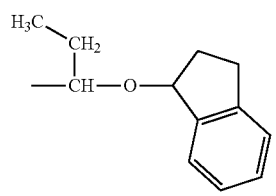
(A-2)-51
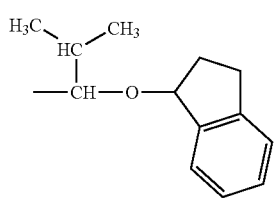
(A-2)-52
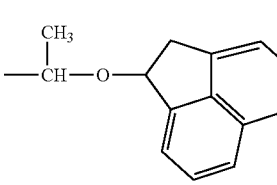
(A-2)-53
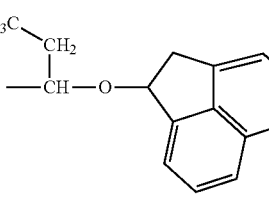
(A-2)-54
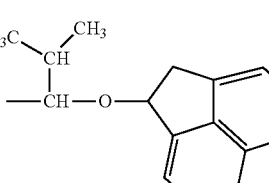
(A-2)-55
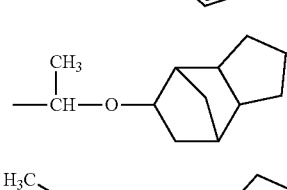
(A-2)-56
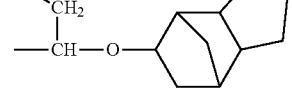
(A-2)-57
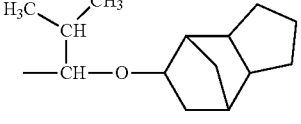
(A-2)-58
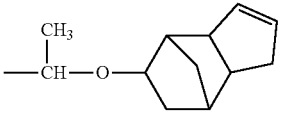
(A-2)-59
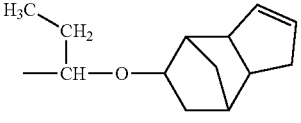

(A-2)-60 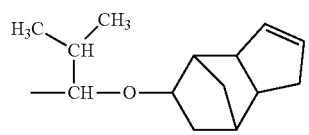

(A-2)-61 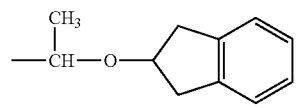

(A-2)-62 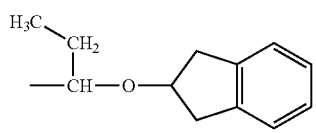

(A-2)-63 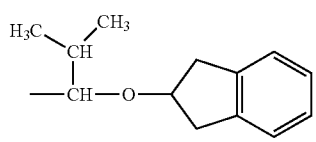

(A-2)-64 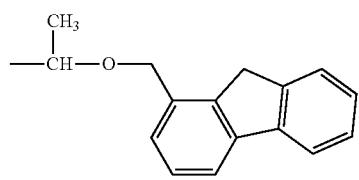

(A-2)-65 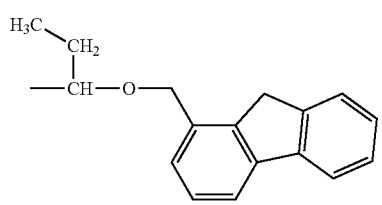

(A-2)-66 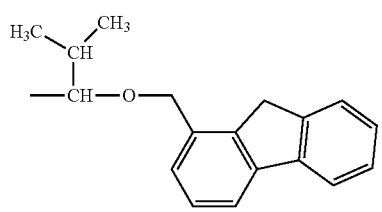

(A-2)-67 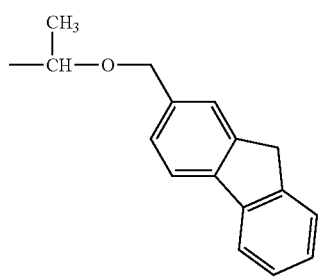

(A-2)-68 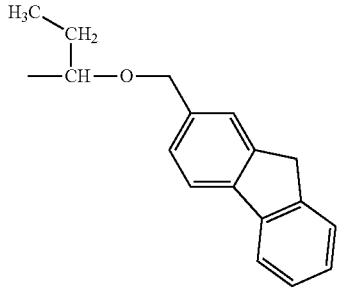

(A-2)-69 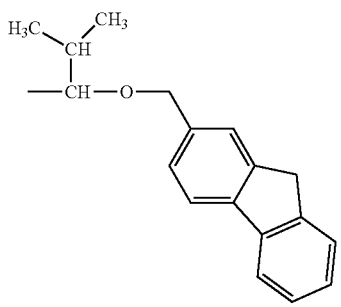

Of the acid labile groups of formula (A-2), the cyclic ones are, for example, tetrahydrofuran-2-yl, 2-methyltetrahydrofuran-2-yl, tetrahydropyran-2-yl, and 2-methyltetrahydropyran-2-yl.

Other examples of acid labile groups include those of the following formula (A-2a) or (A-2b) while the polymer may be crosslinked within the molecule or between molecules with these acid labile groups.

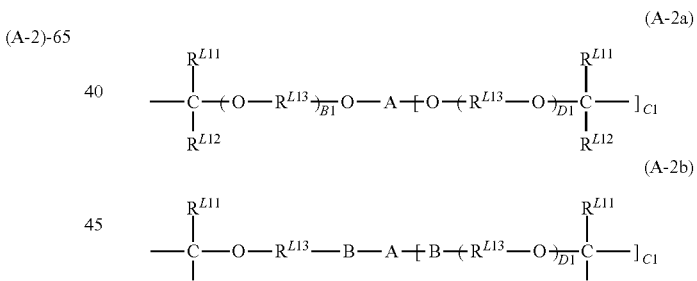

Herein $R^{L11}$ and $R^{L12}$ each are hydrogen or a straight, branched or cyclic $C_1$-$C_8$ alkyl group, or $R^{L11}$ and $R^{L12}$, taken together, may form a ring with the carbon atom to which they are attached, and each of $R^{L11}$ and $R^{L12}$ is a straight or branched $C_1$-$C_8$ alkylene group when they form a ring. $R^{L13}$ is independently a straight, branched or cyclic $C_1$-$C_{10}$ alkylene group. Each of B1 and D1 is an integer of 0 to 10, preferably 0 to 5, and C1 is an integer of 1 to 7, preferably 1 to 3.

"A" is a (C1+1)-valent aliphatic or alicyclic saturated hydrocarbon group, aromatic hydrocarbon group or heterocyclic group having 1 to 50 carbon atoms, which may be separated by a heteroatom or in which one or more carbon-bonded hydrogen atoms may be substituted by a hydroxyl, carboxyl, acyl moiety or fluorine atom. Preferably, "A" is a straight, branched or cyclic $C_1$-$C_{20}$ alkylene, alkyltriyl or alkyltetrayl group, or $C_6$-$C_{30}$ arylene group. "B" is —CO—O—, —NHCO—O— or —NHCONH—.

The crosslinking acetal groups of formulae (A-2a) and (A-2b) are exemplified by the following formulae (A-2)-70 through (A-2)-77.

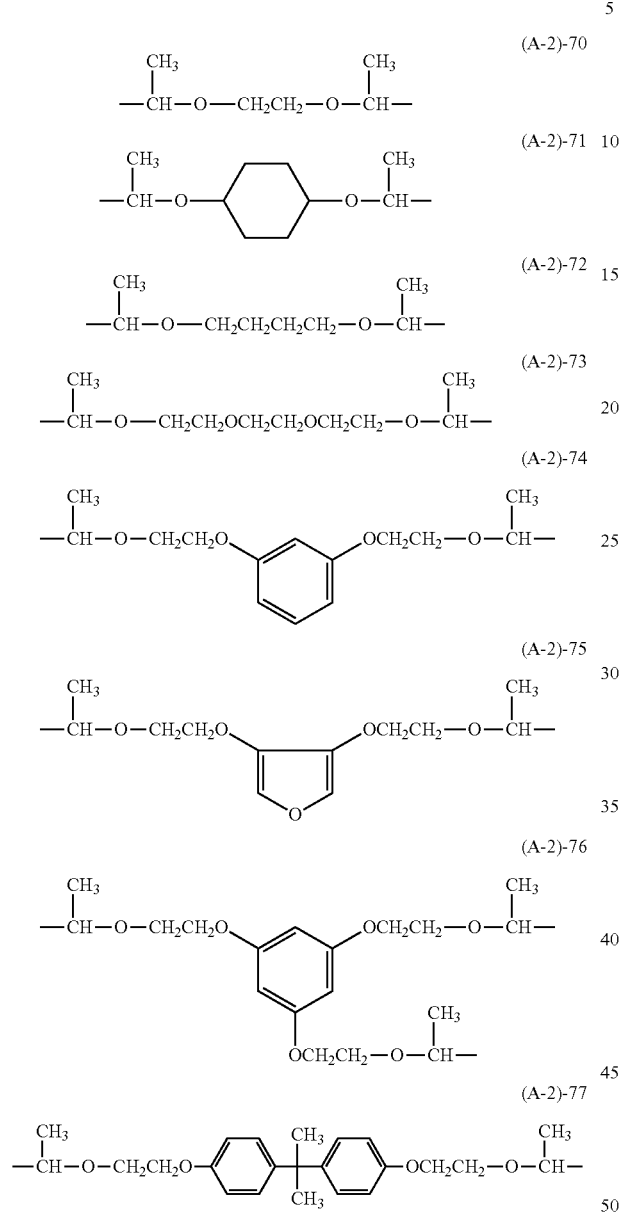

In formula (A-3), $R^{L5}$, $R^{L6}$ and $R^{L7}$ each are a monovalent hydrocarbon group, typically a straight, branched or cyclic $C_1$-$C_{20}$ alkyl group or straight, branched or cyclic $C_2$-$C_{20}$ alkenyl group, which may contain a heteroatom such as oxygen, sulfur, nitrogen or fluorine. A pair of $R^{L5}$ and $R^{L6}$, $R^{L5}$ and $R^{L7}$, or $R^{L6}$ and $R^{L7}$ may bond together to form a $C_3$-$C_{20}$ aliphatic ring with the carbon atom to which they are attached.

Exemplary tertiary alkyl groups of formula (A-3) include t-butyl, triethylcarbyl, 1-ethylnorbornyl, 1-methylcyclohexyl, 1-ethylcyclopentyl, 2-(2-methyl)adamantyl, 2-(2-ethyl)adamantyl, and t-pentyl.

Other exemplary tertiary alkyl groups include those of the following formulae (A-3)-1 to (A-3)-18.

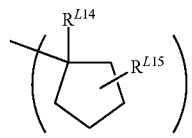 (A-3)-1

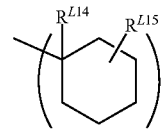 (A-3)-2

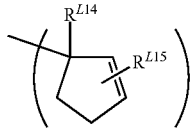 (A-3)-3

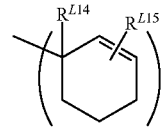 (A-3)-4

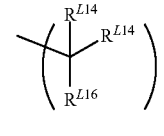 (A-3)-5

 (A-3)-6

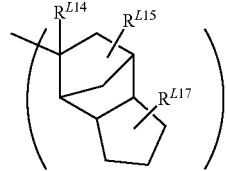 (A-3)-7

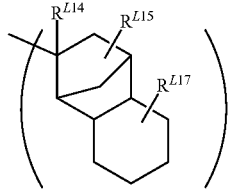 (A-3)-8

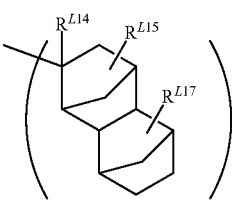 (A-3)-9

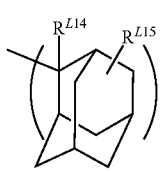 (A-3)-10

(A-3)-11

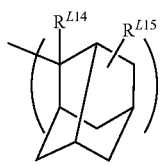

(A-3)-12

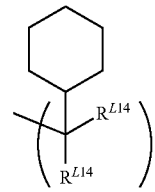

(A-3)-13

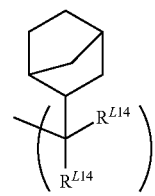

(A-3)-14

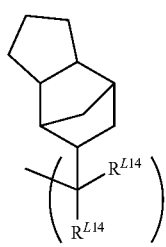

(A-3)-15

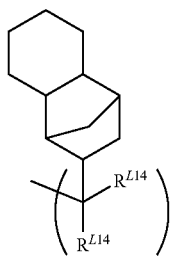

(A-3)-16

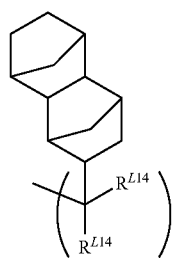

(A-3)-17

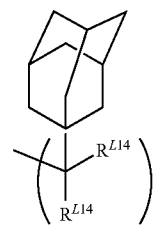

(A-3)-18

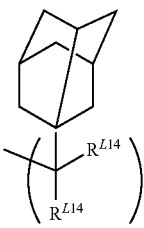

Herein $R^{L14}$ is each independently a straight, branched or cyclic $C_1$-$C_8$ alkyl group or $C_6$-$C_{20}$ aryl group, typically phenyl, $R^{L15}$ and $R^{L17}$ each are hydrogen or a straight, branched or cyclic $C_1$-$C_{20}$ alkyl group, and $R^{L16}$ is a $C_6$-$C_{20}$ aryl group, typically phenyl.

Also useful are acid labile groups having the following formulae (A-3)-19 and (A-3)-20. The polymer may be crosslinked within the molecule or between molecules with these acid labile groups.

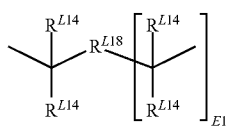

(A-3)-19

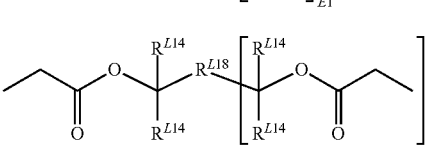

(A-3)-20

Herein $R^{L14}$ is as defined above, $R^{L18}$ is a (E1+1)-valent, straight, branched or cyclic $C_1$-$C_{20}$ aliphatic hydrocarbon group or $C_6$-$C_{20}$ aromatic hydrocarbon group, which may contain a heteroatom such as oxygen, sulfur or nitrogen, and E1 is an integer of 1 to 3.

Examples of the recurring units having an acid labile group of formula (A-3) include recurring units of (meth)acrylate having an exo-form structure represented by the formula (A-3)-21.

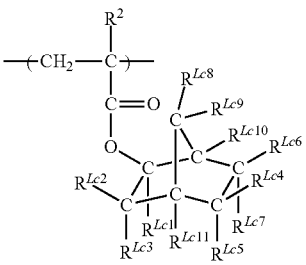

(A-3)-21

Herein $R^2$ is as defined above. $R^{Lc1}$ is a straight, branched or cyclic $C_1$-$C_8$ alkyl group or an optionally substituted $C_6$-$C_{20}$ aryl group. $R^{Lc2}$ to $R^{Lc7}$, $R^{Lc10}$ and $R^{Lc11}$ are each independently hydrogen or a monovalent $C_1$-$C_{15}$ hydrocarbon group which may contain a heteroatom. $R^{Lc8}$ and $R^{Lc9}$ are hydrogen. Alternatively, a pair of $R^{Lc2}$ and $R^{Lc3}$, $R^{Lc4}$ and $R^{Lc6}$, $R^{Lc4}$ and $R^{Lc7}$, $R^{Lc5}$ and $R^{Lc7}$, $R^{Lc5}$ and $R^{Lc11}$, $R^{Lc6}$ and $R^{Lc10}$, $R^{Lc8}$ and $R^{Lc9}$, or $R^{Lc9}$ and $R^{Lc10}$, taken together, may form a ring with the carbon atom to which they are attached, and a ring-forming participant is a divalent $C_1$-$C_{15}$ hydrocarbon group which may contain a heteroatom. Also, a pair of $R^{Lc2}$ and $R^{Lc11}$, $R^{Lc8}$ and $R^{Lc11}$, or $R^{Lc4}$ and $R^{Lc6}$ which are attached to vicinal carbon atoms may bond together directly to form a double bond. The formula also represents an enantiomer.

The monomers from which recurring units having formula (A-3)-21 are derived are exemplified in U.S. Pat. No. 6,448,420 (JP-A 2000-327633). Illustrative non-limiting examples of suitable monomers are given below. $R^2$ is as defined above.

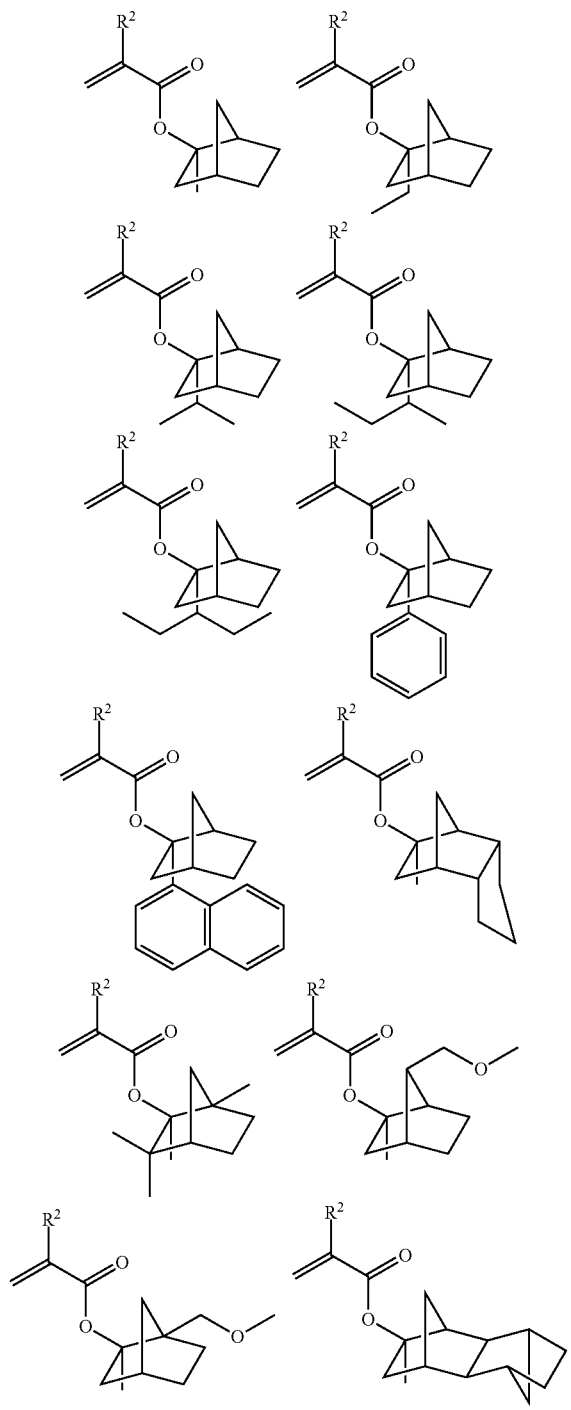

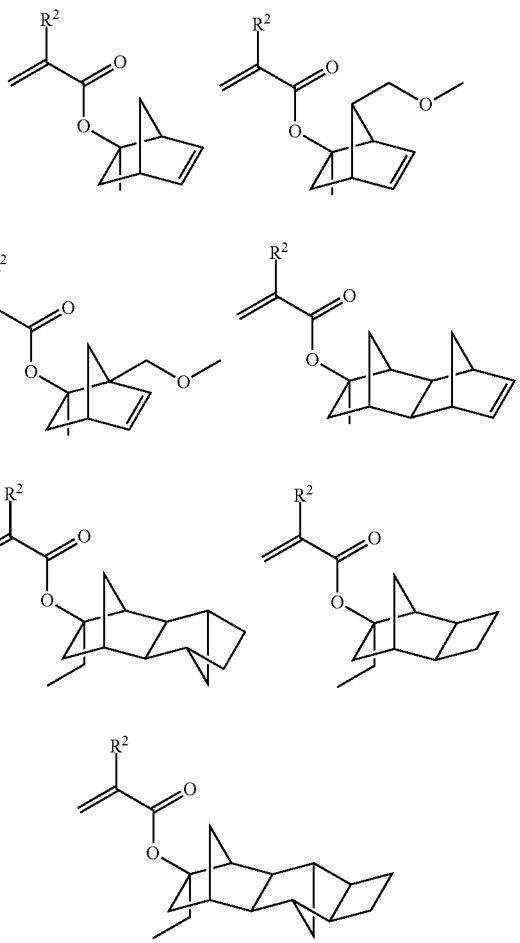

The recurring units having an acid labile group of formula (A-3) include those units derived from (meth)acrylates having furandiyl, tetrahydrofurandiyl or oxanorbornanediyl, represented by the formula (A-3)-22.

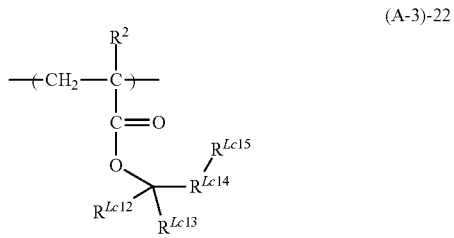

(A-3)-22

Herein $R^2$ is as defined above. $R^{Lc12}$ and $R^{Lc13}$ are each independently a monovalent, straight, branched or cyclic $C_1$-$C_{10}$ hydrocarbon group, or $R^{Lc12}$ and $R^{Lc13}$, taken together, may form an aliphatic ring with the carbon atom to which they are attached. $R^{Lc14}$ is furandiyl, tetrahydrofurandiyl or oxanorbornanediyl. $R^{Lc15}$ is hydrogen or a monovalent, straight, branched or cyclic $C_1$-$C_{10}$ hydrocarbon group which may contain a heteroatom.

Examples of the monomers from which the recurring units having formula (A-3)-22 are derived are shown below, but not limited thereto.

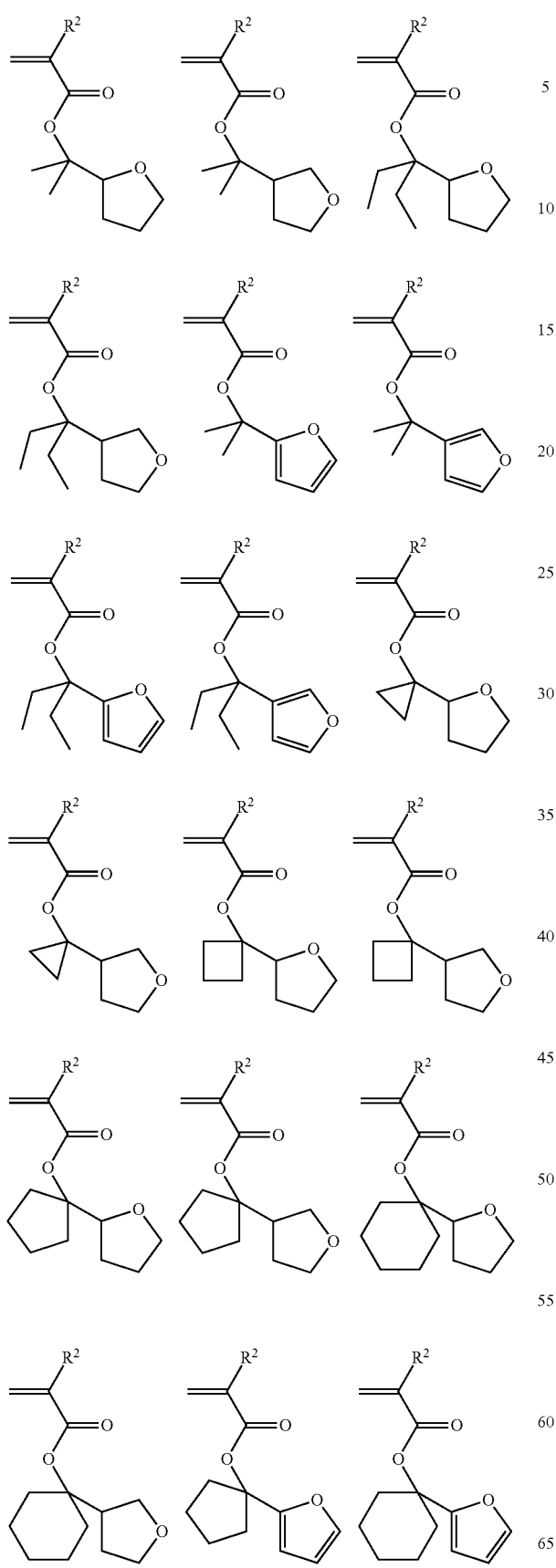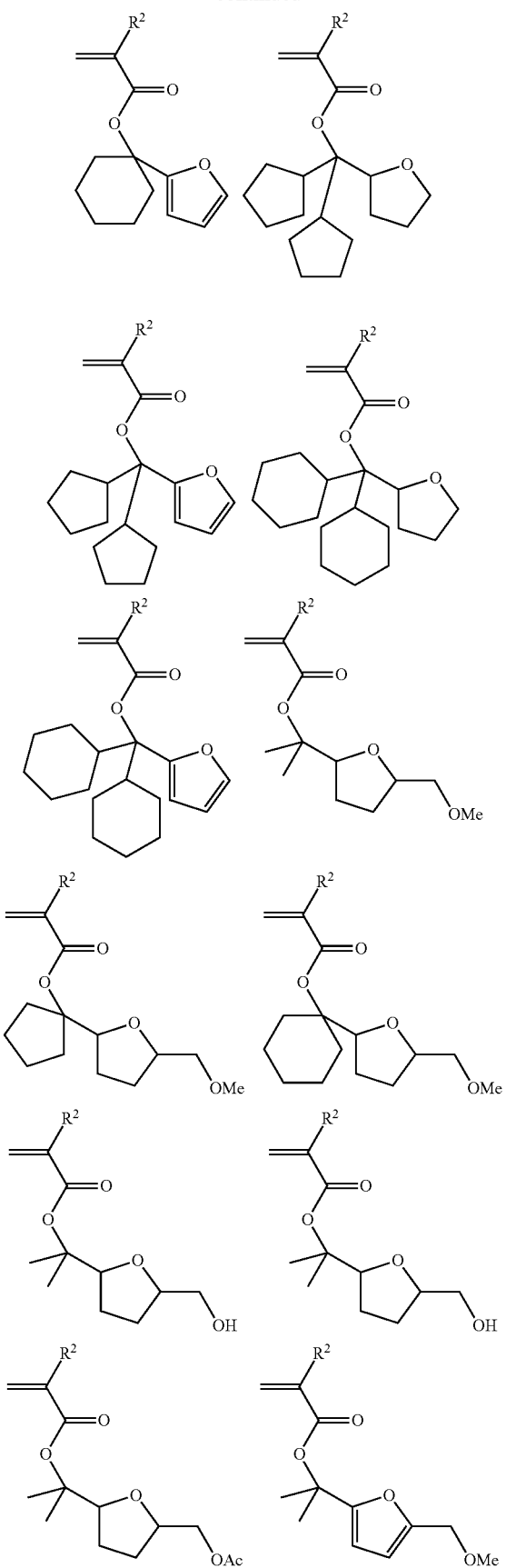

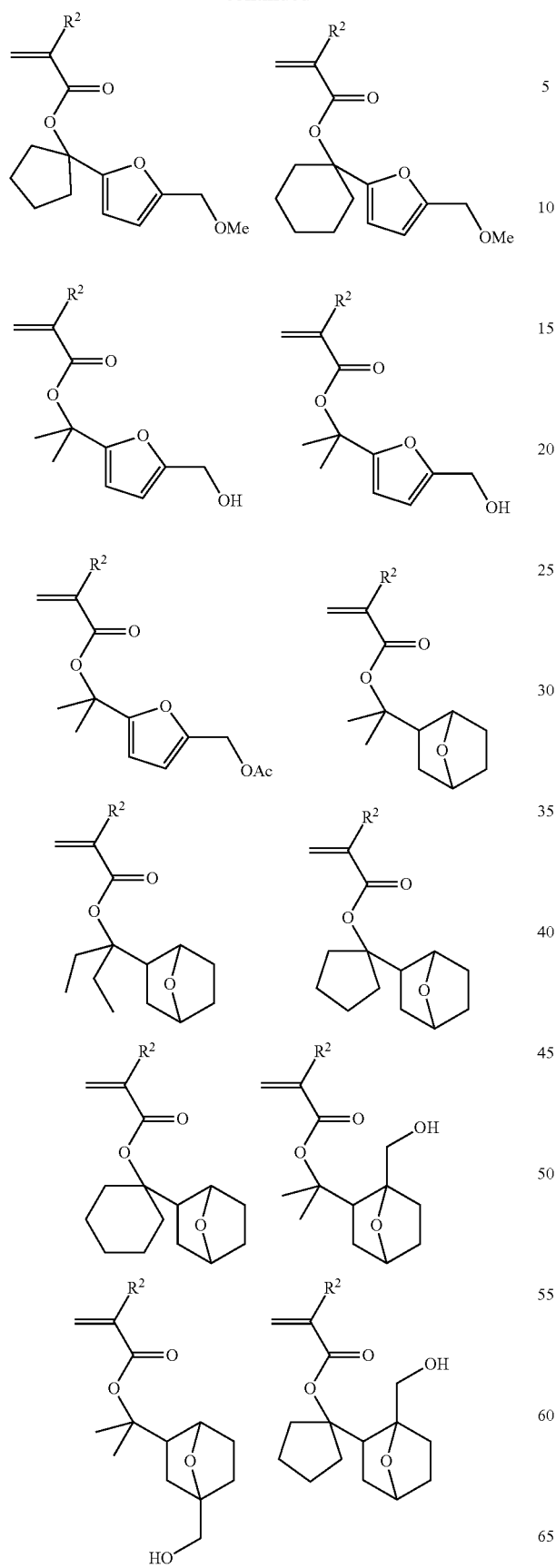
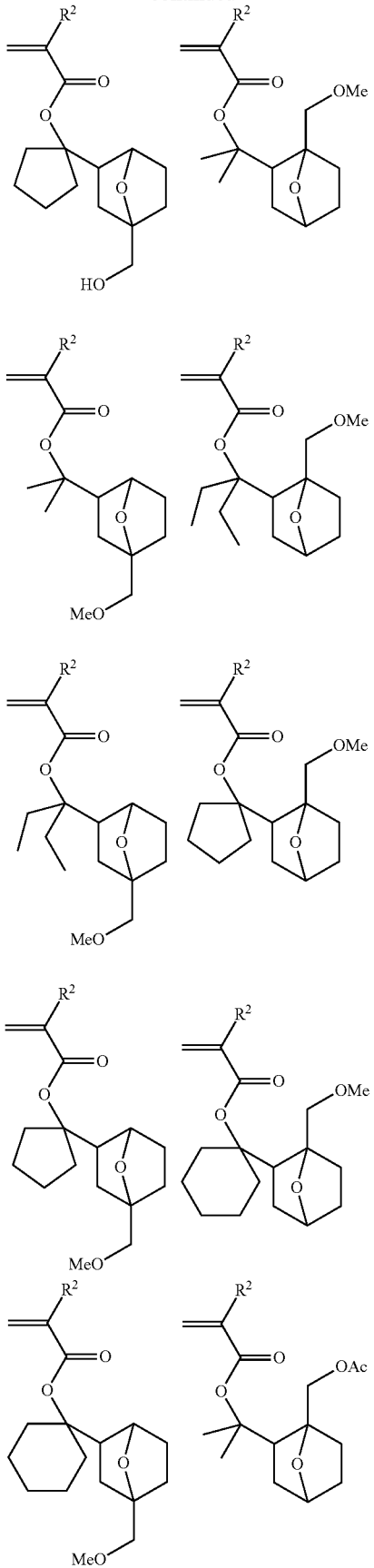

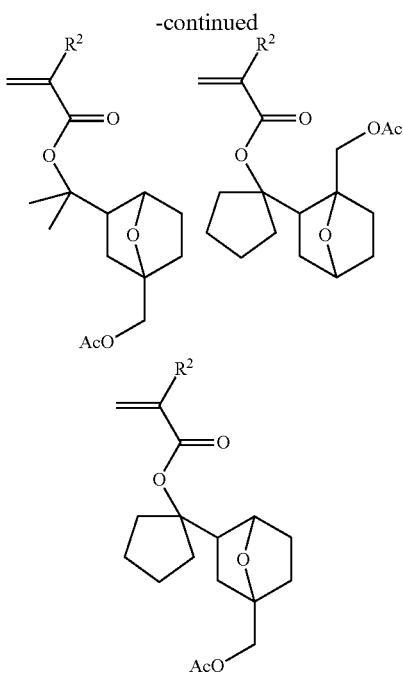

Monomers containing an acid labile group other than the foregoing are exemplified in U.S. Pat. No. 9,335,633 (JP-A 2015-166833, paragraphs [0061]-[0085]).

The base resin may further comprise recurring units of at least one type selected from the formulae (b1), (b2) and (b3), which are simply referred to as units (b1), (b2) and (b3).

(b1)

(b2)

(b3)

Herein $R^{101}$, $R^{105}$, and $R^{110}$ each are hydrogen or methyl. $R^{102}$ is a single bond, phenylene, —O—$R^{114}$—, or —C(=O)—Y—$R^{114}$—, wherein Y is —O— or —NH—, and $R^{114}$ is a $C_1$-$C_6$ straight, branched or cyclic alkylene group, phenylene group or $C_3$-$C_{10}$ straight, branched or cyclic alkenylene group, which may contain a carbonyl, ester, ether or hydroxyl moiety. $R^{103}$, $R^{104}$, $R^{107}$, $R^{108}$, $R^{109}$, $R^{111}$, $R^{112}$, and $R^{113}$ are each independently a $C_1$-$C_{12}$ straight, branched or cyclic alkyl group which may contain a carbonyl, ester or ether moiety, or a $C_6$-$C_{12}$ aryl, $C_7$-$C_{20}$ aralkyl, or mercaptophenyl group in which at least one hydrogen (one or more or even all hydrogen atoms) may be replaced by a $C_1$-$C_{10}$ straight, branched or cyclic alkyl, halogen, trifluoromethyl, cyano, nitro, hydroxyl, alkoxy, alkoxycarbonyl or acyloxy moiety. $R^{106}$ is hydrogen or trifluoromethyl. $Z^1$ is a single bond or —C(=O)—$Z^3$—$R^{115}$—. $Z^2$ is a single bond, methylene, ethylene, phenylene, fluorinated phenylene, —O—$R^{115}$— or —C(=O)—$Z^3$—$R^{115}$—, wherein $Z^3$ is —O— or —NH—, and $R^{115}$ is a $C_1$-$C_6$ straight, branched or cyclic alkylene group, phenylene group, or $C_1$-$C_6$ straight, branched or cyclic alkenylene group, which may contain a carbonyl, ester, ether or hydroxyl moiety. A pair of $R^{103}$ and $R^{104}$, $R^{107}$ and $R^{108}$, $R^{107}$ and $R^{109}$, $R^{108}$ and $R^{109}$, $R^{111}$ and $R^{112}$, $R^{111}$ and $R^{113}$, or $R^{112}$ and $R^{113}$ may bond directly or via a methylene moiety or ether bond to form a ring with the sulfur atom to which they are attached. $Q^-$ is a non-nucleophilic counter ion, b1, b2 and b3 are numbers in the range of $0 \le b1 \le 0.5$, $0 \le b2 \le 0.5$, $0 \le b3 \le 0.5$, and $0 < b1+b2+b3 \le 0.5$.

The binding of the acid generator to the polymer backbone is effective for shortening the distance of acid diffusion and reducing LWR.

The inclusion of recurring units (b1), (b2) or (b3) in the base resin is effective for increasing the sensitivity of the resist film by the mechanism that the metal in the salt having formula (1) emits secondary electrons during exposure, which induce decomposition of the acid generator in unit (b1), (b2) or (b3). Although a sensitivity increase can be achieved by elevating the PEB temperature or prolonging the PEB time, the acid diffusion distance is increased in either case, resulting in exaggerated LWR. In contrast, the addition of the salt having formula (1) ensures a high sensitivity and low LWR because of suppressed acid diffusion and a high efficiency of acid generation. Of the recurring units (b1), (b2) and (b3), units (b2) are most preferred.

Examples of the monomer from which recurring units (b1) are derived are shown below, but not limited thereto. $Q^-$ is as defined above.

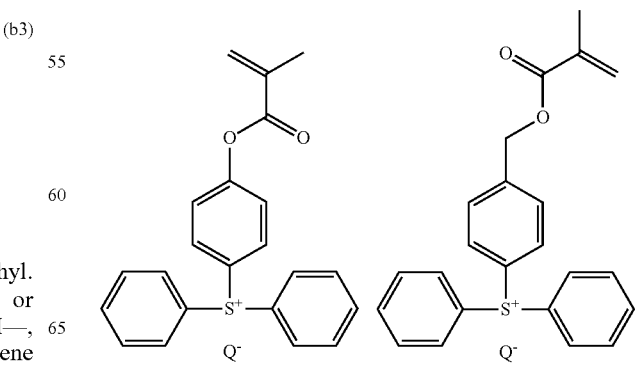

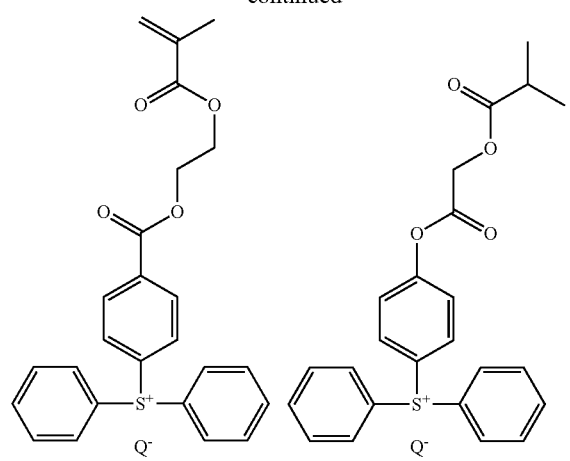
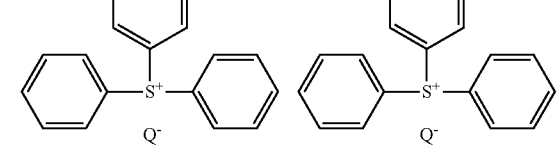
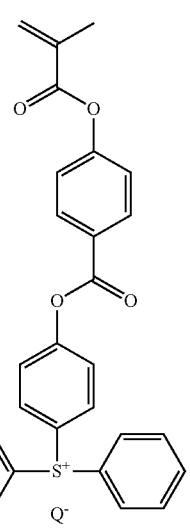
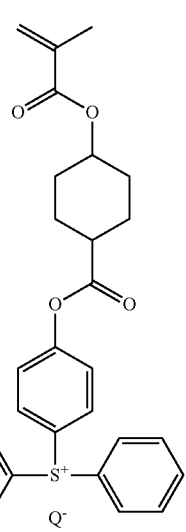
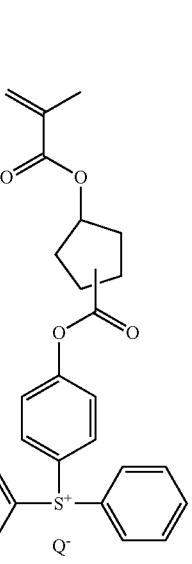

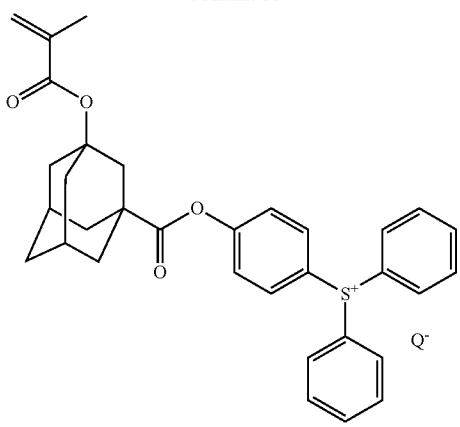
Examples of the monomer from which recurring units (b2) are derived are shown below, but not limited thereto.
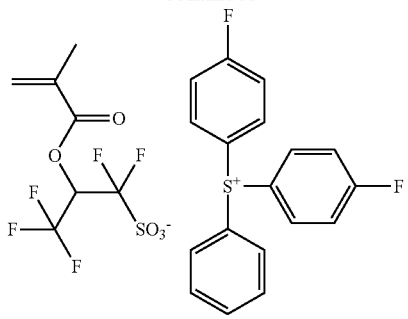
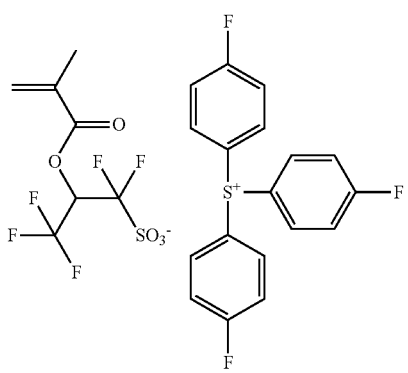
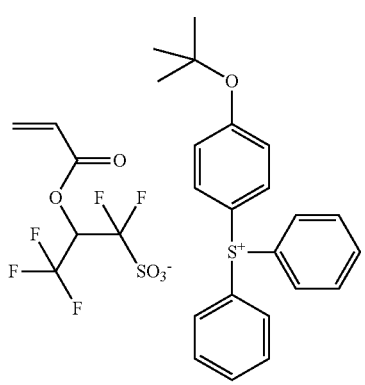
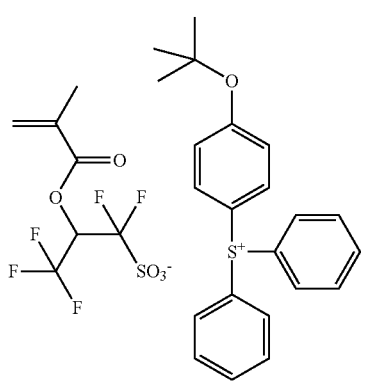

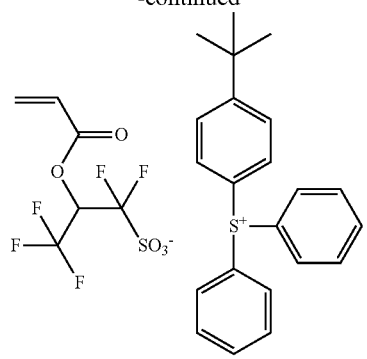
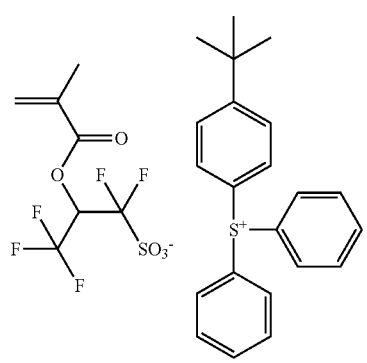
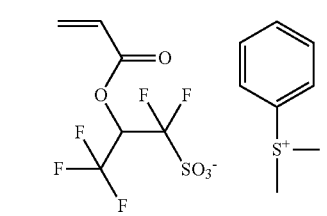
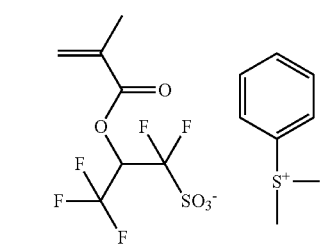
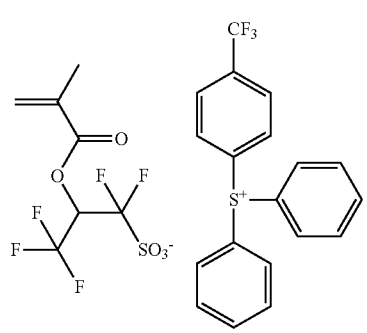
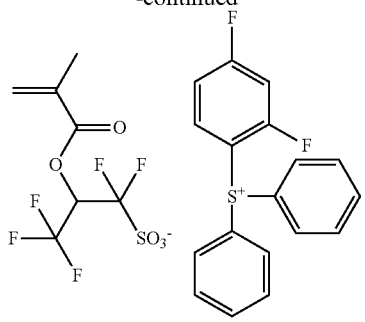
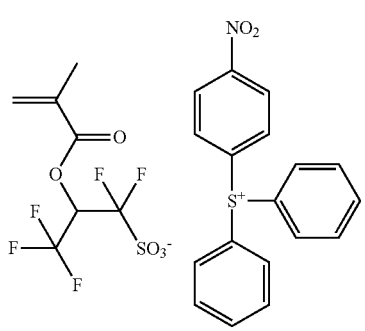
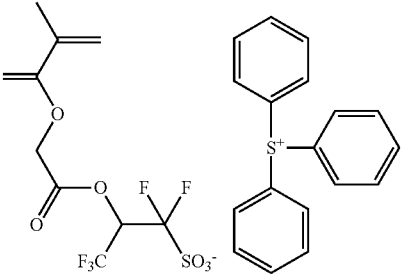
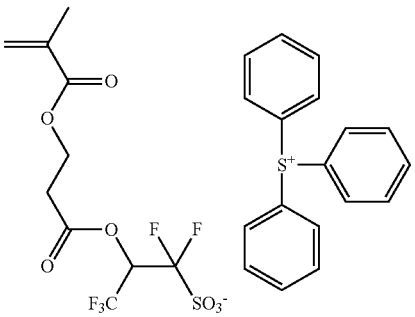
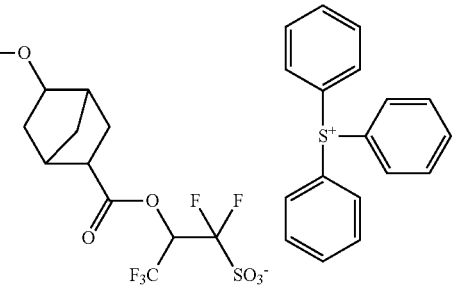

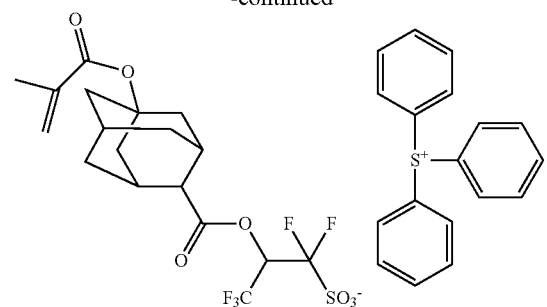
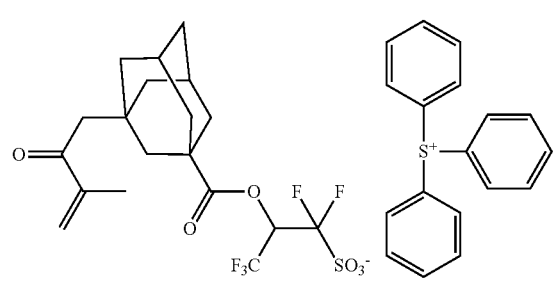
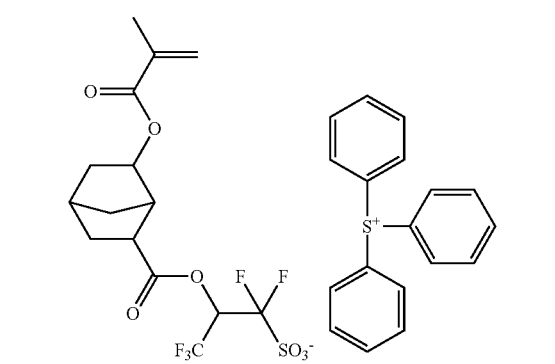
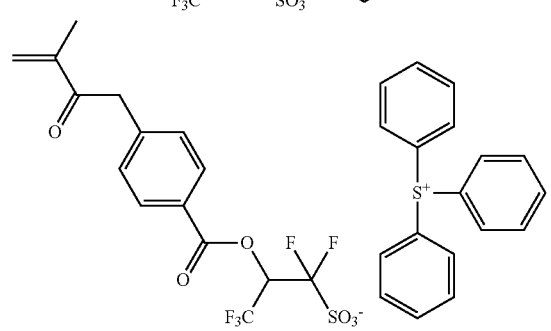
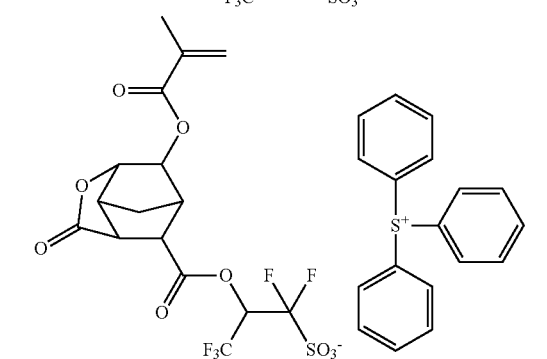
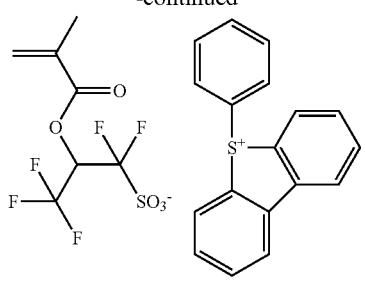
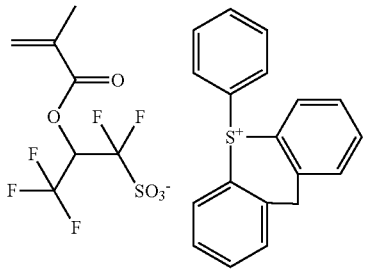
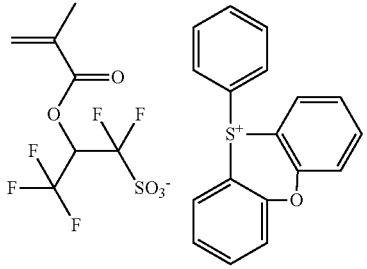
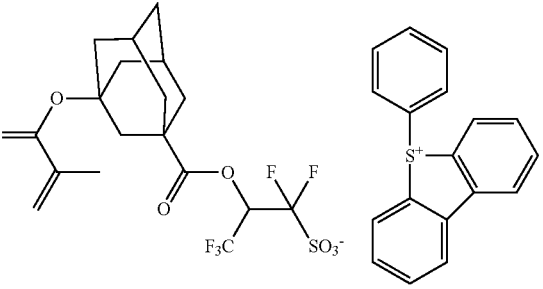
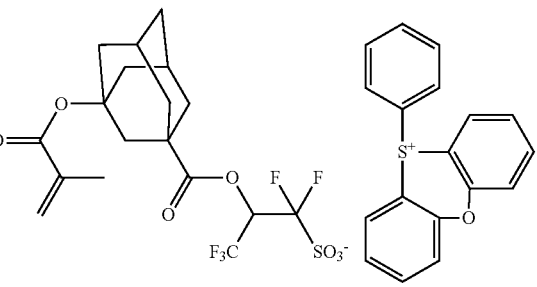
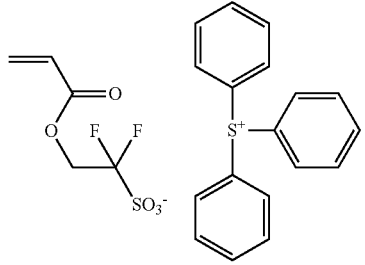

-continued
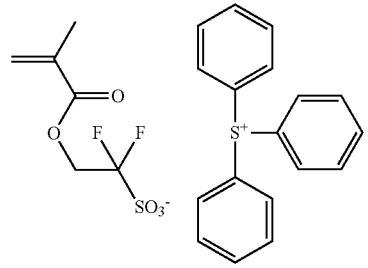
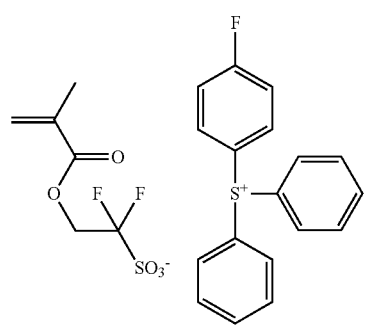
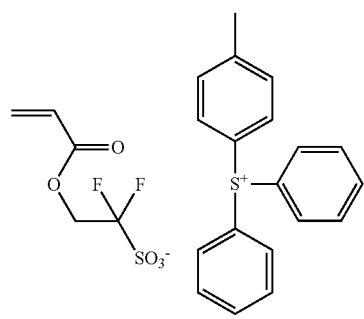
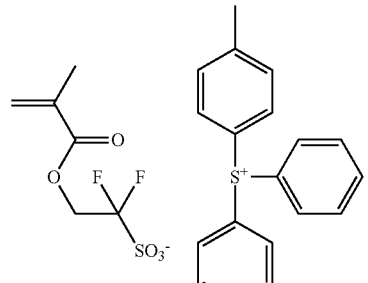
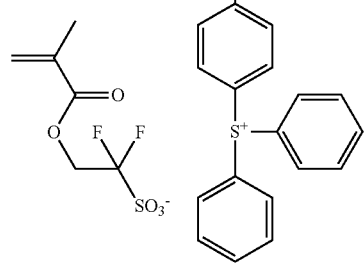
-continued
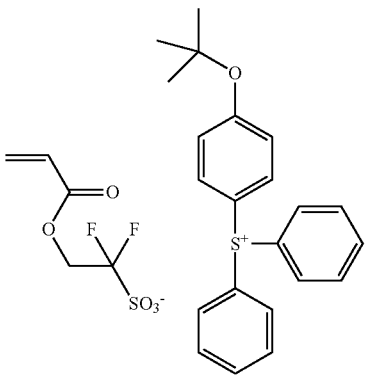
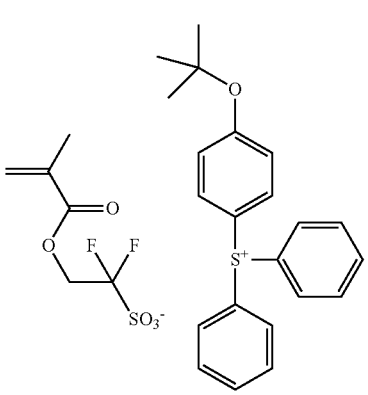
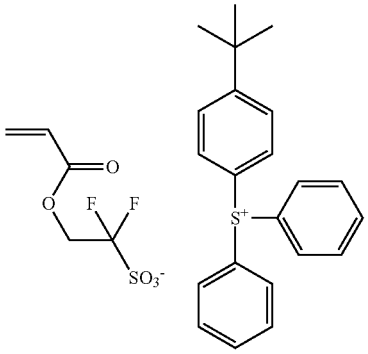
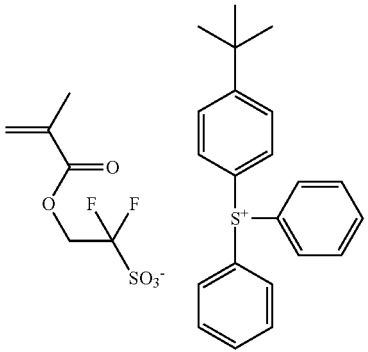
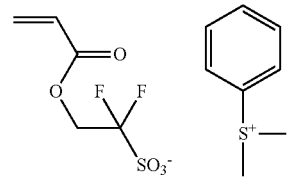

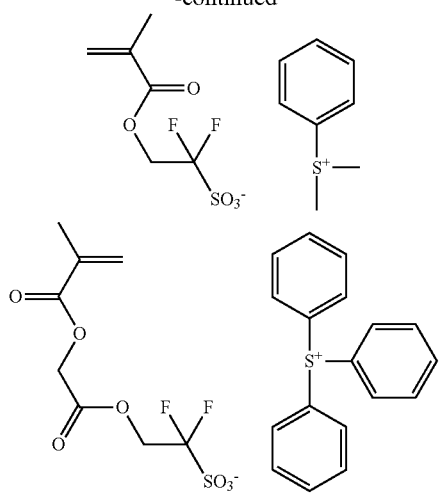
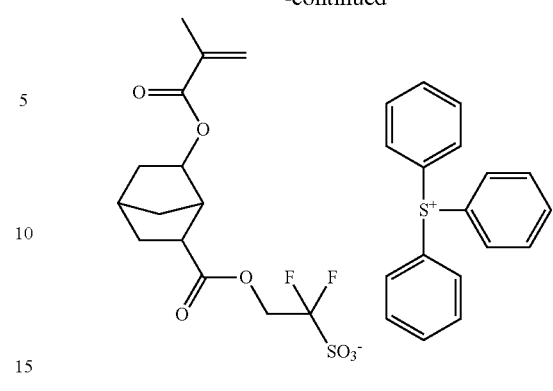
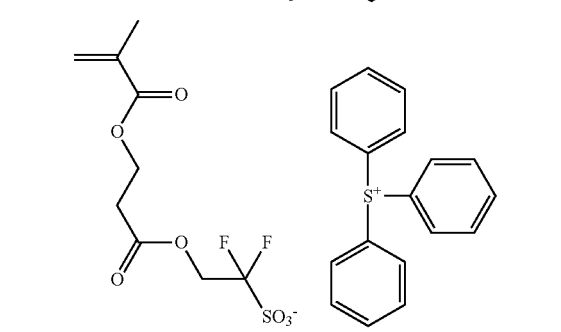
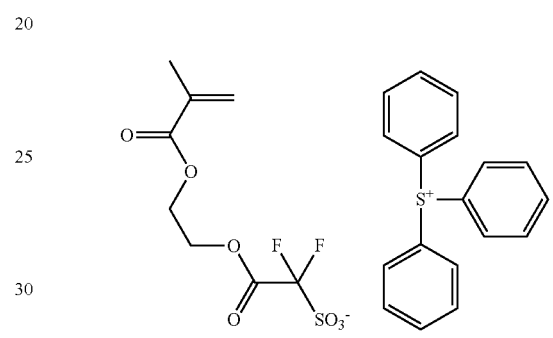
Examples of the monomer from which recurring units (b3) are derived are shown below, but not limited thereto.
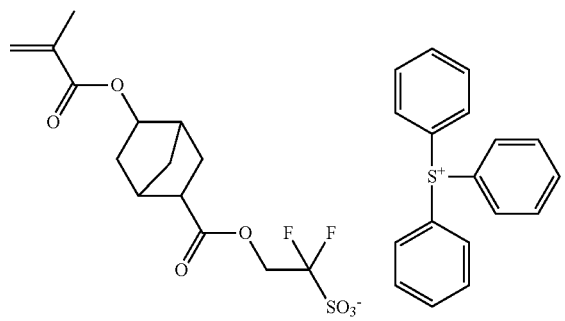
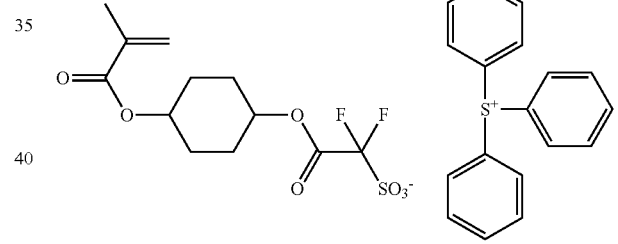
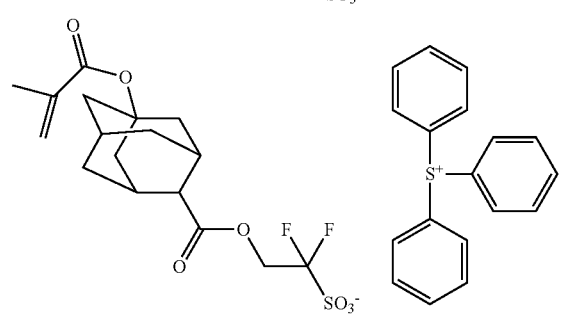
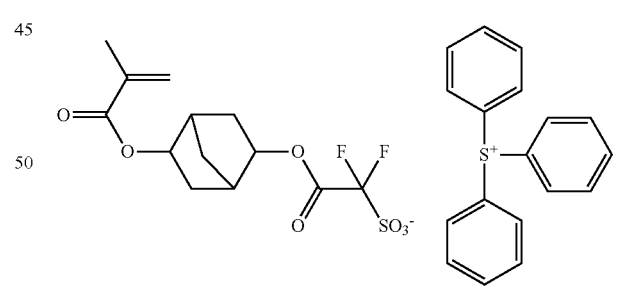
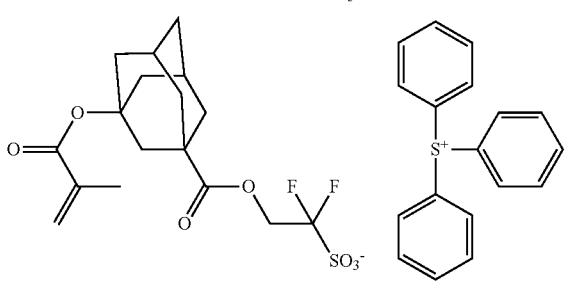
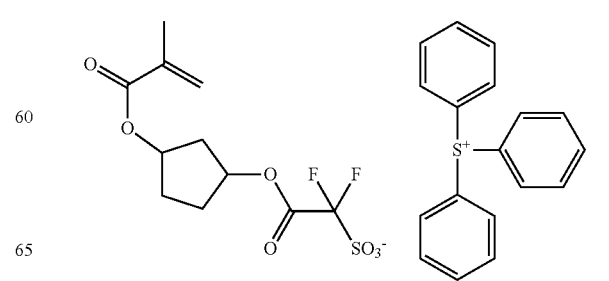

105
-continued
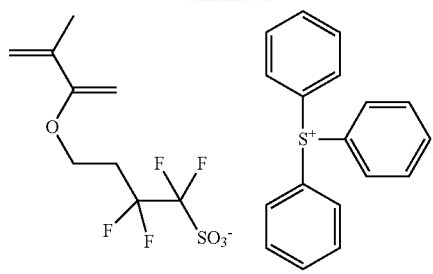
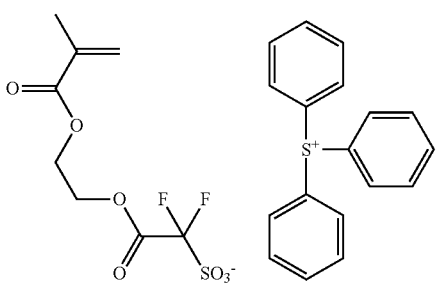
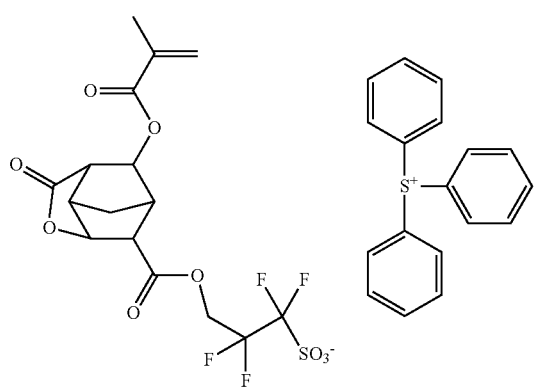
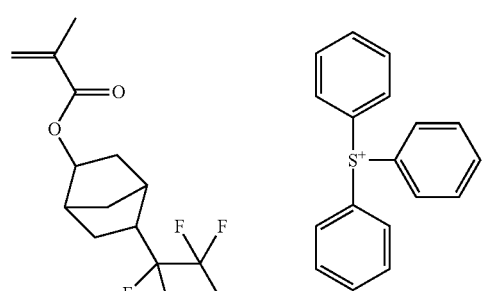
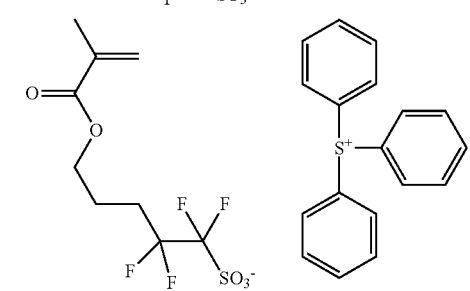
106
-continued
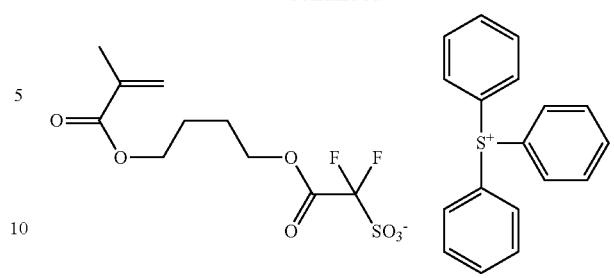
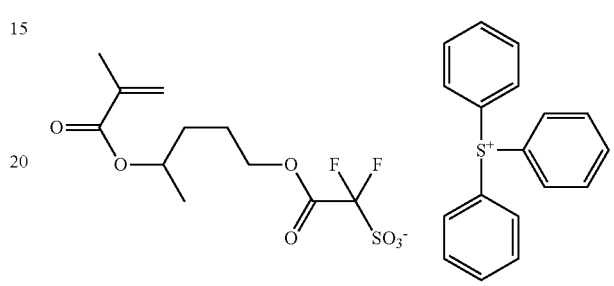
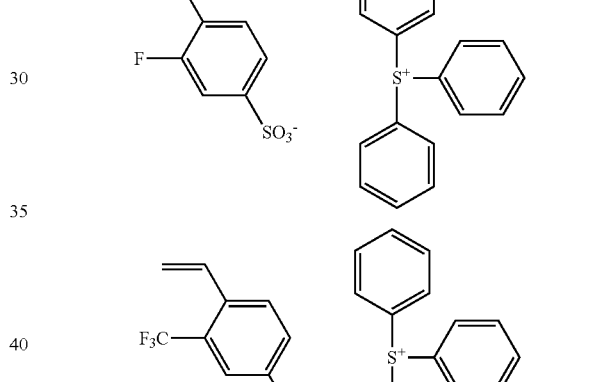
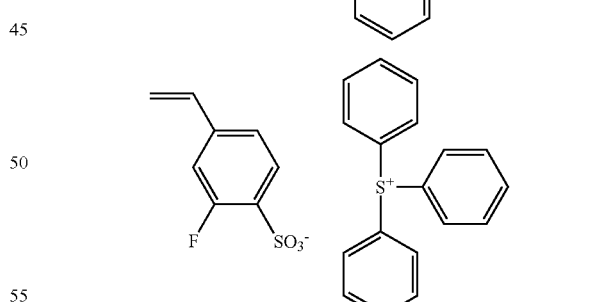
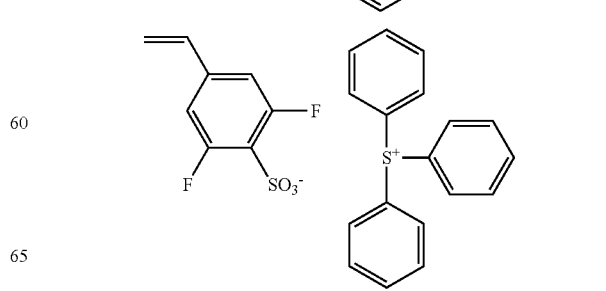

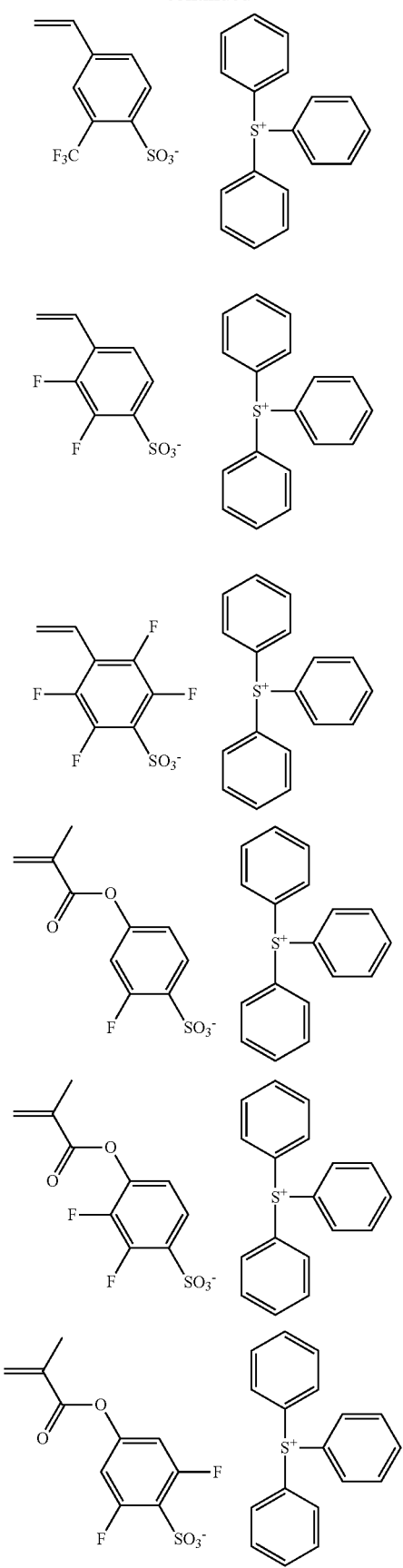

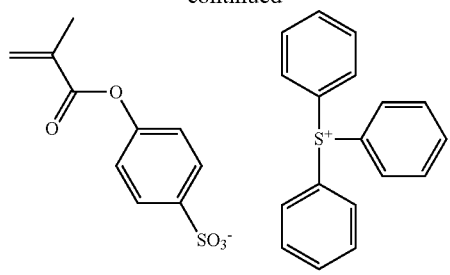
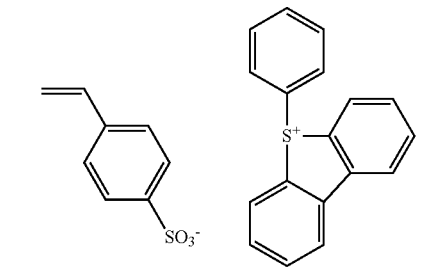
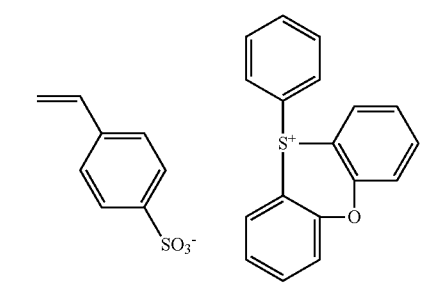
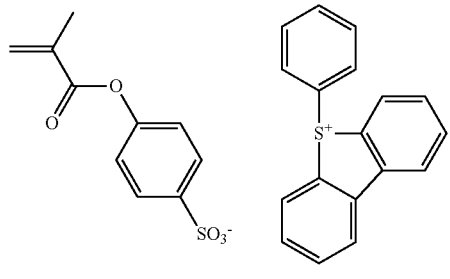
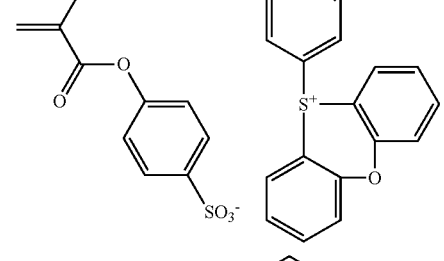
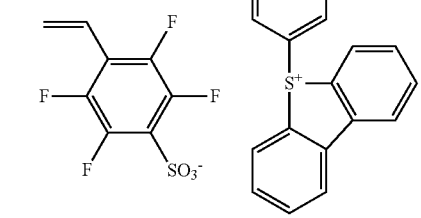
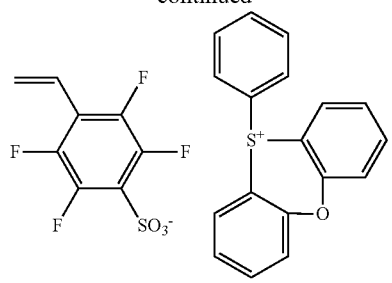
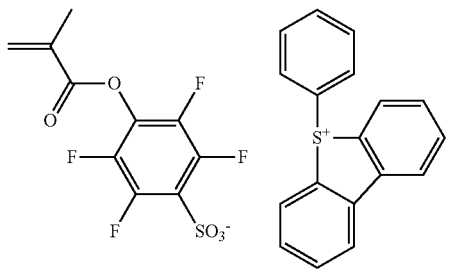
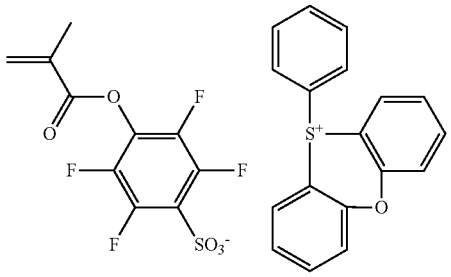
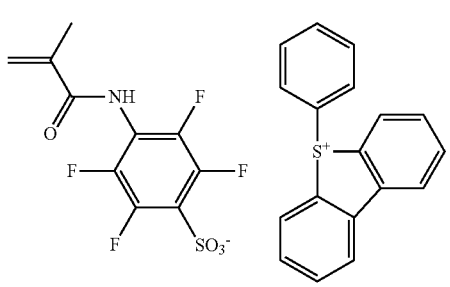
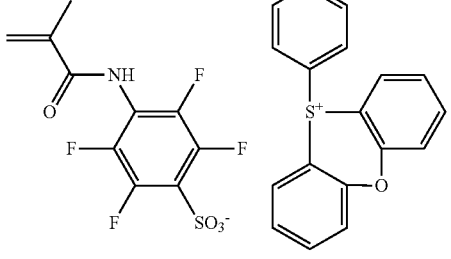
In the base resin, recurring units (c) having a phenolic hydroxyl group as the adhesive group may be further incorporated. Examples of the monomer from which recurring units (c) are derived are shown below, but not limited thereto.

111
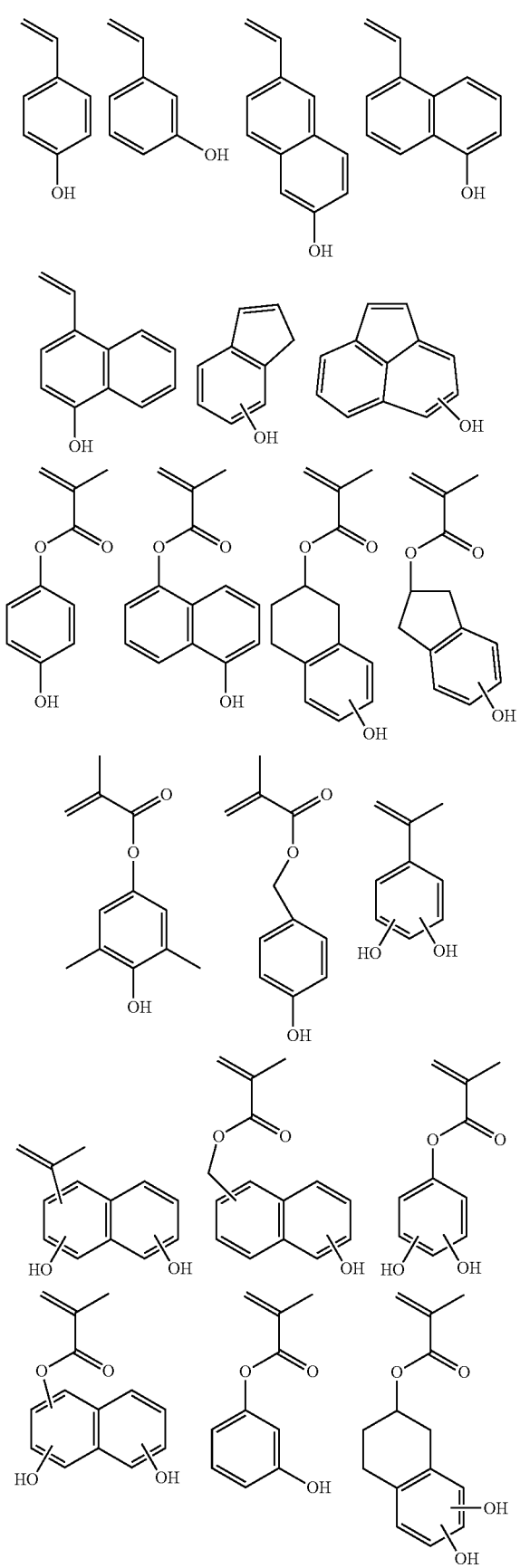
112
-continued
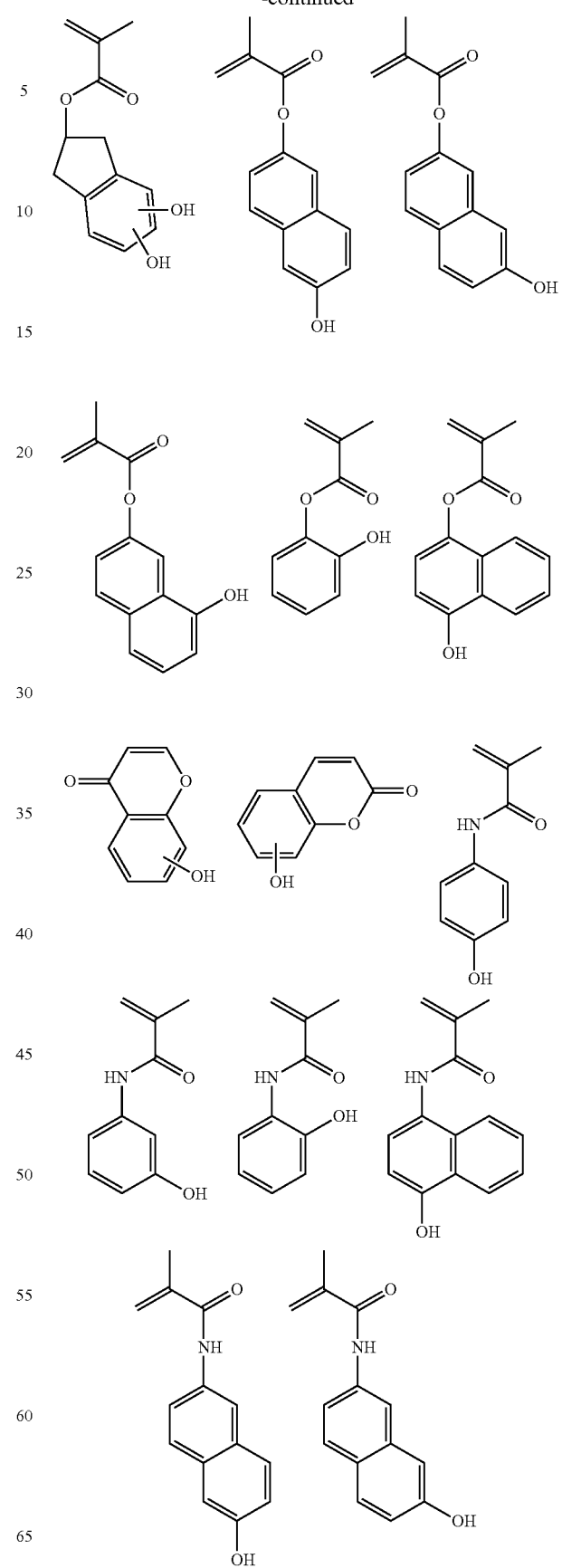

113
-continued
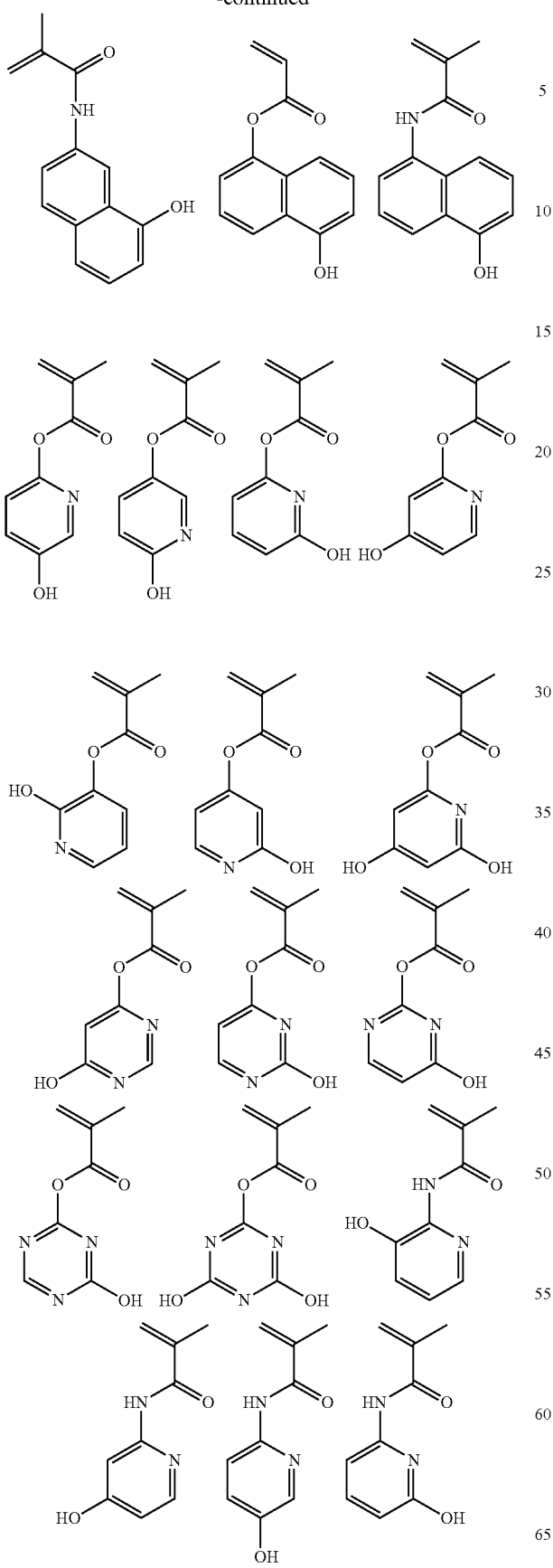
114
-continued
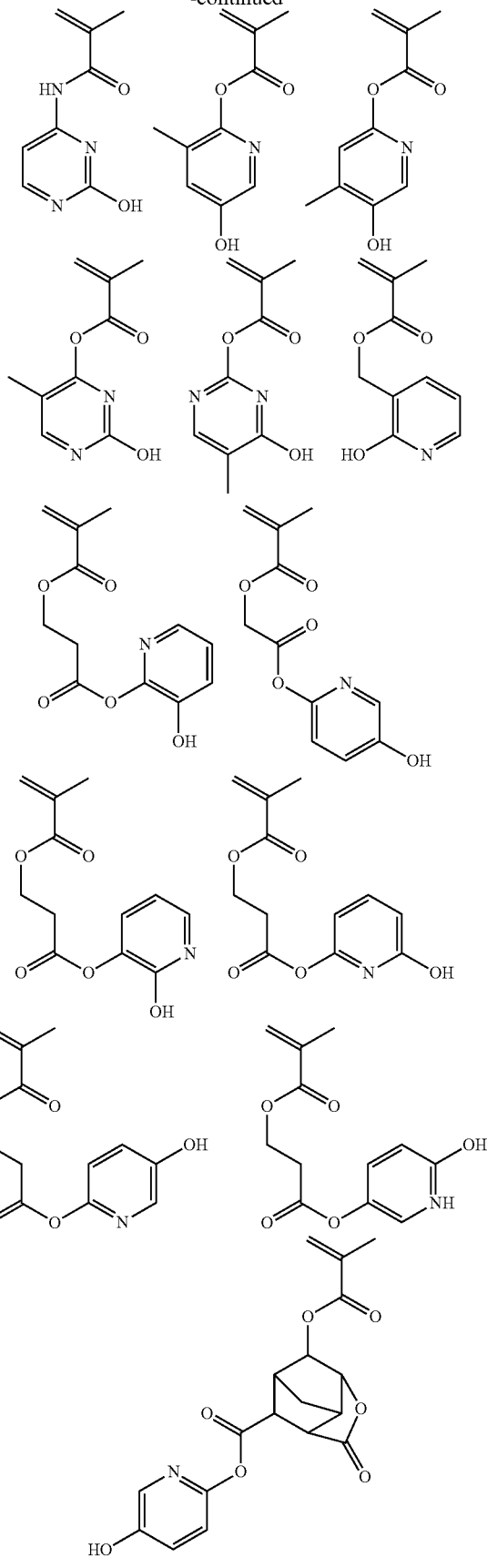

Recurring units (d) having another adhesive group may also be incorporated in the base resin. Examples of the other adhesive group include hydroxyl (other than the phenolic hydroxyl), carboxyl, lactone ring, carbonate, thiocarbonate, carbonyl, cyclic acetal, ether, ester, sulfonic acid ester, cyano, amide, and —O—C(=O)-G- wherein G is sulfur or NH. Examples of the monomer from which recurring units (d) are derived are shown below, but not limited thereto.

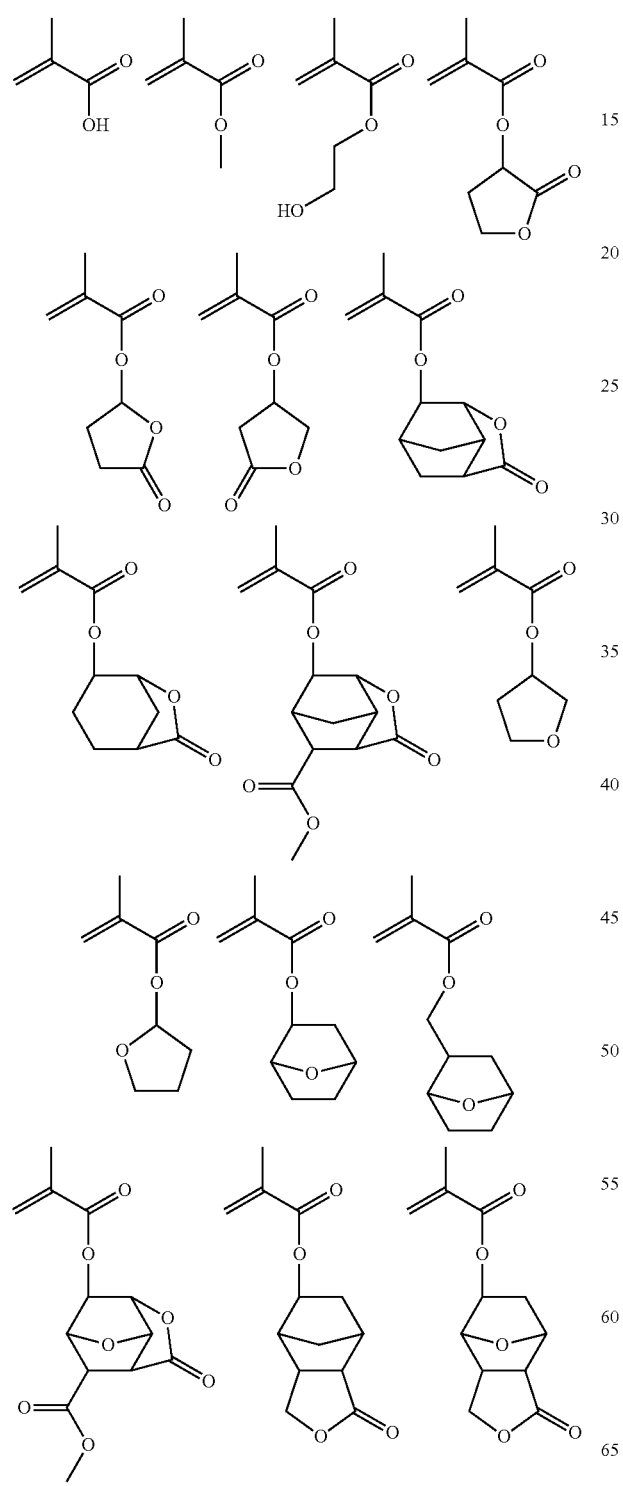

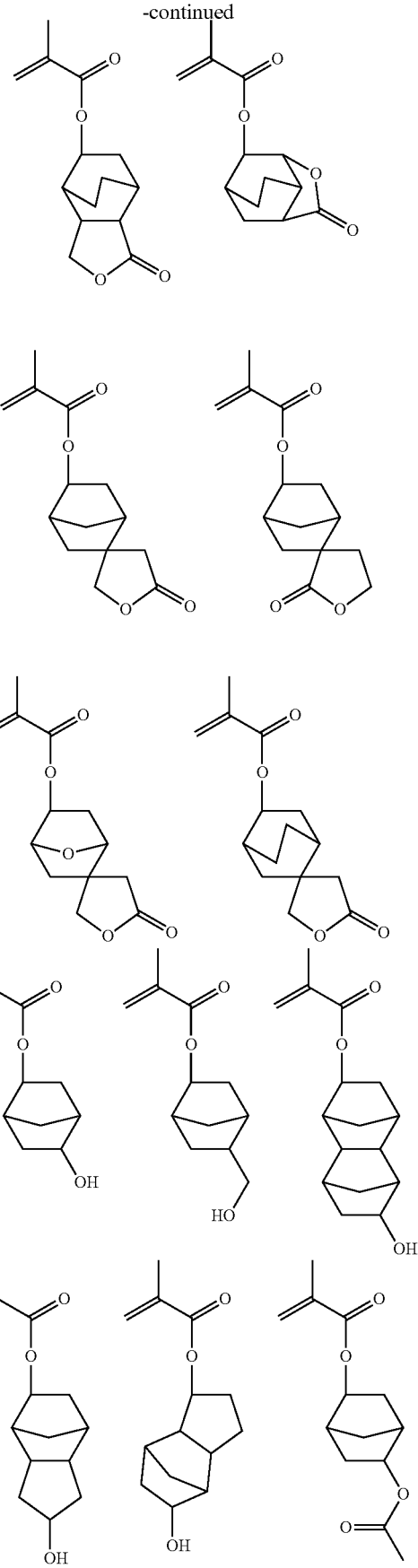

-continued

117
-continued
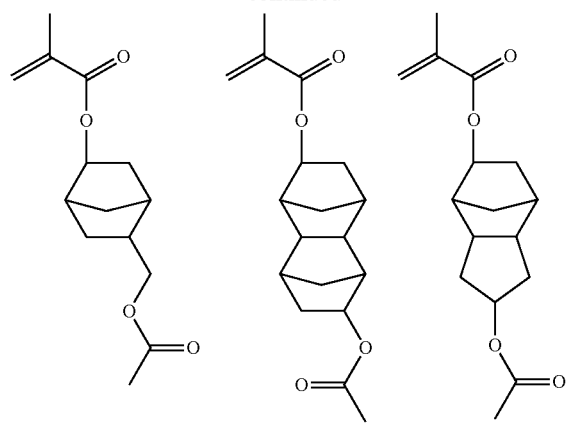
118
-continued
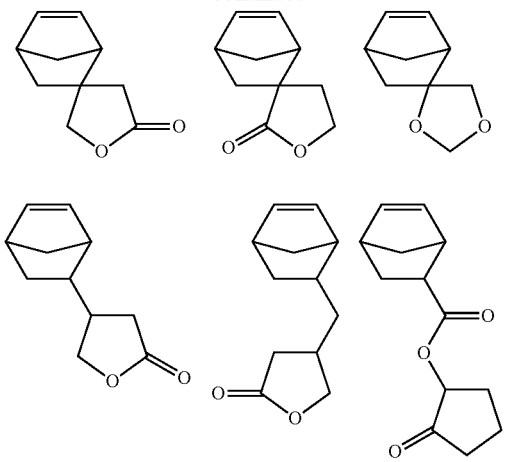
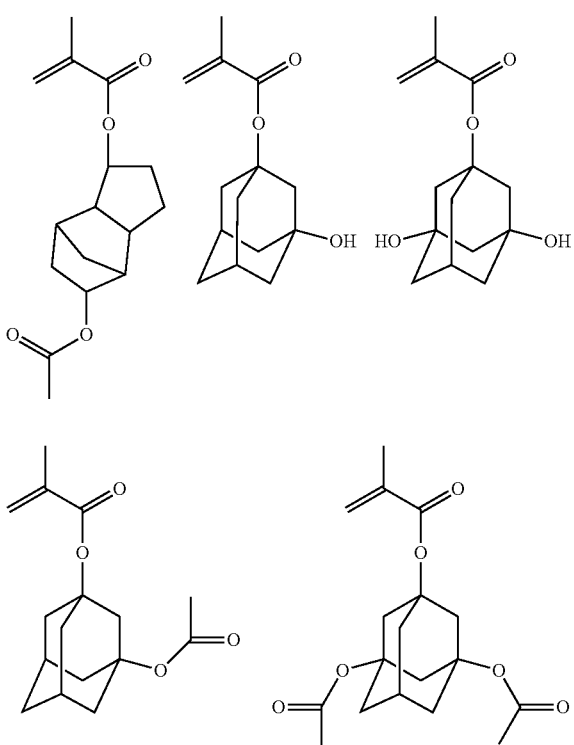
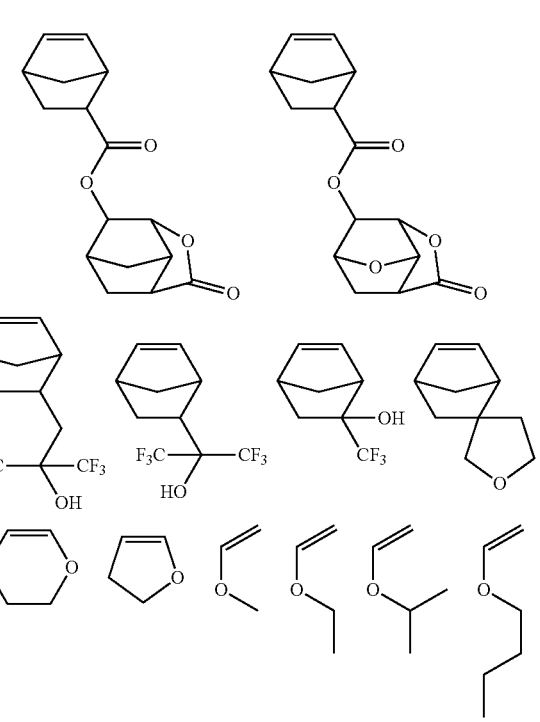
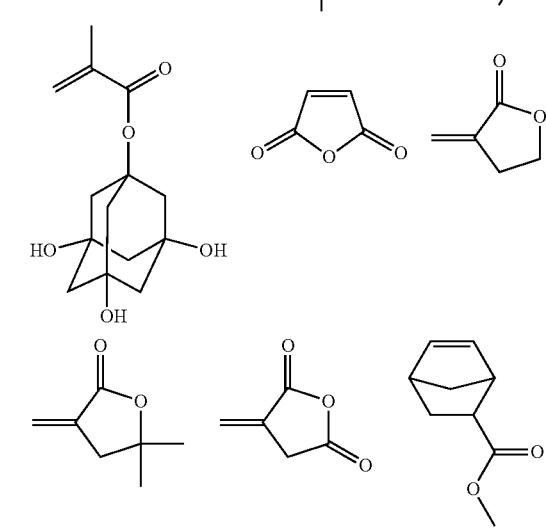
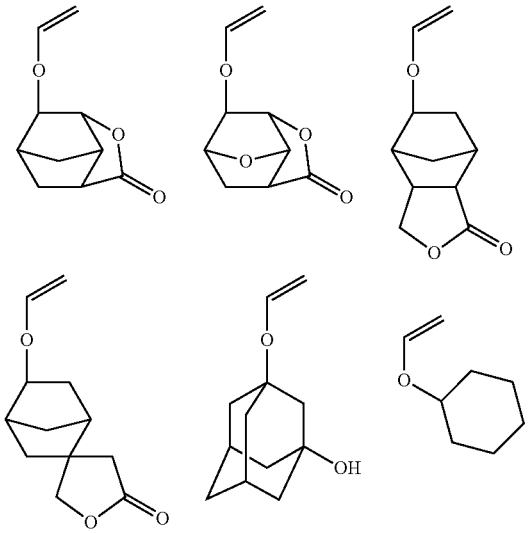

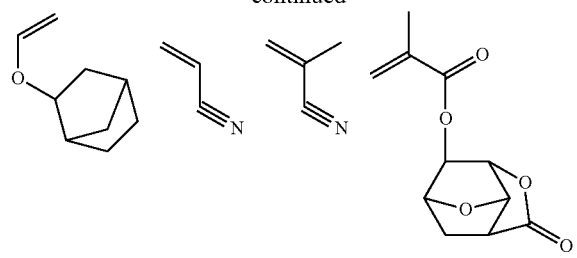
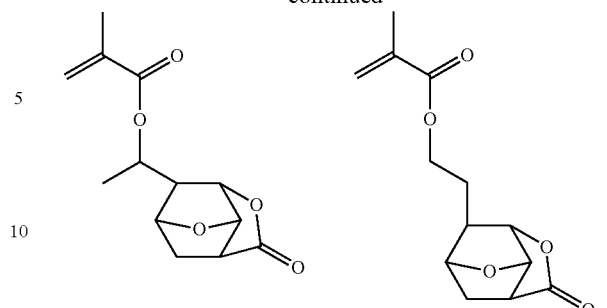
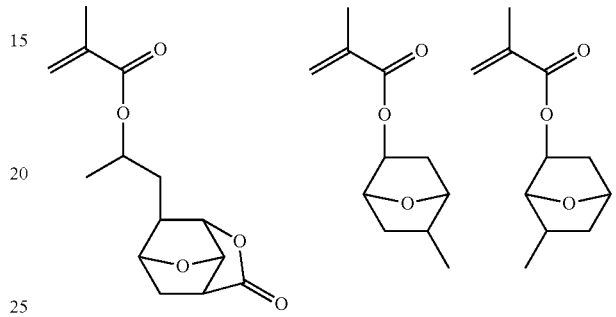
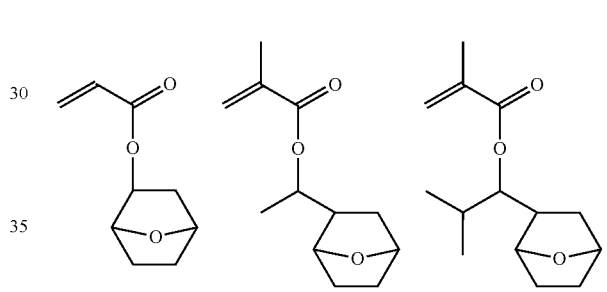
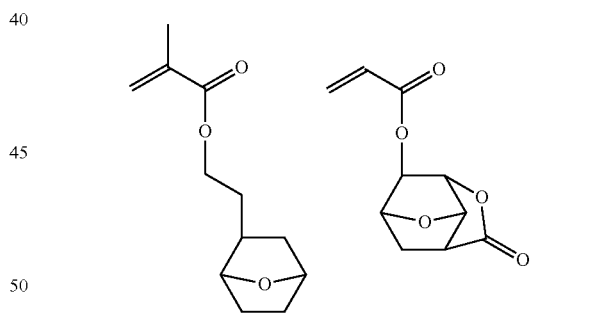
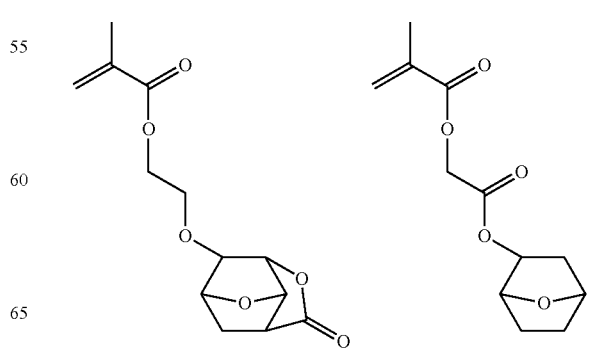

121
-continued
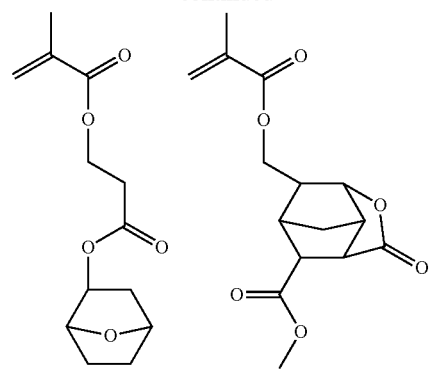
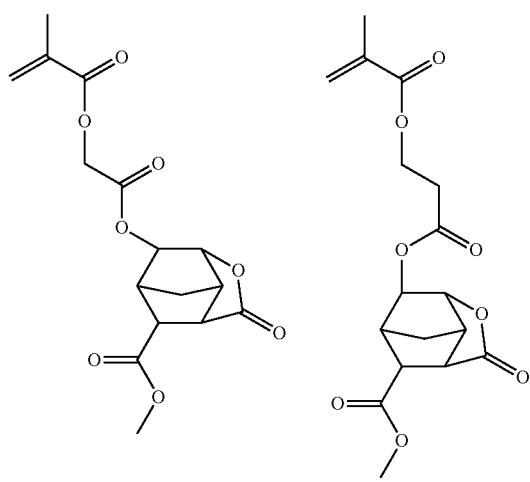
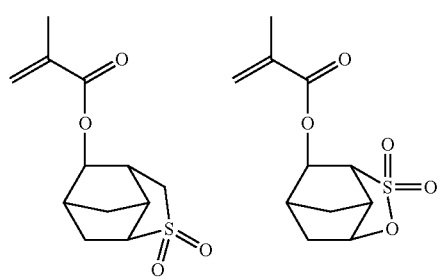
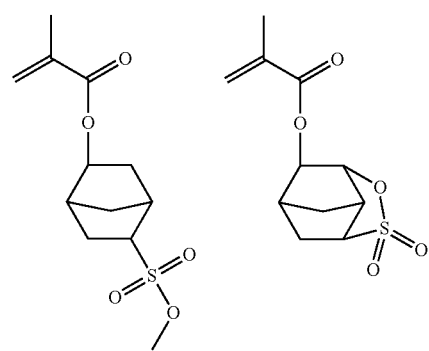
122
-continued
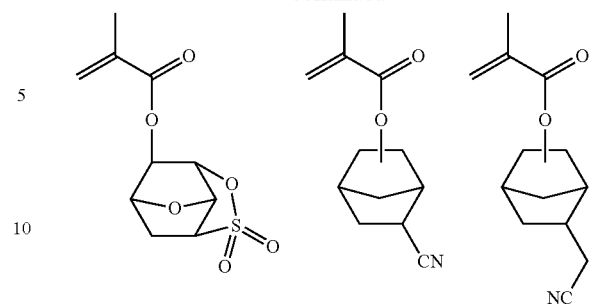
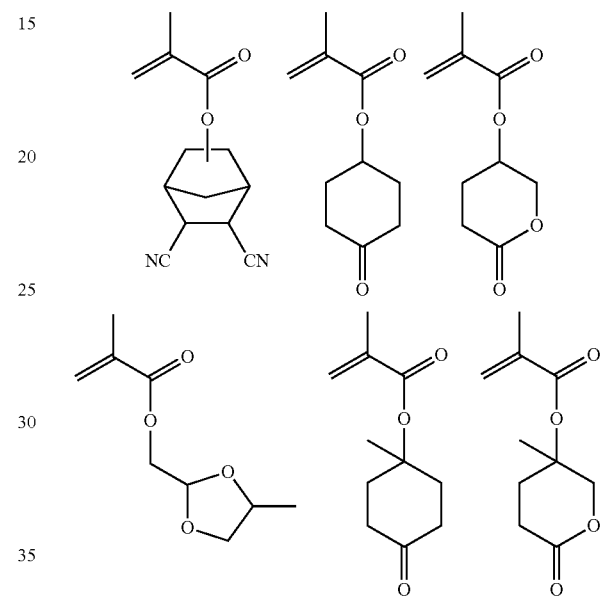
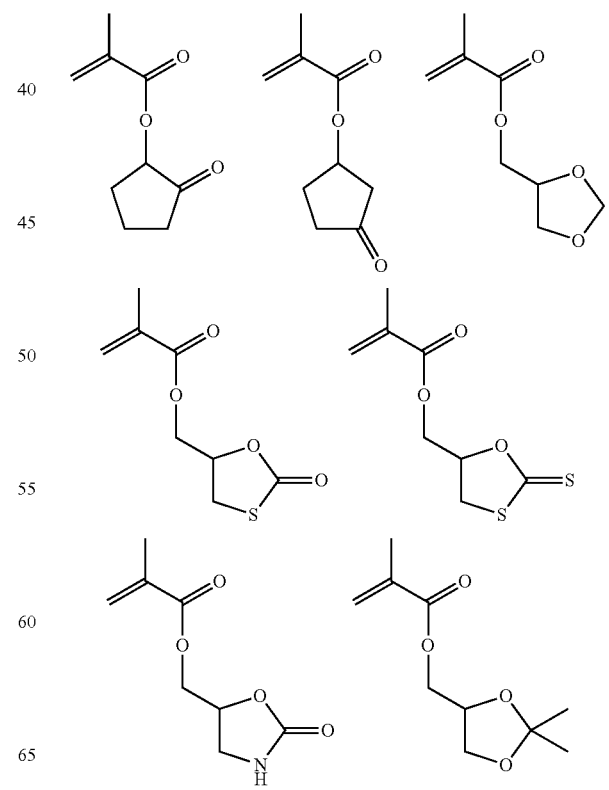

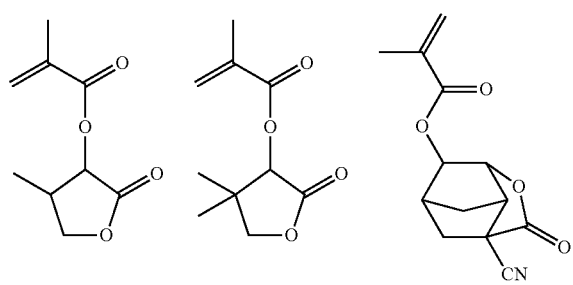
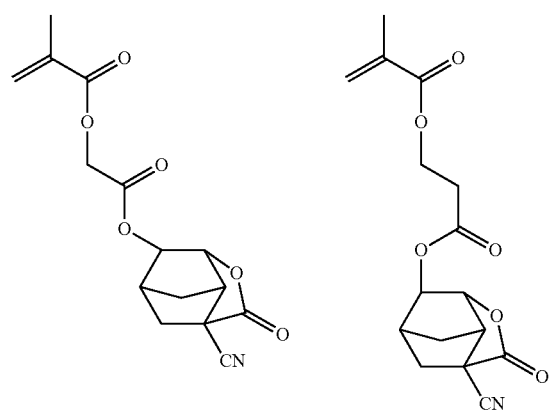
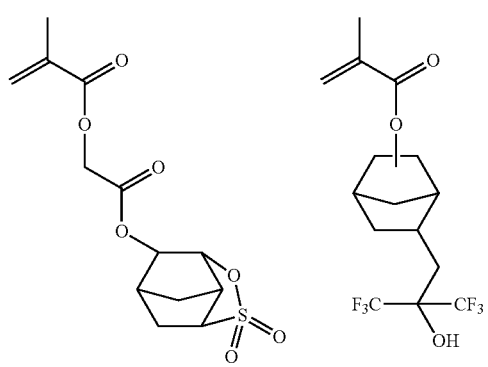
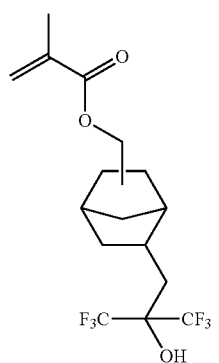
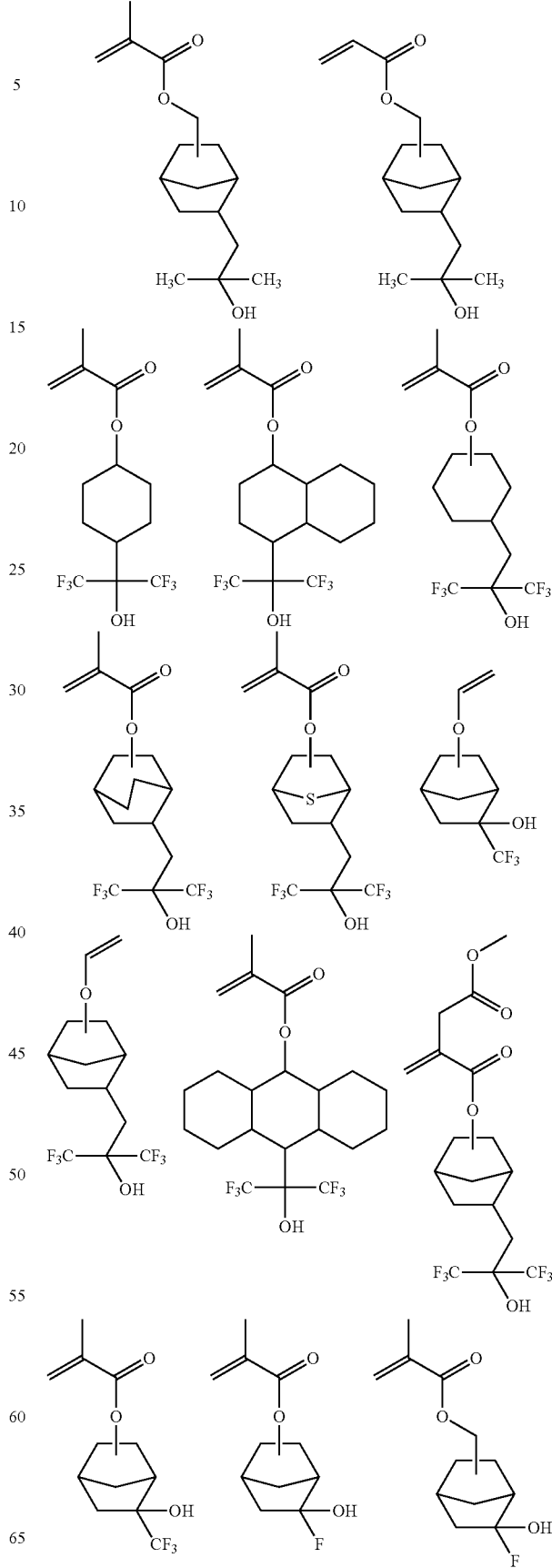

125
-continued
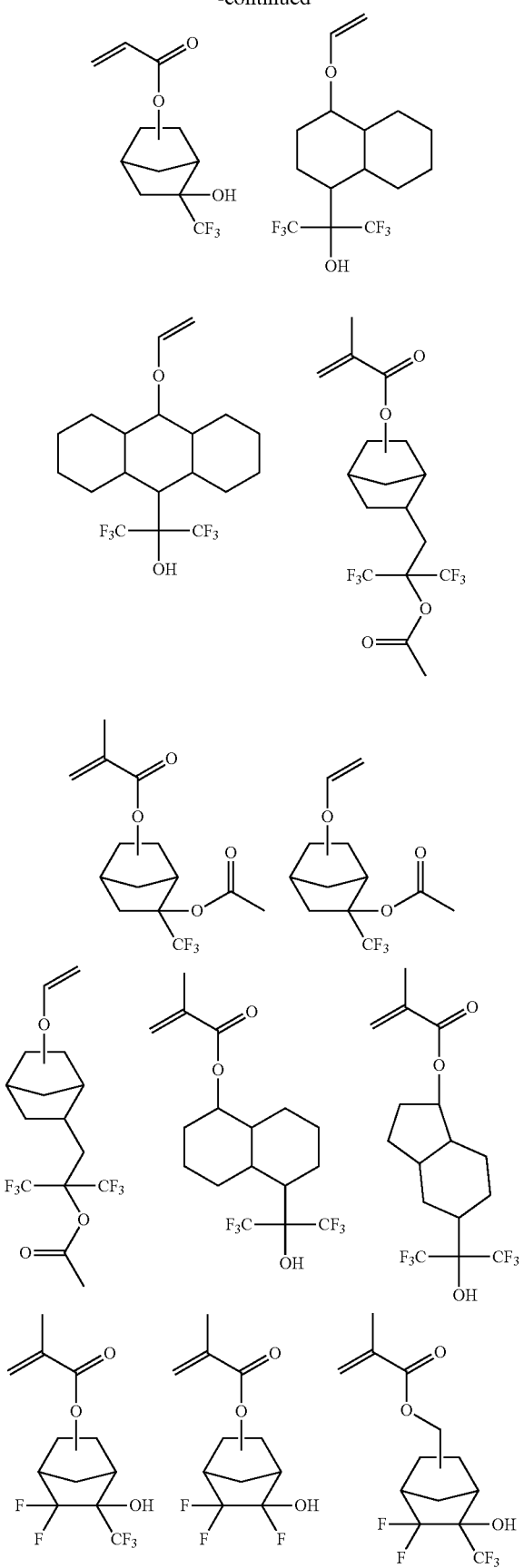
126
-continued
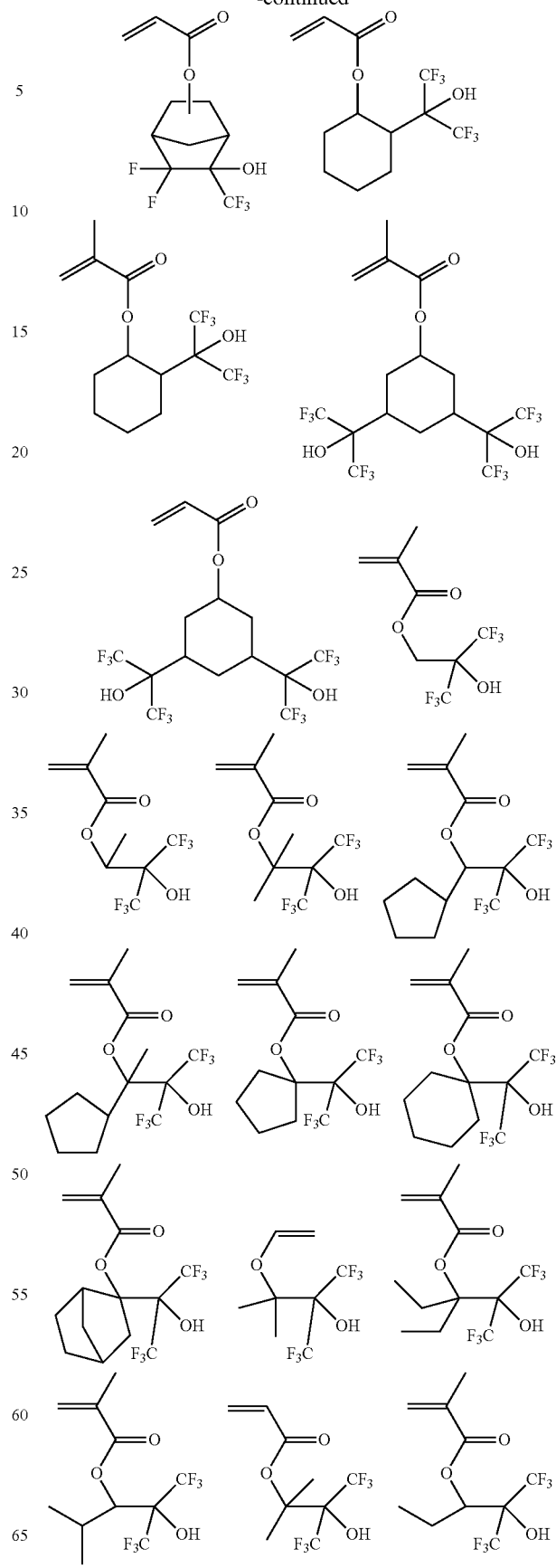

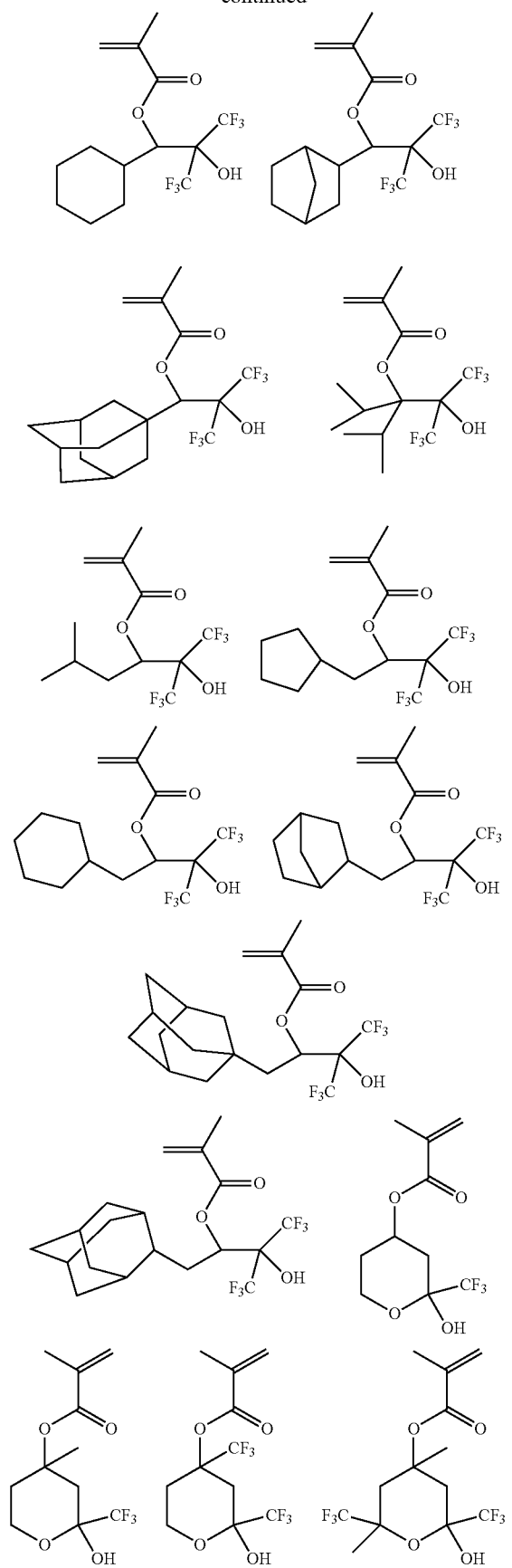
-continued

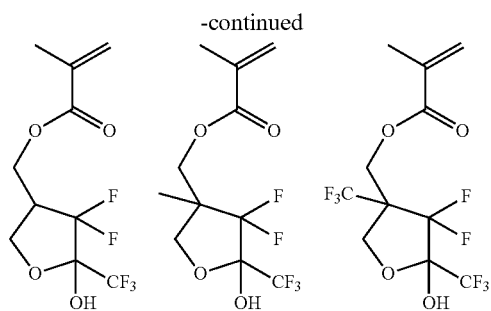
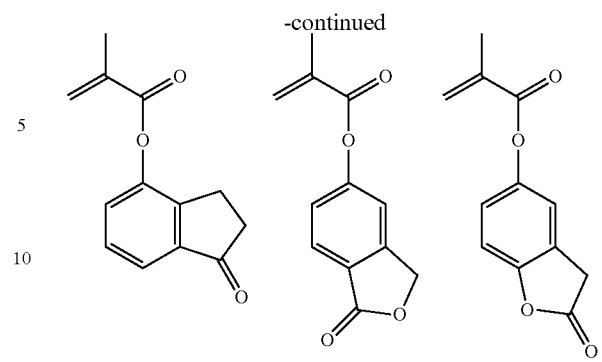
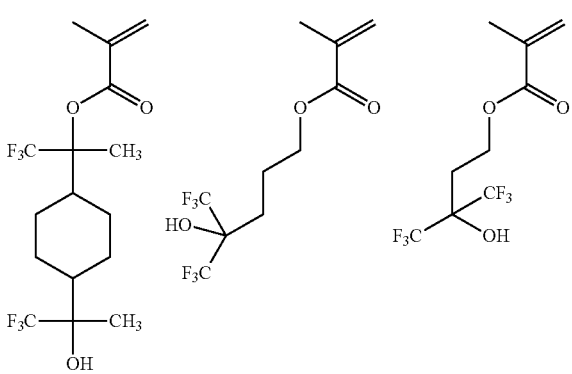
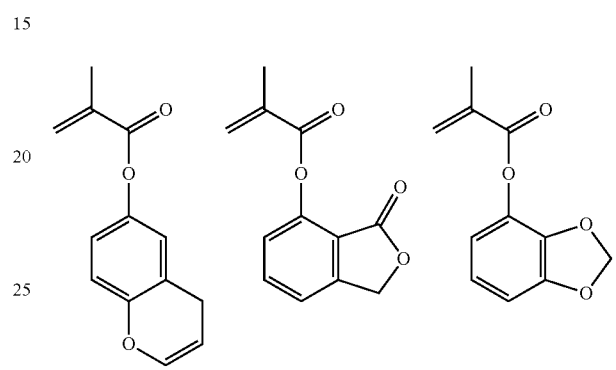
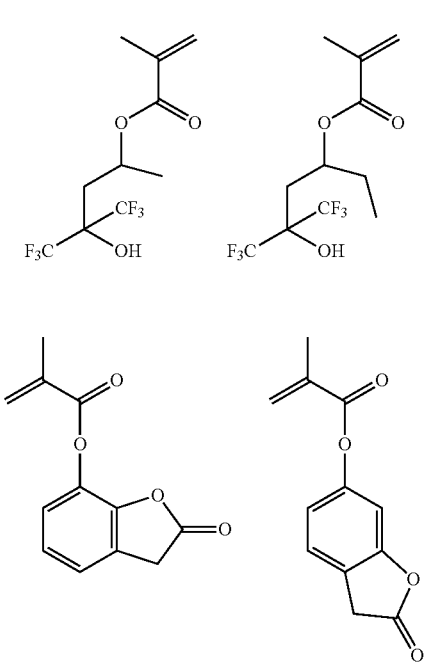
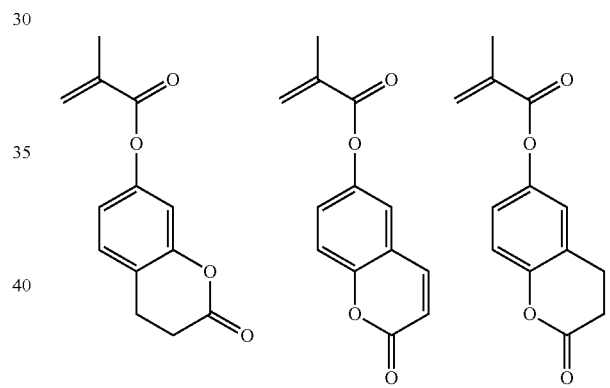
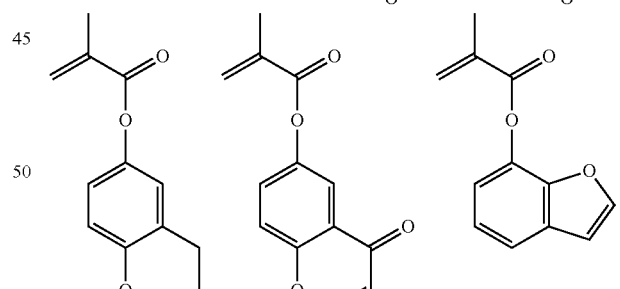
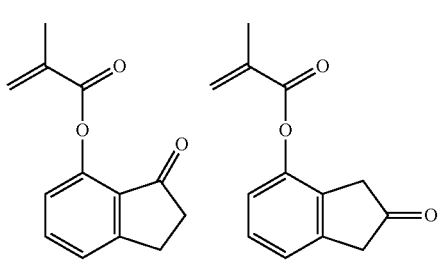
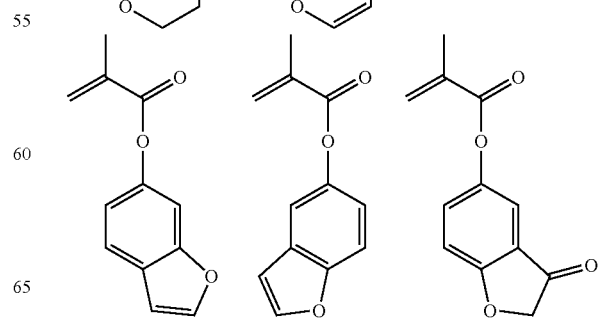

131
-continued
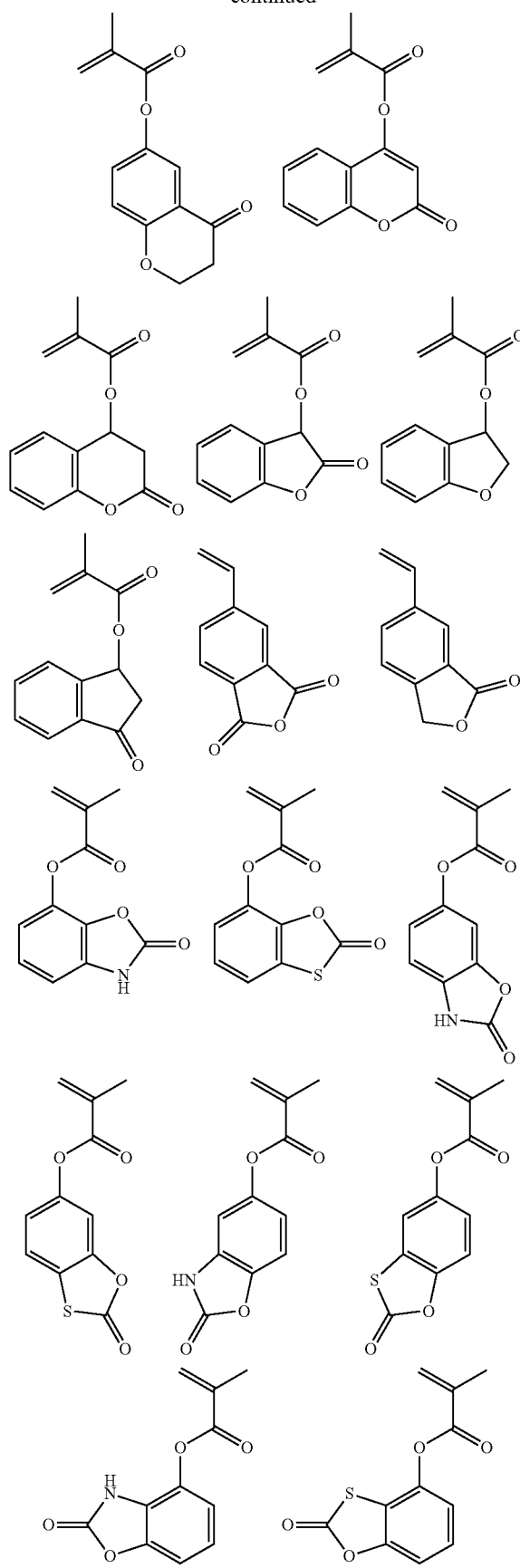
132
-continued
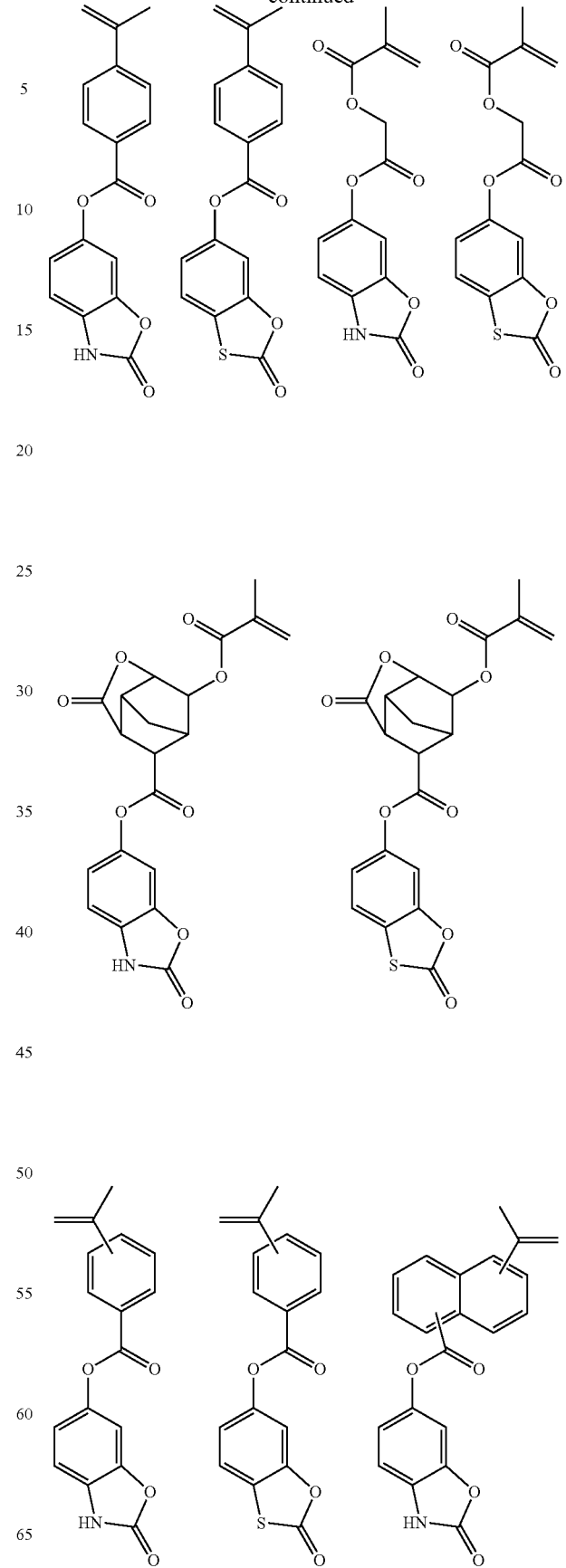

-continued

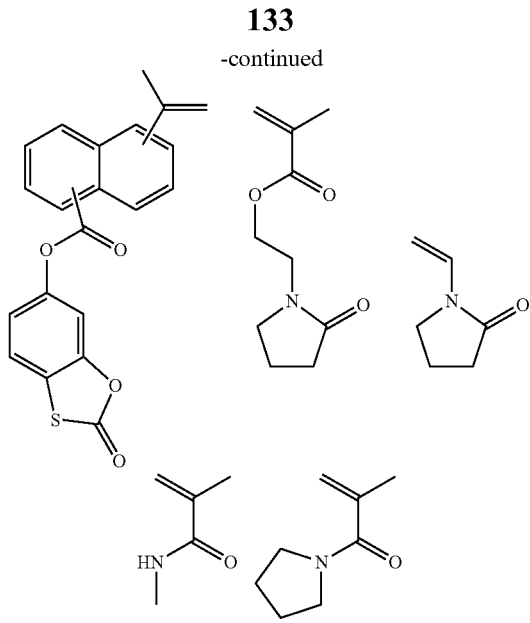

In the case of a hydroxyl-containing monomer, a corresponding monomer in which the hydroxyl group has been replaced by an acetal group which is susceptible to deprotection with acid, typically ethoxyethoxy, may be used, and polymerization be followed by deprotection with weak acid and water. Alternatively, the hydroxyl group may have been replaced by an acetyl, formyl or pivaloyl group, and polymerization be followed by alkaline hydrolysis.

The base resin may further comprise recurring units (e) derived from indene, benzofuran, benzothiophene, acenaphthylene, chromone, coumarin, norbornadiene, and derivatives thereof. Examples of the monomer from which recurring units (e) are derived are shown below, but not limited thereto.

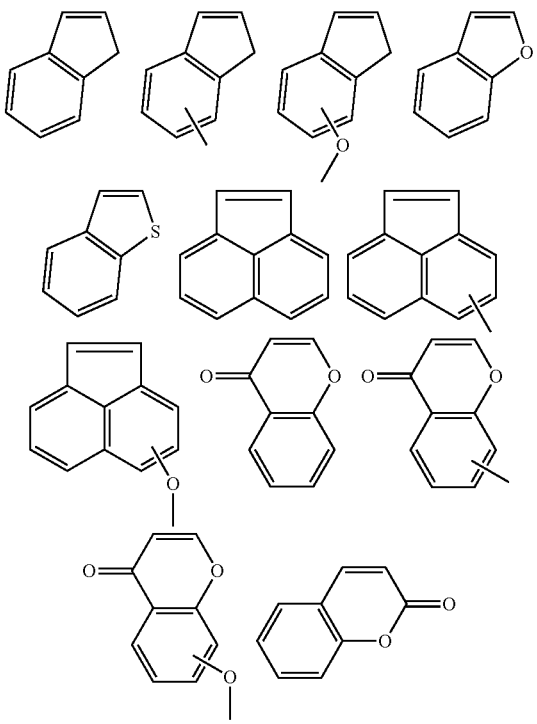

-continued

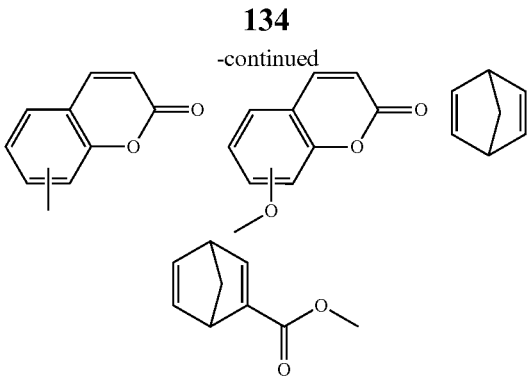

The base resin may further comprise recurring units (f) derived from styrene, vinylnaphthalene, vinylanthracene, vinylpyrene, methyleneindane, and derivatives thereof.

In a base resin having recurring units (a1), (a2), (b1), (b2), (b3), (c), (d), (e) and (f) copolymerized therein, the fraction of each unit may preferably fall in the range:
$0 \leq a1 \leq 1.0$, $0 \leq a2 \leq 1.0$, $0 < a1+a2 \leq 1.0$, $0 \leq b1 \leq 0.5$, $0 \leq b2 \leq 0.5$, $0 \leq b3 \leq 0.5$, $0 \leq b1+b2+b3 \leq 0.5$, $0 \leq c \leq 0.9$, $0 \leq d \leq 0.9$, $0 \leq e \leq 0.9$, and $0 \leq f \leq 0.5$;
more preferably $0 \leq a1 \leq 0.8$, $0 \leq a2 \leq 0.8$, $0.1 \leq a1+a2 \leq 0.8$, $0 \leq b1 \leq 0.4$, $0 \leq b2 \leq 0.4$, $0 \leq b3 \leq 0.4$, $0 \leq b1+b2+b3 \leq 0.4$, $0 \leq c \leq 0.8$, $0 \leq d \leq 0.8$, $0 \leq e \leq 0.8$, and $0 \leq f \leq 0.4$;
even more preferably $0 \leq a1 \leq 0.7$, $0 \leq a2 \leq 0.7$, $0.15 \leq a1+a2 \leq 0.7$, $0 \leq b1 \leq 0.3$, $0 \leq b2 \leq 0.3$, $0 \leq b3 \leq 0.3$, $0 \leq b1+b2+b3 \leq 0.3$, $0 \leq c \leq 0.7$, $0 \leq d \leq 0.7$, $0 \leq e \leq 0.7$, and $0 \leq f \leq 0.3$; and
most preferably $0 \leq a1 \leq 0.7$, $0 \leq a2 \leq 0.7$, $0.15 \leq a1+a2 \leq 0.7$, $0 \leq b1 \leq 0.3$, $0 \leq b2 \leq 0.3$, $0 \leq b3 \leq 0.3$, $0.1 \leq b1+b2+b3 \leq 0.3$, $0 < c \leq 0.7$, $0 \leq d \leq 0.7$, $0 \leq e \leq 0.7$, and $0 \leq f \leq 0.3$;
provided $a1+a2+b1+b2+b3+c+d+e+f=1$.

The base resin may be synthesized by any desired method, for example, by dissolving monomers corresponding to the respective units (a1), (a2), (b1), (b2), (b3), (c), (d), (e), and (f) in an organic solvent, adding a radical polymerization initiator thereto, and effecting heat polymerization. Examples of the organic solvent which can be used for polymerization include toluene, benzene, tetrahydrofuran, diethyl ether and dioxane. Examples of the polymerization initiator used herein include 2,2'-azobisisobutyronitrile (AIBN), 2,2'-azobis(2,4-dimethylvaleronitrile), dimethyl 2,2-azobis(2-methylpropionate), benzoyl peroxide, and lauroyl peroxide. Preferably the system is heated at 50 to 80° C. for polymerization to take place. The reaction time is 2 to 100 hours, preferably 5 to 20 hours.

When hydroxystyrene or hydroxyvinylnaphthalene is to be copolymerized, one possible procedure is by carrying out polymerization using acetoxystyrene or acetoxyvinylnaphthalene instead of hydroxystyrene or hydroxyvinylnaphthalene, and effecting alkaline hydrolysis for deprotection of the acetoxy group for converting back to hydroxystyrene or hydroxyvinylnaphthalene units. Suitable bases used for alkaline hydrolysis include ammonia water and triethylamine. The reaction conditions include a temperature of −20° C. to 100° C., preferably 0° C. to 60° C. and a time of 0.2 to 100 hours, preferably 0.5 to 20 hours.

The base resin should preferably have a weight average molecular weight (Mw) in the range of 1,000 to 500,000, and more preferably 2,000 to 30,000, as measured in tetrahydrofuran solvent by GPC versus polystyrene standards. With a Mw of at least 1,000, the resist composition is fully heat resistant. A polymer with a Mw of up to 500,000 may be devoid of a loss of alkaline solubility or a footing phenomenon after pattern formation.

If a multi-component copolymer has a broad molecular weight distribution or dispersity (Mw/Mn), which indicates the presence of lower and higher molecular weight polymer fractions, there is a possibility that following exposure, foreign matter is left on the pattern or the pattern profile is exacerbated. The influences of molecular weight and dispersity become stronger as the pattern rule becomes finer. Therefore, the base resin should preferably have a narrow dispersity (Mw/Mn) of 1.0 to 2.0, especially 1.0 to 1.5, in order to provide a resist composition suitable for micropatterning to a small feature size.

It is acceptable to use as the base resin a blend of two or more such polymers which differ in compositional ratio, Mw or Mw/Mn or a blend of an inventive polymer and another polymer.

The base resin defined above is especially suited as a base resin in a positive resist composition. When a positive resist composition is prepared by using the relevant base resin and combining it with suitable other components such as organic solvent, dissolution inhibitor, acid generator, basic compound, and surfactant, the resist composition has a very high sensitivity in that the polymer in the exposed region accelerates its dissolution rate in developer through catalytic reaction. The resist composition has many advantages including a high dissolution contrast, a high resolution, exposure latitude, process adaptability, a good pattern profile after exposure, high etch resistance, and minimized proximity bias due to controlled acid diffusion. Because of these advantages, the resist composition is fully viable in commercial processes and best suited as the micropatterning resist material for the fabrication of VLSIs.

Specifically, when an acid generator is added to formulate a chemically amplified positive resist composition capable of utilizing acid catalyzed reaction, a higher sensitivity is given and the aforementioned properties are further improved. When a dissolution inhibitor is added to the positive resist composition, the difference in dissolution rate between the exposed and unexposed regions is enhanced, with the resolution being further improved. When a basic compound is added, the rate of acid diffusion in the resist film can be suppressed, with the resolution being further improved. When a surfactant is added, the resist composition is further improved or controlled in coating operation.

In one embodiment, an acid generator is added to the resist composition in order that the composition function as a chemically amplified positive resist composition. Typical of the acid generator used herein is a photoacid generator (PAG) capable of generating an acid in response to actinic radiation or high-energy radiation. Suitable PAGs include sulfonium salts, iodonium salts, sulfonyldiazomethane, N-sulfonyloxyimide, and oxime-O-sulfonate acid generators. Exemplary acid generators are described in U.S. Pat. No. 7,537,880 (JP-A 2008-111103, paragraphs [0122]-[0142]), JP-A 2009-080474, and JP-A 2015-026064. The PAGs may be used alone or in admixture. When used, the acid generator is preferably added in an amount of 0.1 to 50 parts by weight per 100 parts by weight of the base resin.

Examples of the organic solvent used herein are described in JP-A 2008-111103, paragraphs [0144]-[0145]. Illustrative, non-limiting, examples of the organic solvent include ketones such as cyclohexanone and methyl n-pentyl ketone; alcohols such as 3-methoxybutanol, 3-methyl-3-methoxybutanol, 1-methoxy-2-propanol, and 1-ethoxy-2-propanol; ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; esters such as propylene glycol monomethyl ether acetate (PGMEA), propylene glycol monoethyl ether acetate, ethyl lactate, ethyl pyruvate, butyl acetate, methyl 3-methoxypropionate, ethyl 3-ethoxypropionate, t-butyl acetate, t-butyl propionate, and propylene glycol mono-t-butyl ether acetate; and lactones such as γ-butyrolactone. These solvents may be used alone or in combinations of two or more. An appropriate amount of the organic solvent used is 100 to 10,000 parts, especially 200 to 8,000 parts by weight per 100 parts by weight of the base resin.

Exemplary basic compounds or quenchers used herein are described in JP-A 2008-111103, paragraphs [0146]-[0164], and exemplary surfactants in paragraphs [0165]-[0166]. Examples of the dissolution inhibitor are described in JP-A 2008-122932, paragraphs [0155]-[0178] (U.S. Pat. No. 7,771,914). Also polymeric quenchers as described in JP-A 2008-239918 may be added. If necessary, acetylene alcohols may be added, for example, those described in JP-A 2008-122932, paragraphs [0179]-[0182].

Since the polymeric quencher segregates at the surface of a resist film as coated, it is effective for rendering the resist pattern more rectangular. The polymeric quencher is also effective for reducing a film thickness loss and preventing the pattern from being rounded at the top when a protective topcoat for the immersion lithography is applied.

Also a metal salt may be added as the quencher while exemplary metal salts are described in JP-A 2013-025211 (U.S. Pat. No. 9,360,753).

When used, the quencher is preferably added in an amount of 0.01 to 20 parts, more preferably 0.02 to 15 parts by weight per 100 parts by weight of the base resin. When used, the surfactant is preferably added in an amount of 0.0001 to 10 parts, more preferably 0.001 to 5 parts by weight per 100 parts by weight of the base resin. When used, the dissolution inhibitor is preferably added in an amount of 0.5 to 50 parts, more preferably 1 to 30 parts by weight per 100 parts by weight of the base resin. When used, the polymeric quencher may be added in any desired amount as long as the benefits of the invention are not impaired. When used, the acetylene alcohol is preferably added in an amount of 0 to 2%, more preferably 0.02 to 1% by weight based on the resist composition.

Process

Another embodiment of the invention is a pattern forming process comprising the steps of coating the resist composition defined above onto a substrate, baking the coating to form a resist film, exposing the resist film to high-energy radiation, and developing the exposed resist film with a developer. The step of exposing the resist film to high-energy radiation may use EUV of wavelength 3 to 15 nm or EB, specifically EB at an accelerating voltage of 1 to 150 kV.

Since the salt having formula (1) is an electrically conductive metal salt, it is effective for preventing any charge buildup in the resist film during EB image writing. It is then not necessarily essential to form an antistatic film on the resist film. Since the salt having formula (1) is strongly absorptive to EUV of wavelength 13.5 nm, the sensitivity of the resist film is improved upon exposure to EUV by the mechanism that the outer shell electrons of the metal are excited, and the electrons transfer to the acid generator, whereby the efficiency of acid generation is enhanced.

Since the salt having formula (1) does not undergo salt exchange with fluorosulfonic acid or fluorosulfonimidic acid generated from the acid generator, it does not function as a quencher. This allows the salt having formula (1) to be added in a more amount than quenchers. Thus the advantages of increased absorption of EUV and increased sensitivity are available.

When the resist composition is used for the microfabrication of various integrated circuits, any well-known lithography processes may be applied.

Upon imagewise exposure to EB or EUV, the sodium, magnesium, potassium, calcium, rubidium, strontium, yttrium, cesium, barium or cerium salt generates secondary electrons, to which the acid generator is sensitive. This leads to a high sensitivity. However, if secondary electrons randomly diffuse in the resist film, the image is blurred. With this combined with diffusion of the acid generated by the acid generator, the image blur is exaggerated, inviting an increase of edge roughness. If secondary electrons diffuse in the thickness direction of the resist film, i.e., perpendicular to the substrate, then the image blur is suppressed. When the substrate is electrically charged positive (+), secondary electrons move as if they were sucked into the substrate, that is, secondary electrons diffuse perpendicularly. Then the sensitivity can be improved while suppressing the image blur, and without degrading the edge roughness.

For example, the resist composition is applied onto a substrate for integrated circuit fabrication or a processable layer thereon (e.g., Si, $SiO_2$, SiN, SiON, TiN, WSi, BPSG, SOG, or organic antireflective coating) or a substrate for mask circuit fabrication or a processable layer thereon (e.g., Cr, CrO, CrON, or $MoSi_2$) by any suitable technique such as spin coating, roll coating, flow coating, dip coating, spray coating or doctor coating. The coating is prebaked on a hot plate at a temperature of 60 to 150° C. for 10 seconds to 30 minutes, preferably 80 to 120° C. for 30 seconds to 20 minutes to form a resist film having a thickness of 0.1 to 2.0 μm.

Next the resist film is exposed imagewise to high-energy radiation selected from among UV, DUV, EB, x-ray, soft x-ray, excimer laser, γ-ray, synchrotron radiation, or EUV directly or through a mask having the desired pattern. The exposure is preferably carried out to provide a dose of 1 to 200 mJ/cm², preferably 10 to 100 mJ/cm², or 0.1 to 100 μC/cm², preferably 0.5 to 50 μC/cm². This is followed by baking (PEB) on a hot plate at 60 to 150° C. for 10 seconds to 30 minutes, preferably at 80 to 120° C. for 30 seconds to 20 minutes.

Finally, the exposed resist film is developed with a developer which is an aqueous alkaline solution, typically a 0.1 to 5%, preferably 2 to 3% by weight of tetramethylammonium hydroxide (TMAH), choline hydroxide, tetraethylammonium hydroxide (TEAH), tetrapropylammonium hydroxide (TPAH), tetrabutylammonium hydroxide (TBAH), benzyltrimethylammonium hydroxide or benzyltriethylammonium hydroxide. Development is carried out for 3 seconds to 3 minutes, preferably 5 seconds to 2 minutes by any conventional techniques such as dip, puddle and spray techniques. The exposed region of resist film is dissolved in the developer, but not the unexposed region. In this way, the desired positive pattern is formed on the substrate.

Alternatively, a negative tone pattern may be formed by organic solvent development. The organic solvent used as the developer is preferably selected from 2-octanone, 2-nonanone, 2-heptanone, 3-heptanone, 4-heptanone, 2-hexanone, 3-hexanone, diisobutyl ketone, methylcyclohexanone, acetophenone, methylacetophenone, propyl acetate, butyl acetate, isobutyl acetate, pentyl acetate, isopentyl acetate, butenyl acetate, propyl formate, butyl formate, isobutyl formate, pentyl formate, isopentyl formate, methyl valerate, methyl pentenoate, methyl crotonate, ethyl crotonate, methyl propionate, ethyl propionate, ethyl 3-ethoxypropionate, methyl lactate, ethyl lactate, propyl lactate, butyl lactate, isobutyl lactate, pentyl lactate, isopentyl lactate, methyl 2-hydroxyisobutyrate, ethyl 2-hydroxyisobutyrate, methyl benzoate, ethyl benzoate, phenyl acetate, benzyl acetate, methyl phenylacetate, benzyl formate, phenylethyl formate, methyl 3-phenylpropionate, benzyl propionate, ethyl phenylacetate, and 2-phenylethyl acetate. These organic solvents may be used alone or in admixture of two or more.

At the end of development, the resist film is rinsed. As the rinsing liquid, a solvent which is miscible with the developer and does not dissolve the resist film is preferred. Suitable solvents include alcohols of 3 to 10 carbon atoms, ether compounds of 8 to 12 carbon atoms, alkanes, alkenes, and alkynes of 6 to 12 carbon atoms, and aromatic solvents. Specifically, suitable alcohols of 3 to 10 carbon atoms include n-propyl alcohol, isopropyl alcohol, 1-butyl alcohol, 2-butyl alcohol, isobutyl alcohol, t-butyl alcohol, 1-pentanol, 2-pentanol, 3-pentanol, t-pentyl alcohol, neopentyl alcohol, 2-methyl-1-butanol, 3-methyl-1-butanol, 3-methyl-3-pentanol, cyclopentanol, 1-hexanol, 2-hexanol, 3-hexanol, 2,3-dimethyl-2-butanol, 3,3-dimethyl-1-butanol, 3,3-dimethyl-2-butanol, 2-ethyl-1-butanol, 2-methyl-1-pentanol, 2-methyl-2-pentanol, 2-methyl-3-pentanol, 3-methyl-1-pentanol, 3-methyl-2-pentanol, 3-methyl-3-pentanol, 4-methyl-1-pentanol, 4-methyl-2-pentanol, 4-methyl-3-pentanol, cyclohexanol, and 1-octanol. Suitable ether compounds of 8 to 12 carbon atoms include di-n-butyl ether, diisobutyl ether, di-s-butyl ether, di-n-pentyl ether, diisopentyl ether, di-s-pentyl ether, di-t-pentyl ether, and di-n-hexyl ether. Suitable alkanes of 6 to 12 carbon atoms include hexane, heptane, octane, nonane, decane, undecane, dodecane, methylcyclopentane, dimethylcyclopentane, cyclohexane, methylcyclohexane, dimethylcyclohexane, cycloheptane, cyclooctane, and cyclononane. Suitable alkenes of 6 to 12 carbon atoms include hexene, heptene, octene, cyclohexene, methylcyclohexene, dimethylcyclohexene, cycloheptene, and cyclooctene. Suitable alkynes of 6 to 12 carbon atoms include hexyne, heptyne, and octyne. Besides the foregoing solvents, aromatic solvents may be used, for example, toluene, xylene, ethylbenzene, isopropylbenzene, t-butylbenzene and mesitylene. The solvents may be used alone or in admixture.

Of the variety of high-energy radiation, the resist composition is best suited in micropatterning with EB, EUV, x-ray, soft x-ray, γ-ray, or synchrotron radiation. Particularly when EUV of wavelength 3 to 15 nm or an accelerated EB at an accelerating voltage of 1 to 150 kV, preferably up to 100 kV, especially a low voltage accelerated EB at an accelerating voltage of up to 50 kV is used, a finer size pattern can be formed.

EXAMPLE

Examples are given below by way of illustration of the invention and not by way of limitation. The abbreviation "pbw" is parts by weight. For all polymers, Mw and Mn are determined versus polystyrene standards by GPC using tetrahydrofuran (THF) solvent.

Synthesis Example

Synthesis Example 1

Synthesis of barium 2-(adamantane-1-carbonyloxy)-1,1,3,3,3-pentafluoropropane-1-sulfonate (Barium Salt 1)

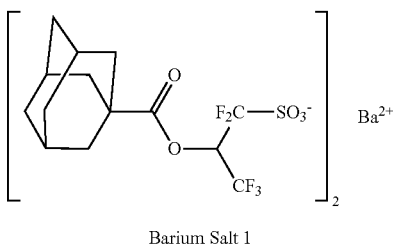

Barium Salt 1

1) Synthesis of benzyltrimethylammonium 2-hydroxy-1,1,3,3,3-pentafluoropropane-1-sulfonate (Intermediate 1)

An aqueous solution of sodium 2-hydroxy-1,1,3,3,3-pentafluoropropane-1-sulfonate was synthesized according to the method described in U.S. Pat. No. 8,283,104 (JP-A 2010-215608). Then 1,200 g of this aqueous solution (corresponding to 1 mole of sodium 2-hydroxy-1,1,3,3,3-pentafluoropropane-1-sulfonate) was combined with 223 g of benzyltrimethylammonium chloride and 2,000 g of methylene chloride and agitated for 10 minutes. The organic layer was taken out. The thus extracted organic layer was washed with water and concentrated in vacuum. To the concentrated residue, diisopropyl ether was added for recrystallization. The crystallized solid was collected and dried in vacuum, obtaining 354 g of the desired compound, benzyltrimethylammonium 2-hydroxy-1,1,3,3,3-pentafluoropropane-1-sulfonate (Intermediate 1) in white solid form (yield 86%).

2) Synthesis of benzyltrimethylammonium 2-(adamantane-1-carbonyloxy)-1,1,3,3,3-pentafluoropropane-1-sulfonate (Intermediate 2)

In toluene, 1-adamantanecarboxylic acid was reacted with oxalyl chloride to form a corresponding carboxylic acid chloride. Then methylene chloride was added to form a 25 wt % solution. A mixture of 123 g of Intermediate 1, 45 g of triethylamine, 9 g of 4-dimethylaminopyridine, and 600 g of methylene chloride was prepared. Under ice cooling, the methylene chloride solution of the carboxylic acid chloride was added dropwise to this mixture. After the dropwise addition, the solution was aged at room temperature for 10 hours, and dilute hydrochloric acid was added to quench the reaction. Then the organic layer was collected, washed with water, and concentrated in vacuum. To the concentrated residue, 1,500 g of diisopropyl ether was added for recrystallization. The crystal was collected by filtration and dried in vacuum, obtaining 158 g of the desired compound, benzyltrimethylammonium 2-(adamantane-1-carbonyloxy)-1,1,3,3,3-pentafluoropropane-1-sulfonate (Intermediate 2) as white crystal (yield 90%).

3) Synthesis of barium 2-(adamantane-1-carbonyloxy)-1,1,3,3,3-pentafluoropropane-1-sulfonate (Barium Salt 1)

A mixture of 16 g of Intermediate 2, 50 g of ion exchange resin Duolite® C255LFH (Sumika Chemtex Co., Ltd.), and 80 g of methanol was agitated for 2 hours, after which the ion exchange resin was filtered off. The filtrate was combined with a mixture of 3 g of barium hydroxide octahydrate and 100 g of water, and concentrated in vacuum. The concentrated residue was washed with diisopropyl ether, obtaining 7 g of the target compound, barium 2-(adamantane-1-carbonyloxy)-1,1,3,3,3-pentafluoropropane-1-sulfonate (Barium Salt 1) (yield 80%).

Figure 2:
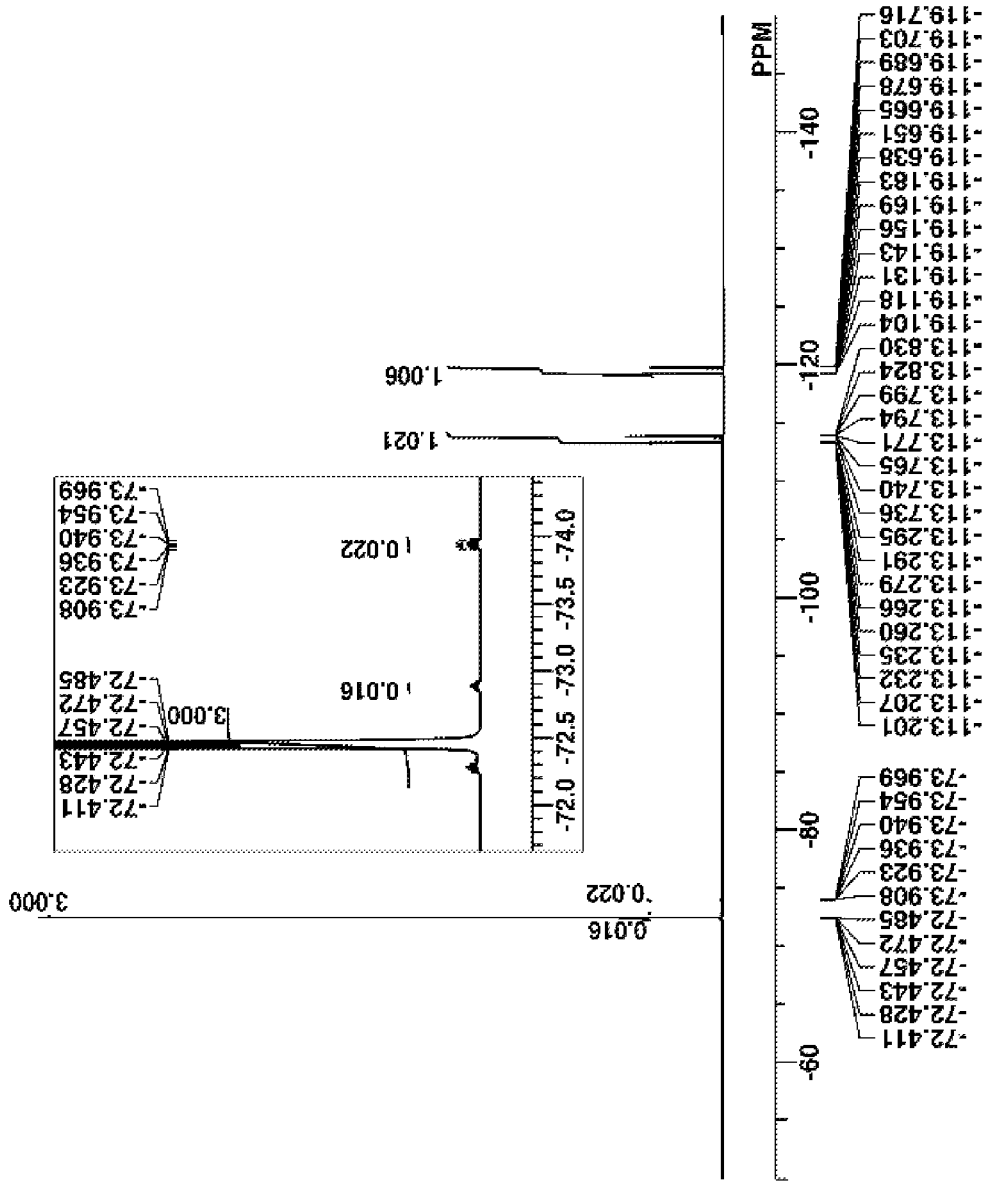
FIG. 2 is a diagram showing $^{19}$F-NMR spectrum of Barium Salt 1 in Synthesis Example 1.

The target compound was analyzed by infrared (IR) absorption spectroscopy and nuclear magnetic resonance (NMR) spectroscopy. The results of $^1$H-NMR and $^{19}$F-NMR in DMSO-$d_6$ are shown in FIGS. 1 and 2, respectively. It is noted that in $^1$H-NMR spectroscopy, traces of diisopropyl ether and water in DMSO-$d_6$ were observed.

IR (D-ATR): 2910, 2852, 1725, 1712, 1452, 1375, 1338, 1276, 1235, 1192, 1165, 1103, 1088, 994, 924, 870, 840, 646, 621, 572 cm$^{-1}$

Synthesis Example 2

Synthesis of cesium 2-(adamantane-1-carbonyloxy)-1,1,3,3,3-pentafluoropropane-1-sulfonate (Cesium Salt 1)

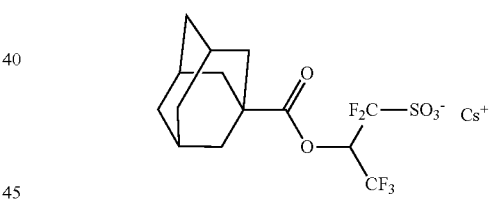

Cedium Salt 1

Intermediate 2, 12 g, was dissolved in 60 g of methanol, which was combined with 37 g of ion exchange resin Duolite® C255LFH (Sumika Chemtex Co., Ltd.), and agitated for 1 hour. Thereafter, the ion exchange resin was filtered off. The filtrate was concentrated in vacuum by removing methanol. To the concentrate were added 4.9 g of cesium carbonate and 80 g of deionized water. The solution was stirred at room temperature for 5 minutes, after which it was concentrated in vacuum by removing the solvent. Diisopropyl ether was added to the concentrated residue, allowing crystals to precipitate. The crystals were collected by filtration and dried by heating in vacuum, obtaining 10 g of the target compound, cesium 2-(adamantane-1-carbonyloxy)-1,1,3,3,3-pentafluoropropane-1-sulfonate (yield 86%).

Synthesis Example 3

Synthesis of cerium 2-(adamantane-1-carbonyloxy)-1,1,3,3,3-pentafluoropropane-1-sulfonate (Cerium Salt 1)

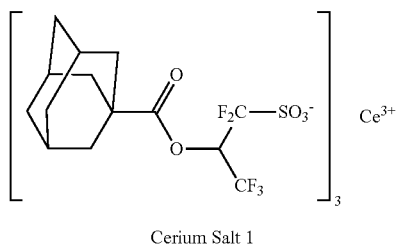

Cerium Salt 1

Intermediate 2, 8.1 g, was dissolved in 40 g of methanol, which was combined with 24 g of ion exchange resin Duolite® C255LFH (Sumika Chemtex Co., Ltd.), and agitated for 1 hour. Thereafter, the ion exchange resin was filtered off. The filtrate was concentrated in vacuum by removing methanol. To the concentrate was added 1.8 g of cerium(III) carbonate octahydrate. The mixture was stirred at room temperature overnight. It was filtered through a Celite® filter to remove the insoluble. Methyl isobutyl ketone was added to the filtrate, which was concentrated in vacuum. The concentrated residue was washed with diisopropyl ether. The residue was dried by heating in vacuum, obtaining 6.1 g of the target compound, cerium 2-(adamantane-1-carbonyloxy)-1,1,3,3,3-pentafluoropropane-1-sulfonate (yield 90%).

Synthesis Examples 4 to 22

Synthesis of Sodium Salt 1, Magnesium Salt 1, Potassium Salt 1, Calcium Salt 1, Barium Salts 2 to 11, Cesium Salts 2 to 4, Rubidium Salt 1, and Strontium Salt 1

Sodium Salt 1, Magnesium Salt 1, Potassium Salt 1, Calcium Salt 1, Barium Salts 2 to 11, Cesium Salts 2 to 4, Rubidium Salt 1, and Strontium Salt 1 were synthesized by repeating the same procedure as in Synthesis Example 1 aside from changing the type of anion and the type of metal in metal hydroxide.

Sodium Salt 1, Magnesium Salt 1, Potassium Salt 1, Calcium Salt 1, Barium Salts 1 to 11, Cesium Salts 1 to 4, Rubidium Salt 1, Strontium Salt 1, and Cerium Salt 1 are identified below by their structure formula.

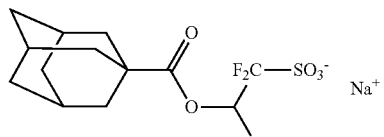

Sodium Salt 1

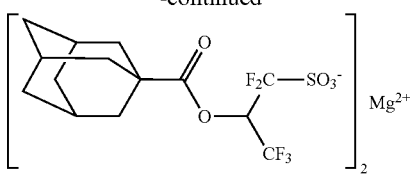

Magnesium Salt 1

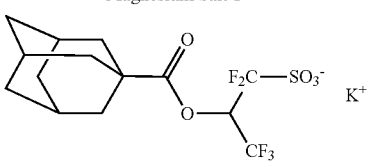

Potassium Salt 1

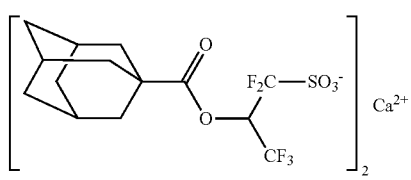

Calcium Salt 1

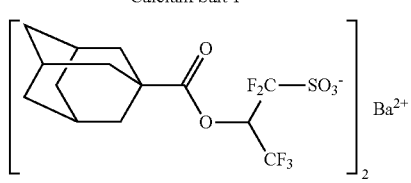

Barium Salt 1

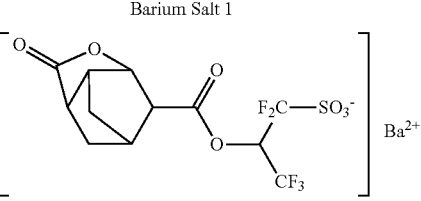

Barium Salt 2

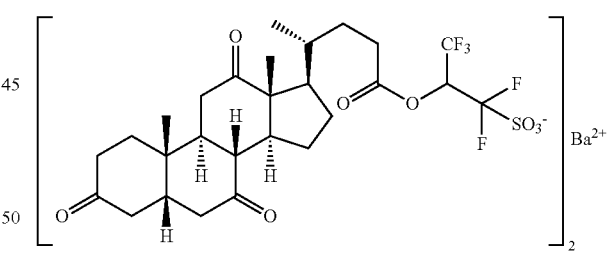

Barium Salt 3

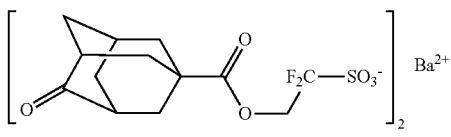

Barium Salt 4

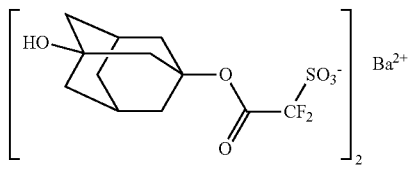

Barium Salt 5

-continued

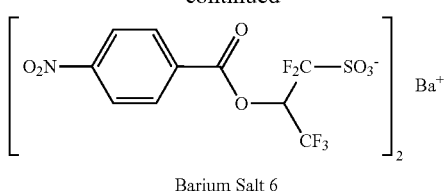

Barium Salt 6

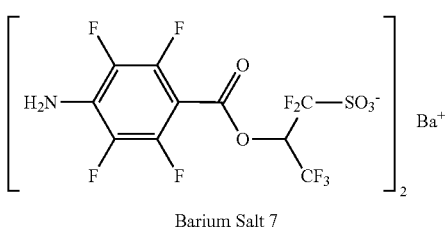

Barium Salt 7

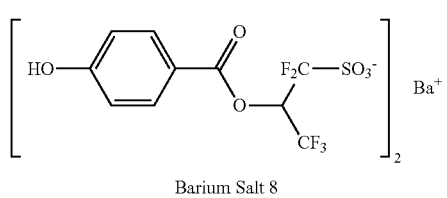

Barium Salt 8

Barium Salt 9

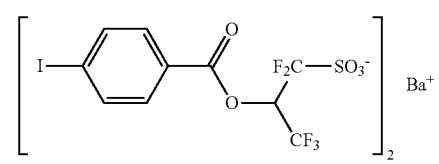

Barium Salt 10

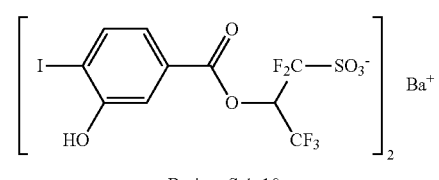

Barium Salt 11

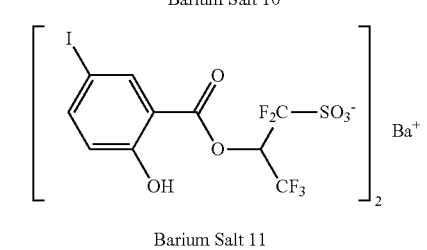

Cesium Salt 1

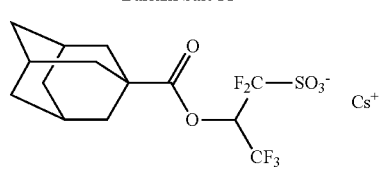

Cesium Salt 2

-continued

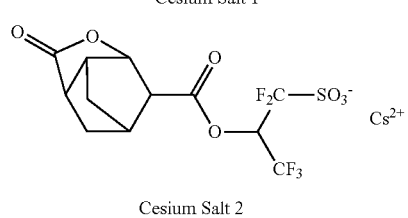

Cesium Salt 3

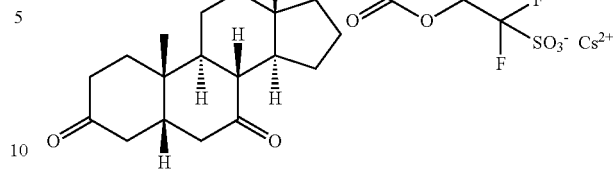

Cesium Salt 4

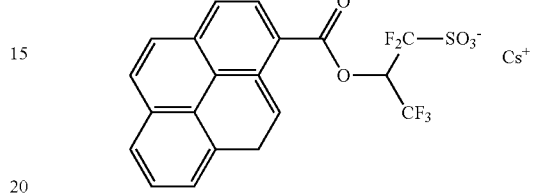

Rubidium Salt 3

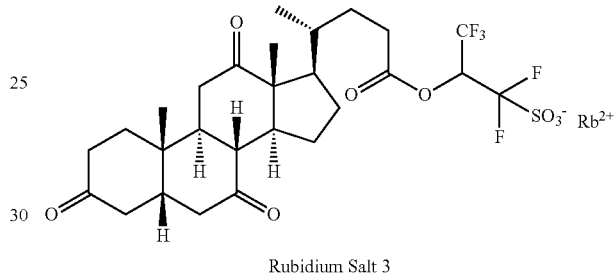

Strontium Salt 1

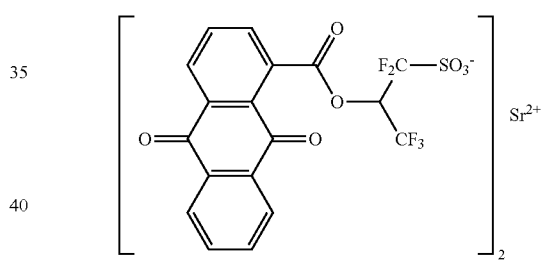

Cerium Salt 1

Synthesis Examples 23 to 27

Synthesis of Base Resins

Various base resins (Polymers 1 to 5) were prepared by combining suitable monomers, effecting copolymerization reaction in THF solvent, pouring into methanol for crystallization, repeatedly washing with hexane, isolation, and drying. The base resins were analyzed by $^1$H-NMR to determine their composition and by GPC to determine Mw and dispersity Mw/Mn.

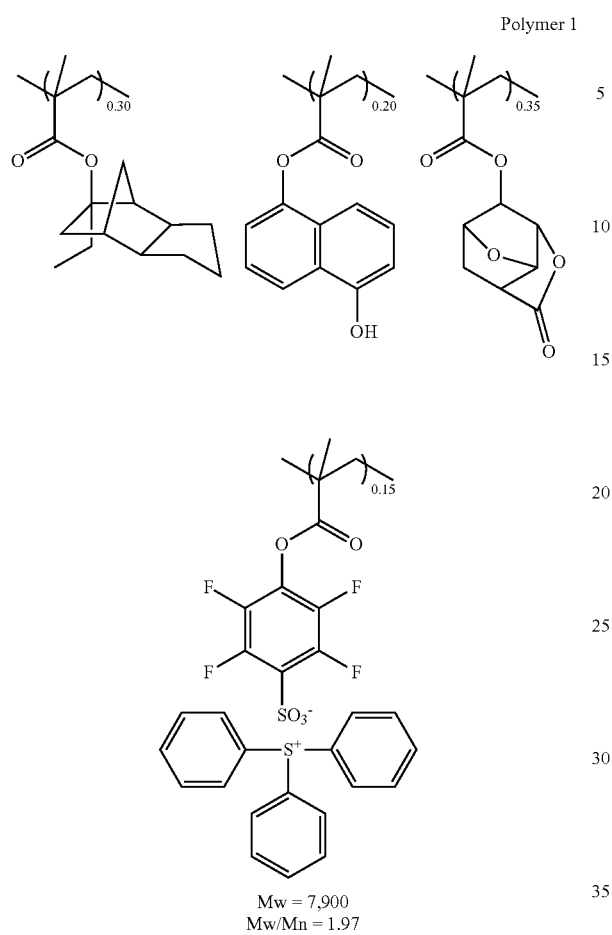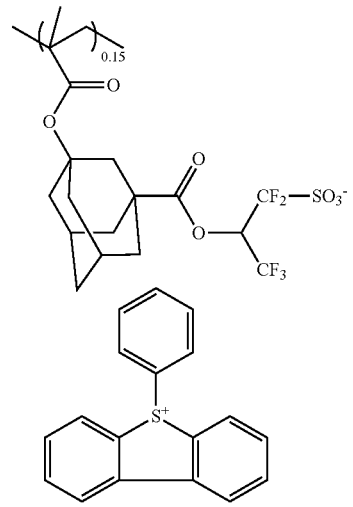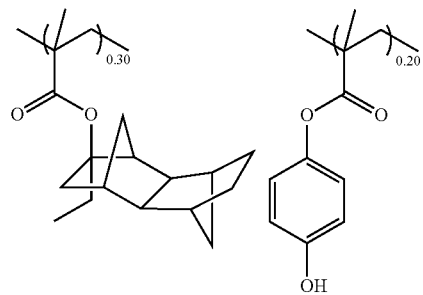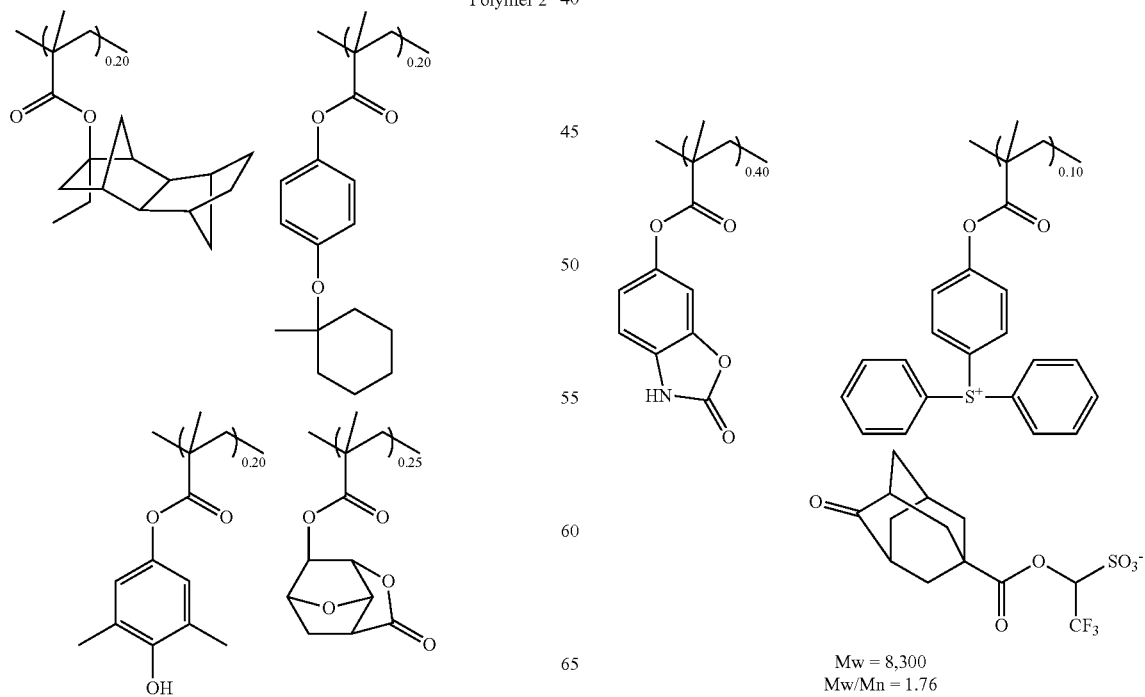

-continued

Polymer 4

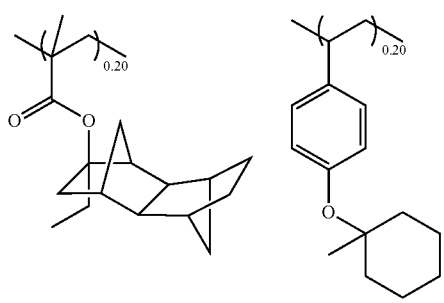

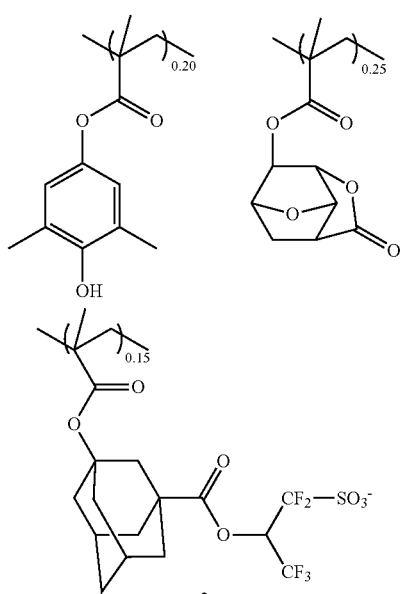

Mw = 9,000
Mw/Mn = 1.98

-continued

Polymer 5

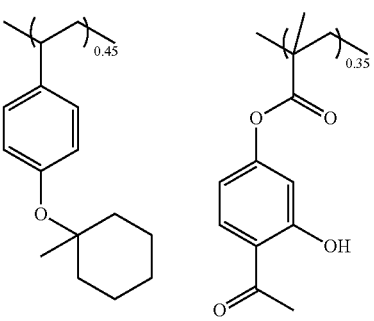

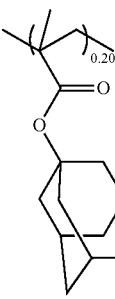

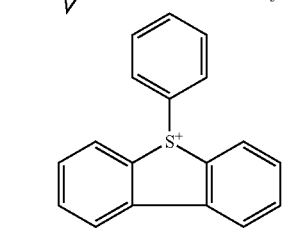

Mw = 8,400
Mw/Mn = 1.91

Examples 1 to 26 & Comparative Examples 1 to 3

Preparation of Resist Composition

Positive resist compositions in solution form were prepared by dissolving a base resin (synthesized above) and selected components in a solvent in accordance with the formulation of Tables 1 to 3 and filtering through a filter with a pore size of 0.2 μm. The solvent contained 100 ppm of surfactant FC-4430 (commercially available from 3M). The components in Tables 1 to 3 are identified below.

Acid Generator: PAG1 of the Following Structural Formula

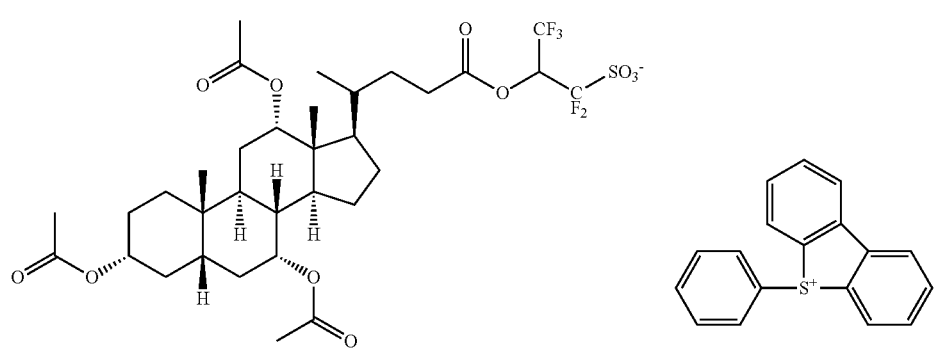

PAG 1

Quencher:
Amine 1, Amine 2, and cesium pivalate of the following structural formulae

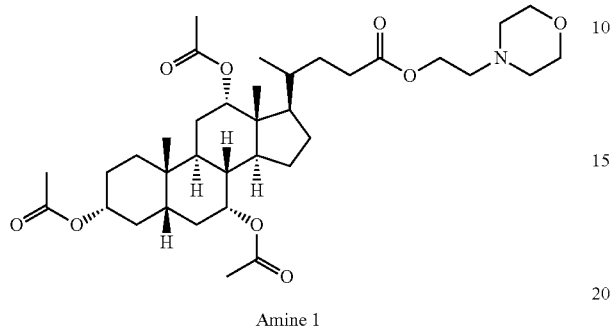

Amine 1

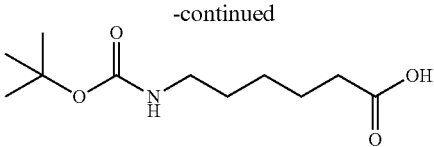

Amine 2

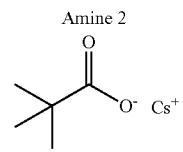

cesium pivalate

Organic Solvents:
  PGMEA (propylene glycol monomethyl ether acetate)
  PGME (propylene glycol monomethyl ether)
  CyH (cyclohexanone)
  GBL (γ-butyrolactone)

TABLE 1

|   |   | Resist | Polymer (pbw) | Metal compound (pbw) | Acid generator (pbw) | Quencher (pbw) | Organic solvent (pbw) |
|---|---|---|---|---|---|---|---|
| Example | 1 | Resist 1 | Polymer 1 (100) | Barium Salt 1 (6.0) | — | Amine 1 (1.3) | PGMEA (1,000) CyH (1,000) GBL (200) |
|  | 2 | Resist 2 | Polymer 2 (100) | Barium Salt 1 (6.0) | — | Amine 1 (1.3) | PGMEA (1,000) CyH (1,000) GBL (200) |
|  | 3 | Resist 3 | Polymer 3 (100) | Barium Salt 1 (6.0) | — | Amine 1 (1.3) | PGMEA (1,000) CyH (1,000) GBL (200) |
|  | 4 | Resist 4 | Polymer 4 (100) | Barium Salt 1 (6.0) | — | Amine 1 (1.3) | PGMEA (1,000) CyH (1,000) GBL (200) |
|  | 5 | Resist 5 | Polymer 5 (100) | Barium Salt 1 (6.0) | — | Amine 1 (1.3) | PGMEA (1,000) CyH (1000) GBL (200) |
|  | 6 | Resist 6 | Polymer 1 (100) | Barium Salt 2 (6.0) | — | Amine 2 (0.5) | PGMEA (1,000) CyH (1,000) GBL (200) |
|  | 7 | Resist 7 | Polymer 1 (100) | Barium Salt 3 (9.1) | — | Amine 1 (1.3) | PGMEA (1,000) CyH (1,000) GBL (200) |
|  | 8 | Resist 8 | Polymer 1 (100) | Barium Salt 4 (11.2) | — | Amine 1 (1.3) | PGMEA (1,000) CyH (1,000) GBL (200) |
|  | 9 | Resist 9 | Polymer 1 (100) | Barium Salt 5 (5.2) | — | Amine 1 (1.3) | PGMEA (1,000) CyH (1,000) GBL (200) |
|  | 10 | Resist 10 | Polymer 1 (100) | Barium Salt 6 (5.8) | — | Amine 1 (1.3) | PGMEA (1,000) CyH (1,000) GBL (200) |
|  | 11 | Resist 11 | Polymer 1 (100) | Barium Salt 7 (6.2) | — | Amine 1 (1.3) | PGMEA (1,000) CyH (1,000) GBL (200) |
|  | 12 | Resist 12 | Polymer 1 (100) | Barium Salt 8 (5.0) | — | Amine 1 (1.3) | PGMEA (1,000) CyH (1,000) GBL (200) |
|  | 13 | Resist 13 | Polymer 1 (100) | Cesium Salt 2 (3.9) | — | Amine 1 (1.3) | PGMEA (1,000) CyH (1,000) GBL (200) |

TABLE 2

| | Resist | Polymer (pbw) | Metal compound (pbw) | Acid generator (pbw) | Quencher (pbw) | Organic solvent (pbw) |
|---|---|---|---|---|---|---|
| Example 14 | Resist 14 | Polymer 1 (100) | Cesium Salt 3 (5.8) | — | Amine 1 (1.3) | PGMEA (1,000) CyH (1,000) GBL (200) |
| 15 | Resist 15 | Polymer 1 (100) | Cesium Salt 4 (4.2) | PAG1 (5.0) | Amine 1 (1.3) | PGMEA (1,000) CyH (1,000) GBL (200) |
| 16 | Resist 16 | Polymer 1 (100) | Rubidium Salt 1 (4.8) | — | Amine 1 (1.3) | PGMEA (1,000) CyH (1,000) GBL (200) |
| 17 | Resist 17 | Polymer 1 (100) | Strontium Salt 1 (6.6) | — | cesium pivalate (1.2) | PGMEA (1,000) CyH (1,000) PGME (300) |
| 18 | Resist 18 | Polymer 1 (100) | Barium Salt 9 (5.0) | — | cesium pivalate (1.2) | PGMEA (1,000) CyH (1000) PGME (300) |
| 19 | Resist 19 | Polymer 1 (100) | Barium Salt 10 (5.0) | — | cesium pivalate (1.2) | PGMEA (1,000) CyH (1,000) PGME (300) |
| 20 | Resist 20 | Polymer 1 (100) | Barium Salt 11 (5.0) | — | cesium pivalate (1.2) | PGMEA (1,000) CyH (1,000) PGME (300) |
| 21 | Resist 21 | Polymer 1 (100) | Cesium Salt 1 (5.0) | — | cesium pivalate (1.2) | PGMEA (1,000) CyH (1,000) PGME (300) |
| 22 | Resist 22 | Polymer 1 (100) | Cesium Salt 1 (2.0) | — | cesium pivalate (1.2) | PGMEA (1,000) CyH (1,000) PGME (300) |
| 23 | Resist 23 | Polymer 1 (100) | Sodium Salt 1 (2.0) | — | cesium pivalate (1.2) | PGMEA (1,000) CyH (1,000) PGME (300) |
| 24 | Resist 24 | Polymer 1 (100) | Potassium Salt 1 (2.5) | — | cesium pivalate (1.2) | PGMEA (1,000) CyH (1,000) PGME (300) |
| 25 | Resist 25 | Polymer 1 (100) | Calcium Salt 1 (4.0) | — | cesium pivalate (1.2) | PGMEA (1,000) CyH (1,000) PGME (300) |
| 26 | Resist 26 | Polymer 1 (100) | Magnesium Salt 1 (4.0) | — | cesium pivalate (1.2) | PGMEA (1,000) CyH (1,000) PGME (300) |

TABLE 3

| | Resist | Polymer (pbw) | Metal compound (pbw) | Acid generator (pbw) | Quencher (pbw) | Organic solvent (pbw) |
|---|---|---|---|---|---|---|
| Comparative Example 1 | Comparative Resist 1 | Polymer 1 (100) | — | — | Amine 1 (1.3) | PGMEA (1,000) CyH (1,000) GBL (200) |
| 2 | Comparative Resist 2 | Polymer 1 (100) | — | — | Amine 1 (0.6) | PGMEA (1,000) CyH (1,000) GBL (200) |
| 3 | Comparative Resist 3 | Polymer 1 (100) | — | — | cesium pivalate (1.2) | PGMEA (1,000) CyH (1,000) GBL (200) |

EB Writing Test

Using a coater/developer system Clean Track Mark 5 (Tokyo Electron Ltd.), the positive resist composition was spin coated onto a silicon substrate (diameter 6 inches, vapor primed with hexamethyldisilazane (HMDS)) and pre-baked on a hot plate at 110° C. for 60 seconds to form a resist film of 70 nm thick. Using a system HL-800D (Hitachi Ltd.) at a HV voltage of 50 kV, the resist film was exposed imagewise to EB in a vacuum chamber.

Using Clean Track Mark 5, immediately after the imagewise exposure, the resist film was baked (PEB) on a hot plate at the temperature shown in Table 2 for 60 seconds and puddle developed in a 2.38 wt % tetramethylammonium hydroxide (TMAH) aqueous solution for 30 seconds to form a positive pattern.

Sensitivity is the exposure dose that provides a 1:1 resolution of a 100-nm line-and-space pattern. The 100-nm line-and-space pattern at that dose was measured for line width roughness (LWR) under SEM.

The resist composition is shown in Table 4 along with the sensitivity and LWR of EB lithography.

TABLE 4

| | Resist | PEB temp. (° C.) | Sensitivity (μC/cm²) | LWR (nm) |
|---|---|---|---|---|
| Example | 1 Resist 1 | 85 | 26.5 | 6.9 |
| | 2 Resist 2 | 80 | 28.5 | 5.1 |
| | 3 Resist 3 | 80 | 25.0 | 6.3 |
| | 4 Resist 4 | 80 | 25.0 | 5.5 |
| | 5 Resist 5 | 70 | 26.0 | 6.3 |
| | 6 Resist 6 | 85 | 25.0 | 5.1 |
| | 7 Resist 7 | 85 | 26.0 | 6.1 |
| | 8 Resist 8 | 85 | 25.0 | 5.7 |
| | 9 Resist 9 | 85 | 24.0 | 6.5 |
| | 10 Resist 10 | 85 | 26.0 | 6.2 |
| | 11 Resist 11 | 85 | 28.0 | 5.1 |
| | 12 Resist 12 | 85 | 21.0 | 6.1 |
| | 13 Resist 13 | 85 | 26.0 | 5.0 |
| | 14 Resist 14 | 85 | 25.0 | 5.5 |
| | 15 Resist 15 | 85 | 25.6 | 5.1 |
| | 16 Resist 16 | 85 | 26.0 | 5.4 |
| | 17 Resist 17 | 85 | 26.0 | 5.1 |
| | 18 Resist 18 | 85 | 22.6 | 5.4 |
| | 19 Resist 19 | 85 | 19.0 | 5.8 |
| | 20 Resist 20 | 85 | 19.5 | 5.9 |
| | 21 Resist 21 | 85 | 26.0 | 4.4 |
| | 22 Resist 22 | 85 | 16.5 | 5.9 |
| | 23 Resist 23 | 85 | 24.0 | 4.8 |
| | 24 Resist 24 | 85 | 25.0 | 4.7 |
| | 25 Resist 25 | 85 | 22.0 | 4.1 |
| | 26 Resist 26 | 85 | 20.5 | 4.9 |
| Comparative Example | 1 Comparative Resist 1 | 85 | 35.5 | 7.2 |
| | 2 Comparative Resist 2 | 85 | 21.5 | 9.2 |
| | 3 Comparative Resist 3 | 85 | 36.5 | 7.2 |

It is evident from Table 4 that the resist compositions of Examples have a high sensitivity and reduced LWR. The resist compositions of Comparative Examples have sensitivity and LWR values which are inferior to those of Examples. It is demonstrated that the resist composition comprising a polymer comprising acid labile group-containing recurring units and preferably acid generator-containing recurring units, and a sodium, magnesium, potassium, calcium, rubidium, strontium, yttrium, cesium, barium or cerium salt of α-fluorinated sulfonic acid bonded to a $C_5$-$C_{30}$ straight, branched or cyclic alkyl, alkenyl or alkynyl group or $C_6$-$C_{20}$ aryl group exhibits a high resolution, a high sensitivity, and a minimal LWR. The resist composition is best suited as the resist material for VLSIs and patterning material for masks.

It is noted that the invention is not limited to the aforementioned embodiments. While the embodiments are merely exemplary, any embodiments having substantially the same construction as the technical concept set forth in the following claims and exerting equivalent functions and results are believed to be within the spirit and scope of the invention.

Japanese Patent Application Nos. 2015-208583, 2016-134659 and 2016-181229 are incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A resist composition comprising a base resin comprising recurring units containing an acid labile group and a salt, wherein the salt is a barium salt having the formula (2), a cesium salt having the formula (3) or a cerium salt having the formula (4):

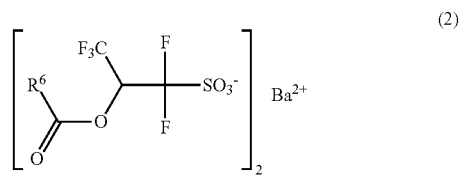

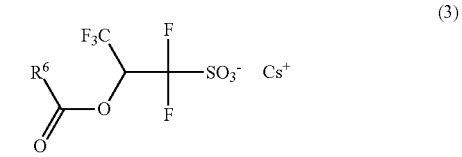

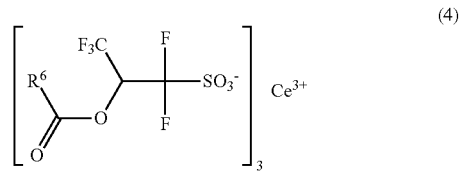

wherein $R^6$ is a $C_4$-$C_{20}$ straight, branched or cyclic alkyl, alkenyl or alkynyl group or $C_6$-$C_{20}$ aryl group, which may contain halogen, ether, thiol, ester, carbonate, carbonyl, amide, amino, azide, carbamate, nitro, cyano, hydroxyl, carboxyl, sulfo, sulfonic acid ester, sultone moiety, lactone ring or lactam ring.

2. The resist composition of claim 1 wherein the recurring units containing an acid labile group have the formula (a1) or (a2):

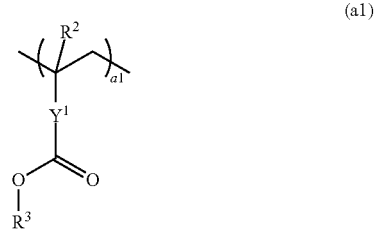

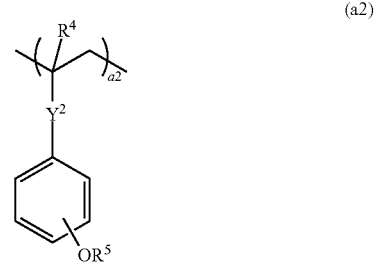

wherein $R^2$ and $R^4$ are each independently hydrogen or methyl, $R^3$ and $R^5$ each are an acid labile group, $Y^1$ is a single bond, a $C_1$-$C_{12}$ linking group having at least one of ester moiety, lactone ring, phenylene moiety and naphthylene moiety, a phenylene group, or a naphthylene group, $Y^2$ is a single bond, ester group or amide group, a1 and a2 are numbers in the range: $0 \leq a1 \leq 0.9$, $0 \leq a2 \leq 0.9$, and $0 < a1 + a2 < 1$.

3. The resist composition of claim 1 wherein the base resin further comprises recurring units of at least one type selected from the formulae (b1), (b2) and (b3):

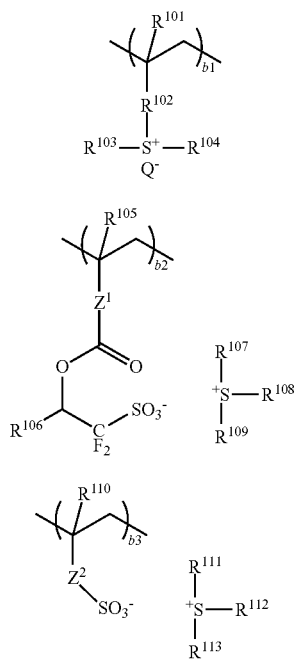

(b1)

(b2)

(b3)

wherein $R^{101}$, $R^{105}$, and $R^{110}$ each are hydrogen or methyl, $R^{102}$ is a single bond, phenylene, —O—$R^{114}$—, or —C(=O)—Y—$R^{114}$—, Y is —O— or —NH—, $R^{114}$ is a straight, branched or cyclic $C_1$-$C_6$ alkylene group, phenylene group or straight, branched or cyclic $C_3$-$C_{10}$ alkenylene group, which may contain a carbonyl, ester, ether or hydroxyl moiety, $R^{103}$, $R^{104}$, $R^{107}$, $R^{108}$, $R^{109}$, $R^{111}$, $R^{112}$, and $R^{113}$ are each independently a straight, branched or cyclic $C_1$-$C_{12}$ alkyl group which may contain a carbonyl, ester or ether moiety, or a $C_6$-$C_{12}$ aryl, $C_7$-$C_{20}$ aralkyl, or mercaptophenyl group which may contain a straight, branched or cyclic $C_1$-$C_{10}$ alkyl, halogen, trifluoromethyl, cyano, nitro, hydroxyl, alkoxy, alkoxycarbonyl or acyloxy moiety, $R^{106}$ is hydrogen or trifluoromethyl, $Z^1$ is a single bond or —C(=O)—$Z^3$—$R^{115}$—, $Z^2$ is a single bond, methylene, ethylene, phenylene, fluorinated phenylene, —O—$R^{115}$— or —C(=O)—$Z^3$—$R^{115}$—, $Z^3$ is —O— or —NH—, $R^{115}$ is a straight, branched or cyclic $C_1$-$C_6$ alkylene group, phenylene group or straight, branched or cyclic $C_1$-$C_6$ alkenylene group, which may contain a carbonyl, ester, ether or hydroxyl moiety, a pair of $R^{103}$ and $R^{104}$, $R^{107}$ and $R^{108}$, $R^{107}$ and $R^{109}$, $R^{108}$ and $R^{109}$, $R^{111}$ and $R^{112}$, $R^{111}$ and $R^{113}$, or $R^{112}$ and $R^{113}$ may bond directly or via a methylene moiety or ether bond to form a ring with the sulfur atom to which they are attached, $Q^-$ is a non-nucleophilic counter ion, b1, b2 and b3 are numbers in the range: $0 \leq b1 \leq 0.5$, $0 \leq b2 \leq 0.5$, $0 \leq b3 \leq 0.5$, and $0 < b1+b2+b3 \leq 0.5$.

4. The resist composition of claim 3 wherein the base resin comprises recurring units of the formula (b2).

5. The resist composition of claim 1, further comprising an acid generator, the composition being a chemically amplified positive resist composition.

6. The resist composition of claim 1, further comprising at least one component selected from among an organic solvent, a dissolution inhibitor, a basic compound, and a surfactant.

7. The resist composition of claim 1 wherein the salt is in an amount of 0.01 to 100 parts per 100 parts by weight of the base resin.

8. A pattern forming process comprising the steps of coating the resist composition of claim 1 onto a substrate, baking, exposing the resulting resist film to high-energy radiation, and developing with a developer.

9. The process of claim 8 wherein the high-energy radiation is EUV of wavelength 3 to 15 nm.

10. The process of claim 8 wherein the high-energy radiation is EB at an accelerating voltage of 1 to 150 kV.

11. The process of claim 9 wherein in the step of exposing the resist film to high-energy radiation, the surface of the substrate underneath the resist film is electrically charged positive.

12. A barium salt having the formula (2), a cesium salt having the formula (3) or a cerium salt having the formula (4):

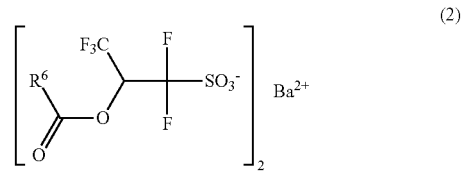 (2)

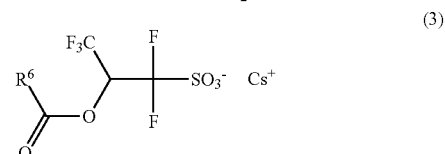 (3)

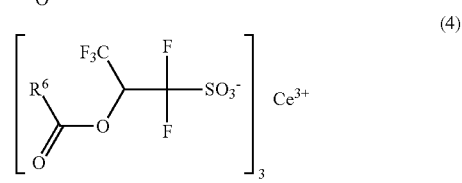 (4)

wherein $R^6$ is a $C_4$-$C_{20}$ straight, branched or cyclic alkyl, alkenyl or alkynyl group or $C_6$-$C_{20}$ aryl group, which may contain halogen, ether, thiol, ester, carbonate, carbonyl, amide, amino, azide, carbamate, nitro, cyano, hydroxyl, carboxyl, sulfo, sulfonic acid ester, sultone moiety, lactone ring or lactam ring.

* * * * *